(12) United States Patent
Himmelsbach et al.

(10) Patent No.: US 7,482,337 B2
(45) Date of Patent: Jan. 27, 2009

(54) XANTHINE DERIVATIVES, THE PREPARATION THEREOF AND THEIR USE AS PHARMACEUTICAL COMPOSITIONS

(75) Inventors: Frank Himmelsbach, Mittelbiberach (DE); Elke Langkopf, Warthausen (DE); Matthias Eckhardt, Biberach (DE); Roland Maier, Biberach (DE); Michael Mark, Biberach (DE); Mohammad Tadayyon, Ulm (DE); Ralf R. H. Lotz, Schemmerhofen (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

(21) Appl. No.: 10/695,597

(22) Filed: Oct. 28, 2003

(65) Prior Publication Data

US 2004/0138214 A1     Jul. 15, 2004

Related U.S. Application Data

(60) Provisional application No. 60/429,173, filed on Nov. 26, 2002.

(30) Foreign Application Priority Data

Nov. 8, 2002   (DE)   ................... 102 51 927

(51) Int. Cl.
*C07D 473/06*   (2006.01)
*C07D 519/00*   (2006.01)
*A61K 31/522*   (2006.01)
*A61K 31/538*   (2006.01)
*A61K 31/536*   (2006.01)
*A61K 31/5415*  (2006.01)
*A61K 31/5513*  (2006.01)
*A61P 3/10*     (2006.01)
*A61P 3/04*     (2006.01)

(52) U.S. Cl. .............. 514/211.09; 514/211.11; 514/212.07; 514/224.2; 514/234.2; 514/263.2; 514/263.21; 514/263.22; 514/263.35; 514/263.34; 514/226.8; 514/228.5; 514/221; 540/552; 540/514; 540/545; 540/587; 540/569; 544/49; 544/50; 544/51; 544/63; 544/92; 544/105; 544/118; 544/268; 544/269; 544/272

(58) Field of Classification Search .............. 514/224.2, 514/234.2, 263.2, 263.21, 263.22, 263.35, 514/263.34, 226.8, 228.5, 221, 211.1, 212.07, 514/211.09, 211.11; 544/90, 92, 63, 49, 544/50, 51, 105, 118, 268, 269, 272; 540/552, 540/545, 514, 587, 569
See application file for complete search history.

(56) References Cited

U.S. PATENT DOCUMENTS

| 2,928,833 | A  | 3/1960  | Leake et al.          |
|-----------|----|---------|------------------------|
| 4,005,208 | A  | 1/1977  | Bender                 |
| 4,599,338 | A  | 7/1986  | Regnier et al.         |
| 5,041,448 | A  | 8/1991  | Janssens               |
| 5,051,517 | A  | 9/1991  | Findeisen              |
| 5,223,499 | A  | 6/1993  | Greenlee               |
| 5,234,897 | A  | 8/1993  | Findeisen et al.       |
| 5,258,380 | A  | 11/1993 | Janssens               |
| 5,266,555 | A  | 11/1993 | Findeisen et al.       |
| 5,389,642 | A  | 2/1995  | Dorsch                 |
| 5,470,579 | A  | 11/1995 | Bonte et al.           |
| 5,719,279 | A  | 2/1998  | Kuefner-Muhl et al.    |
| 5,753,635 | A  | 5/1998  | Buckman                |
| 6,303,661 | B1 | 10/2001 | Demuth                 |
| 6,342,601 | B1 | 1/2002  | Bantick                |
| 6,548,481 | B1 | 4/2003  | Demuth et al.          |
| 6,579,868 | B1 | 6/2003  | Asano                  |
| 6,784,195 | B2 | 8/2004  | Hale et al.            |
| 6,821,978 | B2 | 11/2004 | Chackalamannil         |
| 6,869,947 | B2 * | 3/2005 | Kanstrup et al. ....... 514/217.06 |
| 7,060,722 | B2 | 6/2006  | Kitajima               |
| 7,074,794 | B2 | 7/2006  | Kitajima               |
| 7,074,798 | B2 | 7/2006  | Yoshikawa              |
| 7,074,923 | B2 | 7/2006  | Dahanukar              |
| 7,109,192 | B2 | 9/2006  | Hauel                  |
| 7,179,809 | B2 | 2/2007  | Eckhardt               |
| 7,183,280 | B2 | 2/2007  | Himmelsbach            |
| 7,192,952 | B2 | 3/2007  | Kanstrup               |
| 7,217,711 | B2 | 5/2007  | Eckhardt               |
| 7,235,538 | B2 | 6/2007  | Kanstrup et al.        |

(Continued)

FOREIGN PATENT DOCUMENTS

CA      2136288 A1    5/1995

(Continued)

OTHER PUBLICATIONS

Busso et al., American Journal of Pathology 166:433-442 (2005).*

(Continued)

*Primary Examiner*—Mark L Berch
(74) *Attorney, Agent, or Firm*—Michael P. Morris; Mary-Ellen M. Devlin; David L. Kershner

(57) ABSTRACT

Disclosed are substituted xanthines of general formula (I)

$$\begin{array}{c} \text{structure with } R^1, R^2, R^3, R^4 \text{ substituents on xanthine core} \end{array}$$

wherein $R^1$ to $R^4$ are defined hereinbelow, the tautomers, the stereoisomers, the mixtures thereof, the prodrugs thereof and the salts thereof, which have valuable pharmacological properties, particularly an inhibitory effect on the activity of the enzyme dipeptidylpeptidase-IV (DPP-IV).

9 Claims, No Drawings

U.S. PATENT DOCUMENTS

| | | | |
|---|---|---|---|
| 2002/0161001 A1 | 10/2002 | Kanstrup | |
| 2002/0169174 A1 | 11/2002 | Chacklamannil et al. | |
| 2002/0198205 A1 | 12/2002 | Himmelsbach et al. | |
| 2003/0105077 A1 | 6/2003 | Kanstrup et al. | |
| 2003/0199528 A1 | 10/2003 | Kanstrup | |
| 2003/0232987 A1 | 12/2003 | Dahanukar et al. | |
| 2003/0236272 A1 | 12/2003 | Carr | |
| 2004/0034014 A1 | 2/2004 | Kanstrup et al. | |
| 2004/0077645 A1* | 4/2004 | Himmelsbach et al. | 514/234.5 |
| 2004/0082570 A1 | 4/2004 | Yoshikawa | |
| 2004/0087587 A1 | 5/2004 | Himmelsbach | |
| 2004/0097510 A1* | 5/2004 | Himmelsbach et al. | 514/248 |
| 2004/0116328 A1 | 6/2004 | Yoshikawa et al. | |
| 2004/0122228 A1 | 6/2004 | Maier | |
| 2004/0138215 A1* | 7/2004 | Eckhardt et al. | 514/234.5 |
| 2004/0166125 A1 | 8/2004 | Himmelsbach | |
| 2005/0020574 A1 | 1/2005 | Hauel et al. | |
| 2005/0026921 A1 | 2/2005 | Eckhardt | |
| 2005/0130985 A1 | 6/2005 | Himmelsbach | |
| 2005/0171093 A1 | 8/2005 | Eckhardt et al. | |
| 2005/0187227 A1 | 8/2005 | Himmelsbach et al. | |
| 2005/0203095 A1 | 9/2005 | Eckhardt | |
| 2005/0234108 A1 | 10/2005 | Himmelsbach et al. | |
| 2005/0261352 A1 | 11/2005 | Eckhardt | |
| 2006/0004074 A1 | 1/2006 | Eckhardt | |
| 2006/0058323 A1 | 3/2006 | Eckhardt et al. | |
| 2006/0063787 A1 | 3/2006 | Yoshikawa | |
| 2006/0079541 A1 | 4/2006 | Langkopf | |
| 2006/0094722 A1 | 5/2006 | Yasuda | |
| 2006/0142310 A1 | 6/2006 | Pfrengle et al. | |
| 2006/0173056 A1 | 8/2006 | Kitajima | |
| 2006/0247226 A1 | 11/2006 | Himmelsbach | |
| 2007/0027168 A1 | 2/2007 | Pfrengle et al. | |
| 2007/0088038 A1 | 4/2007 | Eckhardt | |
| 2007/0093659 A1 | 4/2007 | Bonfanti | |
| 2007/0142383 A1 | 6/2007 | Eckhardt | |
| 2007/0185091 A1 | 8/2007 | Himmelsbach et al. | |
| 2007/0219178 A1 | 9/2007 | Muramoto | |
| 2007/0255900 A1 | 11/2007 | Sieger | |
| 2007/0281940 A1 | 12/2007 | Dugi | |

FOREIGN PATENT DOCUMENTS

| | | |
|---|---|---|
| CA | 2418656 A1 | 2/2002 |
| CA | 2496325 A1 | 3/2004 |
| CA | 2496249 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2590912 A1 | 6/2006 |
| DE | 101 09 021 | 2/2001 |
| DE | 101 17 803 | 4/2001 |
| EP | 0149578 A2 | 7/1985 |
| EP | 0400974 A2 | 5/1990 |
| EP | 0399285 A1 | 11/1990 |
| EP | 0412358 A1 | 2/1991 |
| EP | 0524482 A1 | 1/1993 |
| EP | 0657454 A1 | 6/1995 |
| EP | 1054012 A1 | 11/2000 |
| EP | 1338595 A2 | 8/2003 |
| EP | 1514552 A1 | 3/2005 |
| EP | 1537880 A1 | 8/2005 |
| ES | 385302 A1 | 4/1973 |
| FR | 2707641 A1 | 1/1995 |
| JP | S37-4895 | 6/1962 |
| JP | 2003/300977 | 10/2003 |
| JP | 2006/045156 | 2/2006 |
| WO | 91/07945 A1 | 6/1991 |
| WO | 94/03456 A1 | 2/1994 |
| WO | 99/29695 A1 | 6/1999 |
| WO | 02/02560 A2 | 1/2002 |
| WO | 02/14271 A1 | 2/2002 |
| WO | 02/24698 A1 | 3/2002 |
| WO | WO 02/068420 A1 | 9/2002 |
| WO | 03/004496 A1 | 1/2003 |
| WO | 03/024965 A2 | 3/2003 |
| WO | 03/057200 A2 | 7/2003 |
| WO | 03/104229 A1 | 12/2003 |
| WO | 2004/018467 A2 | 3/2004 |
| WO | 2004/018468 A2 | 3/2004 |
| WO | WO 2004018468 A2 * | 3/2004 |
| WO | 2004/028524 A1 | 4/2004 |
| WO | 2004/033455 A2 | 4/2004 |
| WO | WO 2004033455 A2 * | 4/2004 |
| WO | 2004/041820 A1 | 5/2004 |
| WO | 2004/046148 A1 | 6/2004 |
| WO | 2004/048379 A1 | 6/2004 |
| WO | 2004/096806 A1 | 11/2004 |
| WO | 2004/108730 A1 | 12/2004 |
| WO | 2004/050658 A1 | 6/2005 |
| WO | 2005/058901 A1 | 6/2005 |
| WO | 2005/082906 A1 | 9/2005 |
| WO | 2005/085246 A1 | 9/2005 |
| WO | 2004/111051 A1 | 12/2005 |
| WO | 2006/029769 A1 | 3/2006 |
| WO | 2006/048427 A1 | 5/2006 |
| WO | 2006/068163 A1 | 6/2006 |
| WO | 2007/017423 A2 | 2/2007 |

OTHER PUBLICATIONS

"Patient Information Januvia™" <http://www.merck.com/product/usa/pi_circulars/j/januvia/januvia_ppi.pdf> downloaded from the internet Apr. 30, 2008.*

U.S. Appl. No. 11/744,701, filed May 4, 2007, Kohlrausch.

Augustyns, K. et al., The Unique Properties of Dipeptidly-peptidase IV (DPP IV/CD 26) and the Therapeutic Potential of DPP-IV Inhibitors, Current Medical Chemistry, vol. 6, No. 4, 1999, pp. 331-327.

Beljean-Leymarie et al., Hydrazines et hydrazones hétérocycliques. IV. Synthéses de dérivès de l'hydrazine dans la série des imidazo[4,5-d]pyridazinones-4, Can. J. Chem., vol. 61, No. 11, 1983, pp. 2563-2566.

Bollag, R.J. et al; "Osteoblast-Derived Cells Express Functional Glucose-Dependent Insulinotropic Peptide Receptors," Endocrinology, vol. 141, No. 3, 2000, pp. 1228-1235.

Brittain, H.G., "Methods for the Characterization of Polymorphs: X-Ray Powder Diffraction" Polymorphism in Pharmaceutical Solids, 1999, p. 235-238.

Busso et al., "Circulating CD26 is Negatively Associated with Inflammation in Human and Experimental Arthritis," Am. J. Path., vol. 166, No. 2, Feb. 2005, pp. 433-442.

Caira, M.R., "Crystalline polymorphism of organic compounds" Topics in Current Chemistry, Springer, Berlin, vol. 198, 1998, p. 163-208.

Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.

Cygankiewicz, Andrzej et al., Investigations into the Piperazine Derivatives of Dimethylxanthine:, ACTA POLON. Pharm. [Papers of Polish Pharmacology], XXXOV, No. 5, pp. 607-612, 1977.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

DeMeester, I. et al.; "CD26, let it cut or cut it down", Review: Immunology Today; Aug. 1999, vol. 20, No. 8 pp. 367-375.

Korom, S. et al; Inhibition of CD26/dipeptidyl peptidase IV activity in vivo prolongs cardiac allograft survival in rat recipients[1,2], Transplantation, May 27, 1997, vol. 63, No. 10, pp. 1495-1500.

Pospisilik, et al; Dipeptidyl Peptidase IV Inhibitor Treatment Stimulates β-Cell Survival and Islet Neogenesis in Streptozotocin-Induced Diabetic Rats; Diabetes, vol. 52, Mar. 2003, pp. 741-750.

Rhee et al.: "Nitrogen-15-Labeled Deoxynucleosides. 3. Synthesis of [3-$^{15}$N]-2'-Deoxyadenosine" J. Am. Chem. Soc. 1990, 112, 8174-8175.

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Tanaka, S. et al; "Suppression of Arthritis by the Inhibitors of Dipeptidyl Peptidase IV," In. J. Immunopharmac., vol. 19, No. 1, pp. 15-24, 1997.

Wolff, M.E.: "Burger's Medicinal Chemistry and Drug Discovery" Fifth Edition, vol. 1: Principles and Practice, pp. 975-977, 1994, John Wiley & Sons, Inc.

Zhong, Qing et al; "Glucose-dependent insulinotropic peptide stimulates proliferation and TGF-β release from MG-63 cells," Peptides 24 (2003) 611-616.

Chemical Abstracts Accession No. 1987:95577: Abstract of Romanenko et al., "Synthesis and biological activity of 3-methyl, 7- or 8-alkyl, 7,8-dialkyl, heterocyclic, and cyclochexylaminoxanthines," Farmatsevtichnii Zhurnal, 1986, (Kiev), vol. 5, 1986, pp. 41-44.

Chemical Abstracts Accession No. 106:95577 Romanenko et al., "Synthesis and biological activity of 3-methyl, 7-or 8-alkyl-7,8-dialkyl, heterocyclic, and cyclohexylaminoxanthines," Zaporozh. Med. Institute (1986).

Yoshikawa, Seiji et al.: Chemical Abstract of Japanese Patent No. WO 2003/104229 Preparation of purinone derivatives as dipeptidylpeptidase IV (DPP-IV) inhibitors.

Patani George A. et al.: "Bioisoterism : A Rational Approach in Drug Design", Chemical Reviews, 1996, vol. 96, No. 8, pp. 3147-3176.

International Search Report for PCT/EP03/09127 mailed Nov. 28, 2003.

International Search Report for PCT/EP03/12821 mailed Mar. 30, 2004.

International Search Report for PCT/EP03/13648 mailed Apr. 5, 2004.

International Search Report for PCT/EP2007/054270 mailed Aug. 14, 2007.

International Search Report for PCT/EP2007/058181 mailed Nov. 28, 2007.

International Search Report for PCT/EP2007/054204 mailed Aug. 3, 2007.

International Search Report for PCT/EP2007/054201 mailed Aug. 29, 2007.

* cited by examiner

XANTHINE DERIVATIVES, THE PREPARATION THEREOF AND THEIR USE AS PHARMACEUTICAL COMPOSITIONS

APPLICATION DATA

This application claims benefit to German application DE 102 51 927 filed Nov. 8, 2002 and U.S. provisional application No. 60/429,173 Nov. 26, 2002.

DETAILED DESCRIPTION OF THE INVENTION

The present invention relates to new substituted xanthines of general formula

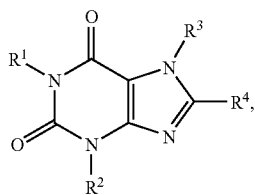

(I)

the tautomers, enantiomers, diastereomers, the mixtures thereof, the prodrugs thereof and the salts thereof, particularly the physiologically acceptable salts thereof with inorganic or organic acids or bases which have valuable pharmacological properties, particularly an inhibiting effect on the activity of the enzyme dipeptidylpeptidase-IV (DPP-IV), the preparation thereof, the use thereof for the prevention or treatment of diseases or conditions associated with an increased DPP-IV activity or capable of being prevented or alleviated by reducing the DPP-IV activity, particularly type I or type II diabetes mellitus, the pharmaceutical compositions containing a compound of general formula (I) or a physiologically acceptable salt thereof as well as processes for the preparation thereof.

The present invention thus relates to the above compounds of general formula I which have valuable pharmacological properties, the pharmaceutical compositions containing the pharmacologically effective compounds, the use thereof and processes for the preparation thereof.

In the above general formula I $R^1$ denotes a $C_{1-3}$-alkyl group substituted by a group $R_a$, wherein $R_a$ denotes a 1,4-dihydro-quinazolinyl or 3,4-dihydro-quinazolinyl group wherein in each case in the benzo moiety
one to three methyne groups may be replaced by nitrogen atoms, a 3,4-dihydro-isoquinolinyl, 1H-benzo[d][1,2]oxazinyl, 4H-benzo[e][1,3]oxazinyl, 4H-benzo[d][1,3]oxazinyl or 2H-benzo[1,4]oxazinyl group, wherein in each case
in the benzo moiety one to three methyne groups may be replaced by nitrogen atoms and in the heterocyclyl moiety a methylene group may be replaced by a carbonyl group, a 4H-benzo[e][1,3]thiazinyl, 4H-benzo[d][1,3]thiazinyl or 2H-benzo[1,4]thiazinyl group, wherein in each case
in the benzo moiety one to three methyne groups may be replaced by nitrogen atoms and in the heterocyclyl moiety a methylene group may be replaced by a carbonyl group and a sulphur atom may be replaced by a sulphinyl or sulphonyl group, a 2-oxo-2H-benzo[e][1,3]oxazinyl or 2,2-dioxo-1H-benzo[c][1,2]thiazinyl group, wherein in each case in the benzo moiety
one to three methyne groups may be replaced by nitrogen atoms, a 2,3-dihydro-1H-benzo[e][1,4]diazepinyl, 4,5-dihydro-3H-benzo[b]-[1,4]diazepinyl or 5-oxo-4,5-dihydro-3H-benzo[e][1,4]diazepinyl group, wherein in each case
in the benzo moiety one to three methyne groups may be replaced by nitrogen atoms and in the heterocyclyl moiety a methylene group may be replaced by a carbonyl group, a 2,3-dihydro-benzo[f][1,4]oxazepinyl or 2,3-dihydro-benzo[b][1,4]oxa-zepinyl group wherein in each case
in the benzo moiety one to three methyne groups may be replaced by nitrogen atoms and in the heterocyclyl moiety a methylene group may be replaced by a carbonyl group, a 2,3-dihydro-benzo[f][1,4]thiazepinyl or 2,3-dihydro-benzo[b][1,4]thiazepinyl group, wherein in each case
in the benzo moiety one to three methyne groups may be replaced by nitrogen atoms and in the heterocyclyl moiety a methylene group may be replaced by a carbonyl group and a sulphur atom may be replaced by a sulphinyl or sulphonyl group, a 5-oxo-4,5-dihydro-benzo[f][1,3,4]oxadiazepinyl group wherein in the benzo moiety
one to three methyne groups may be replaced by nitrogen atoms, an 11H-dibenzo[b,e]azepinyl or 5H-dibenzo[a,d]cycloheptenyl group, wherein in each case
in the benzo moiety one to three methyne groups may be replaced by nitrogen atoms and the methylene group in the heterocyclyl moiety may be replaced by an oxygen or sulphur atom, a carbonyl, sulphinyl, sulphonyl or an imino group substituted by $R_x$, where
$R_x$ denotes a hydrogen atom or a $C_{1-4}$-alkyl, $C_{2-4}$-alkenyl, $C_{2-4}$-alkynyl, $C_{3-6}$-cycloalkyl, $C_{3-6}$-cycloalkyl-$C_{1-3}$-alkyl, aryl, aryl-$C_{1-3}$-alkyl, hydroxy-$C_{2-4}$-alkyl, $C_{1-3}$-alkyloxy-$C_{2-4}$-alkyl, $C_{3-6}$-cycloalkyloxy-$C_{2-4}$-alkyl, amino-$C_{2-4}$-alkyl, $C_{1-3}$-alkylamino-$C_{2-4}$-alkyl, di-($C_{1-3}$-alkyl)-amino-$C_{2-4}$-alkyl, $C_{1-3}$-alkyl-carbonyl, $C_{1-3}$-alkyloxy-carbonyl, $C_{1-3}$-alkyloxy-carbonyl-$C_{1-3}$-alkyl, aryl-carbonyl, $C_{1-3}$-alkyl-sulphonyl or aryl-sulphonyl group, a phenanthridinyl, 1,2,3,4-tetrahydro-phenanthridinyl, benzo[f]quino-xalinyl, 5H-dibenzo[d,f][1,3]diazepinyl, 5H-benzo[e]pyrrolo[1,2-a][1,4]diazepinyl, thieno[3,2-b][1,4]benzoxazepinyl or a 3-oxo-2,3-dihydro-isoindol-1-ylidene group, wherein in each case
in the benzo moiety one to three methyne groups may be replaced by nitrogen atoms, a benzo[1,2,5]oxadiazolyl, dibenzofuranyl, indolizinyl, 1H-perimidinyl, group, a pyrazolo[1,5-c]quinazolinyl group or an imidazo[2,1-a]isoquinolinyl or imidazo[1,2-a]isoquinolinyl group
wherein the above-mentioned groups $R_a$ may be substituted by the groups $R^{10}$ to $R^{13}$ and may additionally be substituted by a $C_{1-3}$-alkyl group and $R^{10}$ denotes a hydrogen atom,
a fluorine, chlorine, bromine or iodine atom,
a $C_{1-4}$-alkyl, hydroxy, or $C_{1-4}$-alkyloxy group,
a nitro, amino, $C_{1-3}$-alkylamino, di-($C_{1-3}$-alkyl)amino, cyano-$C_{1-3}$-alkylamino, [N-(cyano-$C_{1-3}$-alkyl)-N-$C_{1-3}$-alkyl-amino], $C_{1-3}$-alkyloxy-carbonyl-$C_{1-3}$- alkylamino, pyrrolidin-1-yl, piperidin-1-yl, morpholin-4-yl, piperazin-1-yl, or 4-($C_{1-3}$-alkyl)-piperazin-1-yl group, a $C_{1-3}$-alkyl-carbonylamino, arylcarbonylamino, aryl-$C_{1-3}$-alkyl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino or 4-($C_{1-3}$-alkyl)-piperazin-1-yl-carbonylamino, $C_{1-3}$-alkyl-sulphonylamino, bis-($C_{1-3}$-alkylsulphonyl)-amino, aminosulphonylamino, $C_{1-3}$-alkylamino-sulphonylamino, di-($C_{1-3}$-alkyl)amino-sulphonylamino, pyrrolidin-1-yl-sulphonylamino, piperidin-1-yl-sulphonylamino, morpholin-4-yl-sulphonylamino, piperazin-1-yl-sulphonylamino or 4-($C_{1-3}$-alkyl)-piperazin-1-yl-sulphonylamino, ($C_{1-3}$-alkylamino)thiocarbonylamino, ($C_{1-3}$-alkyloxy-carbonylamino)-carbonylamino, arylsulphonylamino or aryl-$C_{1-3}$-alkyl-sulphonylamino group, an N-($C_{1-3}$-alkyl)-$C_{1-3}$-alkyl-carbonylamino, N-($C_{1-3}$-alkyl)-arylcarbonylamino, N-($C_{1-3}$-alkyl)-aryl-$C_{1-3}$-alkyl-carbonylamino, N-($C_{1-3}$-alkyl)-$C_{1-3}$-alkyloxy-carbonylamino, N-(aminocarbonyl)-$C_{1-3}$-alkylamino, N-($C_{1-3}$-alkyl-aminocarbonyl)-$C_{1-3}$-alkylamino, N-[di-($C_{1-3}$-alkyl)aminocarbonyl]-$C_{1-3}$-alkylamino, N-($C_{1-3}$-alkyl)-$C_{1-3}$-alkyl-sulphonylamino, N-($C_{1-3}$-alkyl)-arylsulphonylamino or N-($C_{1-3}$-alkyl)-aryl-$C_{1-3}$-alkyl-sulphonylamino group, a 2-oxo-imidazolidin-1-yl, 2,4-dioxo-imidazolidin-1-yl, 2,5-dioxo-imidazolidin-1-yl or 2-oxo-hexahydro-pyrimidin-1-yl group wherein the nitrogen atom in the 3 position may be substituted in each case by a methyl or ethyl group, a cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl or 4-($C_{1-3}$-alkyl)-piperazin-1-yl-carbonyl group, a $C_{1-3}$-alkyl-carbonyl or an arylcarbonyl group, a carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, piperazin-1-yl-carbonyl-$C_{1-3}$-alkyl or 4-($C_{1-3}$-alkyl)-piperazin-1-yl-carbonyl-$C_{1-3}$-alkyl group, a carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyloxy, piperidin-1-yl-carbonyl-$C_{1-3}$-alkyloxy, morpholin-4-yl-carbonyl-$C_{1-3}$-alkyl-oxy, piperazin-1-yl-carbonyl-$C_{1-3}$-alkyloxy or 4-($C_{1-3}$-alkyl)-piperazin-1-yl-carbonyl-$C_{1-3}$-alkyloxy group, a hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, piperidin-1-yl-$C_{1-3}$-alkyl, morpholin-4-yl-$C_{1-3}$-alkyl, piperazin-1-yl-$C_{1-3}$-alkyl, 4-($C_{1-3}$-alkyl)-piperazin-1-yl-$C_{1-3}$-alkyl group, a hydroxy-$C_{1-3}$-alkyloxy, $C_{1-3}$-alkyloxy-$C_{1-3}$-alkyloxy, $C_{1-3}$-alkyl-sulphanyl-$C_{1-3}$-alkyloxy, $C_{1-3}$-alkylsulphinyl-$C_{1-3}$-alkyloxy, $C_{1-3}$-alkylsulphonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, piperidin-1-yl-$C_{1-3}$-alkyloxy, morpholin-4-yl-$C_{1-3}$-alkyloxy, piperazin-1-yl-$C_{1-3}$-alkyloxy, 4-($C_{1-3}$-alkyl)-piperazin-1-yl-$C_{1-3}$-alkyloxy group, a mercapto, $C_{1-3}$-alkylsulphanyl, $C_{1-3}$-alkylsulphinyl, $C_{1-3}$-alkylsulphonyl, $C_{1-3}$-alkylsulphonyloxy, arylsulphonyloxy, trifluoromethylsulphanyl, trifluoromethylsulphinyl or trifluoromethylsulphonyl group, a sulpho, aminosulphonyl, $C_{1-3}$-alkyl-aminosulphonyl, di-($C_{1-3}$-alkyl)-amino-sulphonyl, pyrrolidin-1-yl-sulphonyl, piperidin-1-yl-sulphonyl, morpholin-4-yl-sulphonyl, piperazin-1-yl-sulphonyl or 4-($C_{1-3}$-alkyl)-piperazin-1-yl-sulphonyl group, a methyl or methoxy group substituted by 1 to 3 fluorine atoms, an ethyl or ethoxy group substituted by 1 to 5 fluorine atoms, a $C_{2-4}$-alkenyl or $C_{2-4}$-alkynyl group, a $C_{3-4}$-alkenyloxy or $C_{3-4}$-alkynyloxy group, a $C_{3-6}$-cycloalkyl or $C_{3-6}$-cycloalkyloxy group, a $C_{3-6}$-cycloalkyl-$C_{1-3}$-alkyl or $C_{3-6}$-cycloalkyl-$C_{1-3}$-alkyloxy group or an aryl, aryloxy, aryl-$C_{1-3}$-alkyl or aryl-$C_{1-3}$-alkyloxy group, $R^{11}$ and $R^{12}$, which may be identical or different, in each case denote a hydrogen atom, a fluorine, chlorine, bromine or iodine atom, a $C_{1-3}$-alkyl, trifluoromethyl, hydroxy or $C_{1-3}$-alkyloxy group or a cyano group, or $R^{11}$ together with $R^2$, if they are bound to adjacent carbon atoms, also denote a methylenedioxy, difluoromethylenedioxy, ethylenedioxy or a straight-chain $C_{3-5}$-alkylene group and $R^{13}$ denotes a hydrogen atom, a fluorine, chlorine or bromine atom, a trifluoromethyl, $C_{1-3}$-alkyl or $C_{1-3}$-alkyloxy group, $R^2$ denotes a hydrogen atom, a $C_{1-6}$alkyl group, a $C_{2-4}$-alkenyl group, a $C_{3-4}$-alkynyl group, a $C_{3-6}$-cycloalkyl group, a $C_{3-6}$-cycloalkyl-$C_{1-3}$-alkyl group, a tetrahydrofuran-3-yl, tetrahydropyran-3-yl, tetrahydropyran-4-yl, tetrahydrofuranylmethyl or tetrahydropyranylmethyl group, an aryl group, an aryl-$C_{1-4}$-alkyl group, an aryl-$C_{2-3}$-alkenyl group, an arylcarbonyl-$C_{1-2}$-alkyl group, a heteroaryl-$C_{1-3}$-alkyl group, a furanylcarbonylmethyl, thienylcarbonylmethyl, thiazolylcarbonylmethyl or pyridylcarbonylmethyl group, a $C_{1-4}$-alkyl-carbonyl-$C_{1-2}$-alkyl group, a $C_{3-6}$-cycloalkyl-carbonyl-$C_{1-2}$-alkyl group, an aryl-A-$C_{1-3}$-alkyl group, wherein A denotes an oxygen or sulphur atom, an imino, $C_{1-3}$-alkylimino, sulphinyl or sulphonyl group, a $C_{1-4}$-alkyl group substituted by a group $R_b$, wherein $R_b$ denotes a cyano, carboxy, $C_{1-3}$-alkyloxy-carbonyl, aminocarbonyl, $C_{1-3}$-alkylamino-carbonyl, di-($C_{1-3}$-alkyl)-amino-carbonyl, pyrrolidin-1-ylcarbonyl, piperidin-1-ylcarbonyl, morpholin-4-ylcarbonyl, piperazin-1- ylcarbonyl, 4-methylpiperazin-1-ylcarbonyl or 4-ethylpiperazin-1-ylcarbonyl group, or a $C_{2-4}$-alkyl group substituted by a group $R_c$, wherein
$R_c$ denotes a hydroxy, $C_{1-3}$-alkyloxy, amino, $C_{1-3}$-alkylamino, di-($C_{1-3}$-alkyl)-amino, pyrrolidin-1-yl, piperidin-1-yl, morpholin-4-yl, piperazin-1-yl, 4-methyl-piperazin-1-yl or 4-ethyl-piperazin-1-yl group and is isolated from the cyclic nitrogen atom in the 3 position of the xanthine structure by at least two carbon atoms, $R^3$ denotes a $C_{3-8}$-alkyl group, a $C_{1-3}$-alkyl group substituted by a group $R_d$, wherein
$R_d$ denotes a $C_{3-7}$-cycloalkyl group optionally substituted by one or two $C_{1-3}$-alkyl groups,
a $C_{5-7}$-cycloalkenyl group optionally substituted by one or two $C_{1-3}$-alkyl groups,
an aryl group or
a furanyl, thienyl, oxazolyl, isoxazolyl, thiazolyl, isothiazolyl, pyridyl, pyridazinyl, pyrimidyl or pyrazinyl group, wherein the above-mentioned heterocyclic groups may be substituted in each case by one or two $C_{1-3}$-alkyl groups or by a fluorine, chlorine, bromine or iodine atom or by a trifluoromethyl, cyano or $C_{1-3}$-alkyloxy group, a $C_{3-8}$-alkenyl group, a $C_{3-6}$-alkenyl group substituted by a fluorine, chlorine or bromine atom or a trifluoromethyl group, a $C_{3-8}$-alkynyl group, an aryl group or an aryl-$C_{2-4}$-alkenyl group, and $R^4$ denotes an azetidin-1-yl or pyrrolidin-1-yl group which is substituted in the 3 position by an amino, $C_{1-3}$-alkylamino or a di-($C_{1-3}$-alkyl)amino group and may additionally be substituted by one or two $C_{1-3}$-alkyl groups, a piperidin-1-yl or hexahydroazepin-1-yl group which is substituted in the 3 position or in the 4 position by an amino, $C_{1-3}$-alkylamino or a di-($C_{1-3}$-alkyl)amino group and may additionally be substituted by one or two $C_{1-3}$-alkyl groups, a 3-amino-piperidin-1-yl group wherein the piperidin-1-yl-moiety is additionally substituted by an aminocarbonyl, $C_{1-2}$-alkyl-aminocarbonyl, di-($C_{1-2}$-alkyl)aminocarbonyl, pyrrolidin-1-yl-carbonyl, (2-cyano-pyrrolidin-1-yl)-carbonyl, thiazolidin-3-yl-carbonyl, (4-cyano-thiazolidin-3-yl)carbonyl, piperidin-1-ylcarbonyl or morpholin-4-ylcarbonyl group, a 3-amino-piperidin-1-yl group wherein the piperidin-1-yl-moiety is additionally substituted in the 4 position or in the 5 position by a hydroxy or methoxy group, a 3-amino-piperidin-1-yl group wherein the methylene group in 2 position or in 6 position is replaced by a carbonyl group, a piperidin-1-yl or hexahydroazepin-1-yl group substituted in the 3 position by an amino, $C_{1-3}$-alkylamino or di-($C_{1-3}$-alkyl)-amino group, wherein in each case two hydrogen atoms on the carbon skeleton of the piperidin-1-yl or hexahydroazepin-1-yl group are replaced by a straight-chain alkylene bridge, wherein this bridge contains 2 to 5 carbon atoms, if the two hydrogen atoms are located on the same carbon atom, or contains 1 to 4 carbon atoms if the hydrogen atoms are located on adjacent carbon atoms, or contains 1 to 4 carbon atoms, if the hydrogen atoms are located on carbon atoms which by are separated by one atom, or contains 1 to 3 carbon atoms if the two hydrogen atoms are located on carbon atoms which are separated by two atoms, an azetidin-1-yl, pyrrolidin-1-yl, piperidin-1-yl or hexahydroazepin-1-yl group which is substituted by an amino-$C_{1-3}$-alkyl, $C_{1-3}$-alkylamino-$C_{1-3}$-alkyl or a di-($C_{1-3}$-alkyl) amino-$C_{1-3}$-alkyl group, a piperazin-1-yl or [1,4]diazepan-1-yl group optionally substituted on the carbon skeleton by one or two $C_{1-3}$-alkyl groups, a 3-imino-piperazin-1-yl, 3-imino-[1,4]diazepan-1-yl or 5-imino-[1,4]diazepan-1-yl group optionally substituted on the carbon skeleton by one or two $C_{1-3}$-alkyl groups, a [1,4]diazepan-1-yl group optionally substituted by one or two $C_{1-3}$-alkyl groups, which is substituted by an amino group in the 6 position, a $C_{3-7}$-cycloalkyl group which is substituted by an amino, $C_{1-3}$-alkylamino or di-($C_{1-3}$-alkyl)-amino group, a $C_{3-7}$-cycloalkyl group which is substituted by an amino-$C_{1-3}$-alkyl, $C_{1-3}$-alkylamino-$C_{1-3}$-alkyl or a di-($C_{1-3}$-alkyl) amino-$C_{1-3}$-alkyl group, a $C_{3-7}$-cycloalkyl-$C_{1-2}$-alkyl group wherein the cycloalkyl moiety is substituted by an amino, $C_{1-3}$-alkylamino or di-($C_{1-3}$-alkyl)-amino group, a $C_{3-7}$-cycloalkyl-$C_{1-2}$-alkyl group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, a $C_{3-7}$-cycloalkylamino group wherein the cycloalkyl moiety is substituted by an amino, $C_{1-3}$-alkylamino or di-($C_{1-3}$-alkyl)-amino group, wherein the two nitrogen atoms on the cycloalkyl moiety are separated from one another by at least two carbon atoms, an N-($C_{3-7}$-cycloalkyl)-N-($C_{1-3}$-alkyl)-amino group wherein the cycloalkyl moiety is substituted by an amino, $C_{1-3}$-alkylamino or di-($C_{1-3}$-alkyl)-amino group, wherein the two nitrogen atoms on the cycloalkyl moiety are separated from one another by at least two carbon atoms, a $C_{3-7}$-cycloalkylamino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, an N-($C_{3-7}$-cycloalkyl)-N-($C_{1-3}$-alkyl)-amino group wherein the cycloalkyl moiety is substituted by an amino-$C_{1-3}$-alkyl, $C_{1-3}$-alkylamino-$C_{1-3}$-alkyl or a di-($C_{1-3}$-alkyl) amino-$C_{1-3}$-alkyl group, a $C_{3-7}$-cycloalkyl-$C_{1-2}$-alkyl-amino group wherein the cycloalkyl moiety is substituted by an amino, $C_{1-3}$-alkylamino or di-($C_{1-3}$-alkyl)-amino group, an N-($C_{3-7}$-cycloalkyl-$C_{1-2}$-alkyl)-N-($C_{1-2}$-alkyl)-amino group wherein the cycloalkyl moiety is substituted by an amino, $C_{1-3}$-alkylamino or di-($C_{1-3}$-alkyl)-amino group, a $C_{3-7}$-cycloalkyl-$C_{1-2}$-alkyl-amino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, an N-($C_{3-7}$-cycloalkyl-$C_{1-2}$-alkyl)-N-($C_{1-2}$-alkyl)-amino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, an $R^{19}$—$C_{2-4}$-alkylamino group wherein $R^{19}$ is separated from the nitrogen atom of the $C_{2-4}$-alkylamino moiety by at least two carbon atoms and $R^{19}$ denotes an amino, $C_{1-3}$-alkylamino or di-($C_{1-3}$-alkyl)-amino group, an $R^{19}$—$C_{2-4}$-alkylamino group wherein the nitrogen atom of the $C_{2-4}$-alkylamino moiety is substituted by a $C_{1-3}$-alkyl group and $R^{19}$ is separated from the nitrogen atom of the $C_{2-4}$-alkylamino moiety by at least two carbon atoms, wherein $R^{19}$ is as hereinbefore defined, an amino group substituted by the group R²⁰ wherein
R²⁰ denotes an azetidin-3-yl, azetidin-2-ylmethyl, azetidin-3-ylmethyl, pyrrolidin-3-yl, pyrrolidin-2-ylmethyl, pyrrolidin-3-ylmethyl, piperidin-3-yl, piperidin-4-yl, piperidin-2-ylmethyl, piperidin-3-ylmethyl or piperidin-4-ylmethyl group, wherein the groups mentioned for R²⁰ may each be substituted by one or two $C_{1-3}$-alkyl groups, an amino group substituted by the group R²⁰ and a $C_{1-3}$-alkyl group wherein R²⁰ is as hereinbefore defined, wherein the groups mentioned for R²⁰ may each be substituted by one or two $C_{1-3}$-alkyl groups, a R¹⁹—$C_{3-4}$-alkyl group wherein the $C_{3-4}$-alkyl moiety is straight-chain and may additionally be substituted by one or two $C_{1-3}$-alkyl groups, wherein R¹⁹ is as hereinbefore defined, a 3-amino-2-oxo-piperidin-5-yl or 3-amino-2-oxo-1-methyl-piperidin-5-yl group, a pyrrolidin-3-yl, piperidin-3-yl, piperidin-4-yl, hexahydroazepin-3-yl or hexahydroazepin-4-yl group which is substituted in the 1 position by an amino, $C_{1-3}$-alkylamino or di-($C_{1-3}$-alkyl)amino group, or an azetidin-2-yl-$C_{1-2}$-alkyl, azetidin-3-yl-$C_{1-2}$-alkyl, pyrrolidin-2-yl-$C_{1-2}$-alkyl, pyrrolidin-3-yl, pyrrolidin-3-yl-$C_{1-2}$-alkyl, piperidin-2-yl-$C_{1-2}$-alkyl, piperidin-3-yl, piperidin-3-yl-$C_{1-2}$-alkyl, piperidin-4-yl or piperidin-4-yl-$C_{1-2}$-alkyl group, wherein the above-mentioned groups may each be substituted by one or two $C_{1-3}$-alkyl groups, wherein by the aryl groups mentioned in the definition of the above groups are meant phenyl or naphthyl groups, which may be mono- or disubstituted by $R_h$ independently of one another, where the substituents are identical or different and $R_h$ denotes a fluorine, chlorine, bromine or iodine atom, a trifluoromethyl, cyano, nitro, amino, aminocarbonyl, aminosulphonyl, methylsulphonyl, acetylamino, methylsulphonylamino, $C_{1-3}$-alkyl, cyclopropyl, ethenyl, ethynyl, hydroxy, $C_{1-3}$-alkyloxy, difluoromethoxy or trifluoromethoxy group, by the heteroaryl groups mentioned in the definitions of the above mentioned groups are meant a pyrrolyl, furanyl, thienyl, pyridyl, indolyl, benzofuranyl, benzothiophenyl, quinolinyl or isoquinolinyl group, or a pyrrolyl, furanyl, thienyl or pyridyl group wherein one or two methyne groups are replaced by nitrogen atoms, or an indolyl, benzofuranyl, benzothiophenyl, quinolinyl or isoquinolinyl group wherein one to three methyne groups are replaced by nitrogen atoms, and the above-mentioned heteroaryl groups may be mono- or disubstituted by $R_h$, wherein the substituents may be identical or different and $R_h$ is as hereinbefore defined, and, unless otherwise specified, the above-mentioned alkyl, alkenyl and alkynyl groups may be straight-chain or branched, the tautomers, enantiomers, diastereomers, the mixtures thereof, the prodrugs thereof and the salts thereof.

Compounds of the above general formula I which contain one or more groups that can be cleaved in vivo are so-called prodrugs.

The carboxy groups mentioned in the definition of the above mentioned groups may be replaced by a group which can be converted into a carboxy group in vivo or by a group which is negatively charged under physiological conditions, and furthermore the amino and imino groups mentioned in the definition of the above mentioned groups may be substituted by a group which can be cleaved in vivo. Such groups are described for example in WO 98/46576 and by N. M. Nielsen et al. in International Journal of Pharmaceutics 39, 75-85 (1987).

By a group which can be converted in vivo into a carboxy group is meant, for example, a hydroxymethyl group, a carboxy group esterified with an alcohol wherein the alcohol moiety is preferably a $C_{1-6}$-alkanol, a phenyl-$C_{1-3}$-alkanol, a $C_{3-9}$-cycloalkanol, wherein a $C_{5-8}$-cycloalkanol may additionally be substituted by one or two $C_{1-3}$-alkyl groups, a $C_{5-8}$-cycloalkanol wherein a methylene group in the 3 or 4 position is replaced by an oxygen atom or by an imino group optionally substituted by a $C_{1-3}$-alkyl, phenyl-$C_{1-3}$-alkyl, phenyl-$C_{1-3}$-alkyloxycarbonyl or $C_{2-6}$-alkanoyl group and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol or phenyl-$C_{3-5}$-alkynol with the proviso that no bonds to the oxygen atom start from a carbon atom which carries a double or triple bond, a $C_{3-8}$-cycloalkyl-$C_{1-3}$-alkanol, a bicycloalkanol with a total of 8 to 10 carbon atoms which may additionally be substituted in the bicycloalkyl moiety by one or two $C_{1-3}$-alkyl groups, a 1,3-dihydro-3-oxo-1-isobenzofuranol or an alcohol of formula

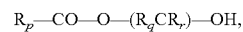

wherein $R_p$ denotes a $C_{1-8}$-alkyl, $C_{5-7}$-cycloalkyl, $C_{1-8}$-alkyloxy, $C_{5-7}$-cycloalkyloxy, phenyl or phenyl-$C_{1-3}$-alkyl group, $R_q$ denotes a hydrogen atom, a $C_{1-3}$-alkyl, $C_{5-7}$-cycloalkyl or phenyl group and $R_r$ denotes a hydrogen atom or a $C_{1-3}$-alkyl group, by a group which is negatively charged under physiological conditions is meant, for example, a tetrazol-5-yl, phenylcarbonylaminocarbonyl, trifluoromethylcarbonylaminocarbonyl, $C_{1-6}$-alkylsulphonylamino, phenylsulphonylamino, benzylsulphonylamino, trifluoromethylsulphonylamino, $C_{1-6}$-alkylsulphonylaminocarbonyl, phenylsulphonylaminocarbonyl, benzylsulphonylaminocarbonyl or perfluoro-$C_{1-6}$-alkylsulphonylaminocarbonyl group and by a group which can be cleaved in vivo from an imino or amino group is meant, for example, a hydroxy group, an acyl group such as a phenylcarbonyl group optionally mono- or disubstituted by fluorine, chlorine, bromine or iodine atoms, by $C_{1-3}$-alkyl or $C_{1-3}$-alkyloxy groups, wherein the substituents may be identical or different, a pyridinoyl group or a $C_{1-16}$-alkanoyl group such as the formyl, acetyl, propionyl, butanoyl, pentanoyl or hexanoyl group, a 3,3,3-trichloropropionyl or allyloxycarbonyl group, a $C_{1-16}$-alkyloxycarbonyl or $C_{1-16}$-alkylcarbonyloxy group, wherein hydrogen atoms may be wholly or partially replaced by fluorine or chlorine atoms such as the methoxycarbonyl, ethoxycarbonyl, propoxycarbonyl, isopropoxycarbonyl, butoxycarbonyl, tert.butoxycarbonyl, pentoxycarbonyl, hexoxycarbonyl, octyloxycarbonyl, nonyloxycarbonyl, decyloxycarbonyl, undecyloxycarbonyl, dodecyloxycarbonyl, hexadecyloxycarbonyl, methylcarbonyloxy, ethylcarbonyloxy, 2,2,2-trichloroethylcarbonyloxy, propylcarbonyloxy, isopropylcarbonyloxy, butylcarbonyloxy, tert.butylcarbonyloxy, pentylcarbonyloxy, hexylcarbonyloxy, octylcarbonyloxy, nonylcarbonyloxy, decylcarbonyloxy, undecylcarbonyloxy, dodecylcarbonyloxy or hexadecylcarbonyloxy group, a phenyl-$C_{1-6}$-alkyloxycarbonyl group such as the benzyloxycarbonyl, phenylethoxycarbonyl or phenylpropoxycarbonyl group, a 3-amino-propionyl group wherein the amino group may be mono- or disubstituted by $C_{1-6}$-alkyl or $C_{3-7}$-cycloalkyl groups and the substituents may be identical or different, a $C_{1-3}$-alkylsulphonyl-$C_{2-4}$-alkyloxycarbonyl, $C_{1-3}$-alkyloxy-$C_{2-4}$-alkyloxy-$C_{2-4}$-alkyloxycarbonyl, $R_p$—CO—O—$(R_qCR_r)$—O—CO, $C_{1-6}$-alkyl-CO—NH—$(R_sCR_t)$—O—CO or $C_{1-6}$-alkyl-CO—O—$(R_sCR_t)$—$(R_sCR_t)$—O—CO group, wherein $R_p$ to $R_r$ are as hereinbefore defined, $R_s$ and $R_t$, which may be identical or different, denote hydrogen atoms or $C_{1-3}$-alkyl groups.

Moreover, the saturated alkyl and alkyloxy moieties which contain more than 2 carbon atoms mentioned in the foregoing definitions and those that follow, unless otherwise stated, also include the branched isomers thereof such as, for example, the isopropyl, tert.butyl, isobutyl group, etc.

$R^2$ for example in each case denotes a hydrogen atom, a methyl, ethyl, propyl, 2-propyl, butyl, 2-butyl, 2-methylpropyl, 2-propen-1-yl, 2-propyn-1-yl, cyclopropylmethyl, benzyl, 2-phenylethyl, phenylcarbonylmethyl, 3-phenylpropyl, 2-hydroxyethyl, 2-methoxyethyl, 2-ethoxyethyl, 2-(dimethylamino)ethyl, 2-(diethylamino)ethyl, 2-(pyrrolidino)ethyl, 2-(piperidino)ethyl, 2-(morpholino)ethyl, 2-(piperazino)ethyl, 2-(4-methylpiperazino)ethyl, 3-hydroxypropyl, 3-methoxypropyl, 3-ethoxypropyl, 3-(dimethylamino)propyl, 3-(diethylamino)propyl, 3-(pyrrolidino)propyl, 3-(piperidino)propyl, 3-(morpholino)propyl, 3-(piperazino)propyl, 3-(4-methylpiperazino)propyl, carboxymethyl, (methoxycarbonyl)methyl, (ethoxycarbonyl)methyl, 2-carboxyethyl, 2-(methoxycarbonyl)ethyl, 2-(ethoxycarbonyl)ethyl, 3-carboxypropyl, 3-(methoxycarbonyl)propyl, 3-(ethoxycarbonyl)propyl, (aminocarbonyl)methyl, (methylaminocarbonyl)methyl, (dimethylaminocarbonyl)methyl, (pyrrolidinocarbonyl)methyl, (piperidinocarbonyl)methyl, (morpholinocarbonyl)-methyl, 2-(aminocarbonyl)ethyl, 2-(methylaminocarbonyl)ethyl, 2-(dimethylaminocarbonyl)ethyl, 2-(pyrrolidinocarbonyl)ethyl, 2-(piperidino-carbonyl)ethyl, 2-(morpholinocarbonyl)ethyl, cyanomethyl or 2-cyanoethyl group.

$R^3$ for example may denote a methyl, ethyl, propyl, 2-propyl, butyl, 2-butyl, 2-methylpropyl, pentyl, 2-methylbutyl, 3-methylbutyl, 2,2-dimethylpropyl, cyclopropylmethyl, (1-methylcyclopropyl)methyl, (2-methylcyclopropyl)methyl, cyclobutylmethyl, cyclopentylmethyl, cyclohexylmethyl, 2-(cyclopropyl)ethyl-, 2-propen-1-yl, 2-methyl-2-propen-1-yl, 3-phenyl-2-propen-1-yl, 2-buten-1-yl, 4,4,4-trifluoro-2-buten-1-yl, 3-buten-1-yl, 2-chloro-2-buten-1-yl, 2-bromo-2-buten-1-yl, 3-chloro-2-buten-1-yl, 3-bromo-2-buten-1-yl, 2-methyl-2-buten-1-yl, 3-methyl-2-buten-1-yl, 2,3-dimethyl-2-buten-1-yl, 3-trifluoromethyl-2-buten-1-yl, 3-methyl-3-buten-1-yl, 1-cyclopenten-1-ylmethyl, (2-methyl-1-cyclopenten-1-yl)methyl, 1-cyclohexen-1-ylmethyl, 2-(1-cyclopenten-1-yl)ethyl, 2-propyn-1-yl, 2-butyn-1-yl, 3-butyn-1-yl, phenyl, methylphenyl, benzyl, a fluorobenzyl, chlorobenzyl, bromobenzyl, methylbenzyl, methoxybenzyl, 1-phenylethyl, 2-phenylethyl, 3-phenylpropyl, 2-furanylmethyl, 3-furanylmethyl, 2-thienylmethyl or 3-thienylmethyl group.

$R^4$ for example may denote a 3-aminopyrrolidin-1-yl, 3-aminopiperidin-1-yl, 3-(methylamino)-piperidin-1-yl, 3-(ethylamino)-piperidin-1-yl, 3-(dimethylamino)-piperidin-1-yl, 3-(diethylamino)-piperidin-1-yl, 3-[(2-hydroxyethyl)amino]-piperidin-1-yl, 3-[N-methyl-N-(2-hydroxyethyl)-amino]-piperidin-1-yl, 3-[(3-hydroxypropyl)amino]-piperidin-1-yl, 3-[N-methyl-N-(3-hydroxypropyl)-amino]-piperidin-1-yl, 3-[(carboxymethyl)amino]-piperidin-1-yl, 3-[(methoxycarbonylmethyl)amino]-piperidin-1-yl, 3-[(ethoxycarbonylmethyl)amino]-piperidin-1-yl, 3-[N-methyl-N-(methoxycarbonylmethyl)-amino]-piperidin-1-yl, 3-[N-methyl-N-(ethoxycarbonylmethyl)-amino]-piperidin-1-yl, 3-[(2-carboxyethyl)amino]-piperidin-1-yl, 3-{[2-(methoxycarbonyl)ethyl]amino}-piperidin-1-yl, 3-{[2-(ethoxycarbonyl)ethyl]amino}-piperidin-1-yl, 3-{N-methyl-N-[2-(methoxycarbonyl)ethyl]-amino}-piperidin-1-yl, 3-{N-methyl-N-[2-(ethoxycarbonyl)ethyl]-amino}-piperidin-1-yl, 3-[(aminocarbonylmethyl)amino]-piperidin-1-yl, 3-[(methylaminocarbonylmethyl)amino]-piperidin-1-yl, 3-[(dimethylaminocarbonylmethyl)amino]-piperidin-1-yl, 3-[(ethylaminocarbonylmethyl)amino]-piperidin-1-yl, 3-[(diethylaminocarbonylmethyl)amino]-piperidin-1-yl, 3-[(pyrrolidin-1-ylcarbonylmethyl)amino]-piperidin-1-yl, 3-[(2-cyanopyrrolidin-1-ylcarbonylmethyl)amino]-piperidin-1-yl, 3-[(4-cyanothiazolidin-3-ylcarbonylmethyl)amino]-piperidin-1-yl, 3-[(2-aminocarbonylpyrrolidin-1-ylcarbonylmethyl)amino]-piperidin-1-yl, 3-[(2-carboxypyrrolidin-1-ylcarbonylmethyl)amino]-piperidin-1-yl, 3-[(2-methoxycarbonylpyrrolidin-1-ylcarbonylmethyl)amino]-piperidin-1-yl, 3-[(2-ethoxycarbonylpyrrolidin-1-ylcarbonylmethyl)amino]-piperidin-1-yl, 3-[(piperidin-1-ylcarbonylmethyl)amino]-piperidin-1-yl, 3-[(morpholin-4-ylcarbonylmethyl)amino]-piperidin-1-yl, 3-amino-2-methyl-piperidin-1-yl, 3-amino-3-methyl-piperidin-1-yl, 3-amino-4-methyl-piperidin-1-yl, 3-amino-5-methyl-piperidin-1-yl, 3-amino-6-methyl-piperidin-1-yl, 2-amino-8-azabicyclo[3.2.1]oct-8-yl, 6-amino-2-aza-bicyclo[2.2.2]oct-2-yl, 4-aminopiperidin-1-yl, 3-amino-hexahydroazepin-1-yl, 4-amino-hexahydroazepin-1-yl, piperazin-1-yl, [1,4]diazepan-1-yl, 3-aminocyclopentyl, 3-aminocyclohexyl, 3-(methylamino)-cyclohexyl, 3-(ethylamino)-cyclohexyl, 3-(dimethylamino)-cyclohexyl, 3-(diethylamino)-cyclohexyl, 4-aminocyclohexyl, (2-aminocyclopropyl)amino, (2-aminocyclobutyl)amino, (3-aminocyclobutyl)amino, (2-aminocyclopentyl)amino, (3-amino-cyclopentyl)amino, (2-aminocyclohexyl)amino or (3-aminocyclohexyl)amino group.

Preferred compounds of the above general formula I are those wherein $R^1$ denotes a methyl group substituted by a group $R_a$, where
    $R_a$ denotes a 1,4-dihydro-quinazolinyl or 3,4-dihydro-quinazolinyl group,
    a 3,4-dihydro-isoquinolinyl group,
    a 1H-benzo[d][1,2]oxazinyl or 1-oxo-1H-benzo[d][1,2]oxazinyl group,
    a 4H-benzo[e][1,3]oxazinyl or 4-oxo-4H-benzo[e][1,3]oxazinyl group,
    a 4H-benzo[d][1,3]oxazinyl or 4-oxo-4H-benzo[d][1,3]oxazinyl group,
    2H-benzo[1,4]oxazinyl or 2-oxo-2H-benzo[1,4]oxazinyl group,
    a 4H-benzo[e][1,3]thiazinyl or 4-oxo-4H-benzo[e][1,3]thiazinyl group,
    a 4H-benzo[d][1,3]thiazinyl or 2H-benzo[1,4]thiazinyl group,
    a 2-oxo-2H-benzo[e][1,3]oxazinyl or 2,2-dioxo-1H-benzo[c][1,2]thiazinyl group,
    a 2,3-dihydro-1H-benzo[e][1,4]diazepinyl or 2-oxo-2,3-dihydro-1H-benzo[e][1,4]diazepinyl group,
    a 4,5-dihydro-3H-benzo[b][1,4]diazepinyl or 4-oxo-4,5-dihydro-3H-benzo[b][1,4]diazepinyl group,
    a 5-oxo-4,5-dihydro-3H-benzo[e][1,4]diazepinyl group,
    a 2,3-dihydro-benzo[f][1,4]oxazepinyl or 2,3-dihydro-benzo[b][1,4]oxazepinyl group,
    a 2,3-dihydro-benzo[f][1,4]thiazepinyl-2,3-dihydro-benzo[b][1,4]thiazepinyl group,
    a 5-oxo-4,5-dihydro-benzo[f][1,3,4]oxadiazepinyl group,
    an 11H-dibenzo[b,e]azepinyl or 11-oxo-11H-dibenzo[b,e]azepinyl group, an 11H-benzo[e]pyrido[3,2-b]azepinyl group,
a 5H-dibenzo[b,e][1,4]diazepinyl or dibenzo[b,f][1,4]oxazepinyl group,
a dibenzo[b,f][1,4]thiazepinyl, 5-oxo-dibenzo[b,f][1,4]thiazepinyl or 5,5-dioxo-dibenzo[b,f][1,4]thiazepinyl group, 5H-dibenzo[a,d]cycloheptenyl or 5H-dibenzo[b,f]azepinyl group,
a phenanthridinyl, benzo[c][1,5]naphthyridinyl, benzo[h][1,6]naphthyridinyl, benzo[c][1,8]naphthyridinyl or 1,2,3,4-tetrahydro-phenanthridinyl group,
a benzo[f]quinoxalinyl group,
a 5H-dibenzo[d,f][1,3]diazepinyl, 5H-benzo[e]pyrrolo[1,2-a][1,4]diazepinyl or thieno[3,2-b][1,4]benzoxazepinyl group,
a 3-oxo-2,3-dihydro-isoindol-1-ylidene group,
a benzo[1,2,5]oxadiazolyl group,
a dibenzofuranyl group,
an indolizinyl group,
a 1H-perimidinyl group,
a pyrazolo[1,5-c]quinazolinyl group or
an imidazo[2,1-a]isoquinolinyl or imidazo[1,2-a]isoquinolinyl group
wherein the benzo groups of the above-mentioned groups $R_a$ are substituted by the groups $R^{10}$ to $R^{12}$ and the alkylene units of the above-mentioned groups $R_a$ may be substituted by one or two $C_{1-3}$-alkyl or $C_{1-3}$-alkyloxy-carbonyl groups, wherein the groups may be identical or different, or by a trifluoromethyl group, and the imino groups of the above-mentioned groups $R_a$ may be substituted by a $C_{1-3}$-alkyl group and
$R^{10}$ denotes a hydrogen atom,
a fluorine, chlorine, bromine or iodine atom,
a $C_{1-3}$-alkyl or cyclopropyl group,
a hydroxy, $C_{1-3}$-alkyloxy or cyclopropyloxy group,
a nitro, amino, $C_{1-3}$-alkylamino or di-($C_{1-3}$-alkyl)amino group,
a $C_{1-3}$-alkyl-carbonylamino or $C_{1-3}$-alkyl-sulphonylamino group,
a cyano, carboxy, $C_{1-3}$-alkyloxy-carbonyl, aminocarbonyl, $C_{1-3}$-alkyl-aminocarbonyl or di-($C_{1-3}$-alkyl)-aminocarbonyl group,
a mercapto, $C_{1-3}$-alkylsulphanyl, $C_{1-3}$-alkylsulphinyl or $C_{1-3}$-alkylsulphonyl or aminosulphonyl group or
a difluoromethyl, trifluoromethyl, difluoromethoxy or trifluoromethoxy group and
$R^{11}$ and $R^{12}$, which may be identical or different, in each case represent a hydrogen atom, a fluorine, chlorine or bromine atom, a methyl, trifluoromethyl or methoxy group,
$R^2$ denotes a hydrogen atom,
a $C_{1-3}$-alkyl group,
a $C_{3-6}$-cycloalkyl group or
a phenyl group optionally mono- or disubstituted by a fluorine, chlorine, bromine or iodine atom, a trifluoromethyl, cyano, nitro, amino, aminocarbonyl, aminosulphonyl, methylsulphonyl, acetylamino, methylsulphonylamino, $C_{1-3}$-alkyl, cyclopropyl, ethenyl, ethynyl, hydroxy, $C_{1-3}$-alkyloxy, difluoromethoxy or trifluoromethoxy group, wherein the substituents may be identical or different,
$R^3$ denotes a 2-buten-1-yl or 3-methyl-2-buten-1-yl group,
a 2-butyn-1-yl group or
a 1-cyclopenten-1-ylmethyl group and
$R^4$ denotes a (3-amino-piperidin-1-yl) group,
wherein, unless otherwise stated, the above-mentioned alkyl groups may be straight-chain or branched,
the tautomers, enantiomers, diastereomers, the mixtures thereof and the salts thereof.

Particularly preferred compounds of the above general formula I are those wherein
$R^1$ denotes a methyl group substituted by a group $R_a$, where
$R_a$ denotes a 1,4-dihydro-quinazolin-2-yl or 3,4-dihydro-quinazolin-2-yl group,
a 3,4-dihydro-isoquinolin-1-yl group,
a 1H-benzo[d][1,2]oxazin-4-yl or 1-oxo-1H-benzo[d][1,2]oxazin-4-yl group,
a 4H-benzo[e][1,3]oxazin-2-yl or 4-oxo-4H-benzo[e][1,3]oxazin-2-yl group,
a 4H-benzo[d][1,3]oxazin-2-yl or 4-oxo-4H-benzo[d][1,3]oxazin-2-yl group,
2H-benzo[1,4]oxazin-3-yl or 2-oxo-2H-benzo[1,4]oxazin-3-yl group,
a 4H-benzo[e][1,3]thiazin-2-yl or 4-oxo-4H-benzo[e][1,3]thiazin-2-yl group,
a 4H-benzo[d][1,3]thiazin-2-yl or 2H-benzo[1,4]thiazin-3-yl group,
a 2-oxo-2H-benzo[e][1,3]oxazin-4-yl or 2,2-dioxo-1H-benzo[c][1,2]thiazin-4-yl group,
a 2,3-dihydro-1H-benzo[e][1,4]diazepin-5-yl or 2-oxo-2,3-dihydro-1H-benzo[e][1,4]diazepin-5-yl group,
a 4,5-dihydro-3H-benzo[b][1,4]diazepin-2-yl or 4-oxo-4,5-dihydro-3H-benzo[b][1,4]diazepin-2-yl group,
a 5-oxo-4,5-dihydro-3H-benzo[e][1,4]diazepin-2-yl group,
a 2,3-dihydro-benzo[f][1,4]oxazepin-5-yl or 2,3-dihydro-benzo[b]-[1,4]oxazepin-4-yl group,
a 2,3-dihydro-benzo[f][1,4]thiazepin-5-yl or 2,3-dihydro-benzo[b]-[1,4]thiazepin-4-yl group,
a 5-oxo-4,5-dihydro-benzo[f][1,3,4]oxadiazepin-2-yl group,
an 11H-dibenzo[b,e]azepin-6-yl or 11-oxo-11H-dibenzo[b,e]azepin-6-yl group,
an 11H-benzo[e]pyrido[3,2-b]azepin-6-yl group
a 5H-dibenzo[b,e][1,4]diazepin-11-yl or dibenzo[b,f][1,4]oxazepin-11-yl group,
a dibenzo[b,f][1,4]thiazepin-11-yl, 5-oxo-dibenzo[b,f][1,4]thiazepin-11-yl or 5,5-dioxo-dibenzo[b,f][1,4]thiazepin-11-yl group,
a 5H-dibenzo[a,d]cyclohepten-10-yl or 5H-dibenzo[b,f]azepin-10-yl group,
a phenanthridin-6-yl, benzo[c][1,5]naphthyridin-6-yl, benzo[h][1,6]naphthyridin-5-yl, benzo[c][1,8]naphthyridin-6-yl or 1,2,3,4-tetrahydrophenanthridin-6-yl group,
a benzo[f]quinoxalin-6-yl group,
a 5H-dibenzo[d,t][1,3]diazepin-6-yl, 5H-benzo[e]pyrrolo[1,2-a][1,4]diazepin-11-yl or thieno[3,2-b][1,4]benzoxazepinyl-9-yl group,
a 3-oxo-2,3-dihydro-isoindol-1-ylidene group,
a benzo[1,2,5]oxadiazol-5-yl group,
a dibenzofuran-2-yl group,
an indolizin-2-yl group,
a 1H-perimidin-2-yl group,
a pyrazolo[1,5-c]quinazolin-5-yl group or
an imidazo[2,1-a]isoquinolin-2-yl or imidazo[1,2-a]isoquinolin-2-yl group
wherein the benzo groups of the above-mentioned groups $R_a$ are substituted by the groups $R^{10}$ to $R^{12}$ and the alkylene units of the above-mentioned groups $R_a$ may be substituted by one or two methyl- or methoxy-carbonyl groups, wherein the groups may be identical or different, or by a trifluoromethyl group and the imino groups of the above-mentioned groups $R_a$ may be substituted by a methyl group and R$^{10}$ denotes a hydrogen atom,
a fluorine, chlorine, bromine or iodine atom,
a methyl or ethyl group,
a hydroxy, methoxy or ethoxy group or
a difluoromethyl, trifluoromethyl, difluoromethoxy or trifluoromethoxy group and
R$^{11}$ and R$^{12}$, which may be identical or different, each represent a hydrogen atom, a fluorine, chlorine or bromine atom, a methyl, trifluoromethyl or methoxy group,
R$^2$ denotes a hydrogen atom or
a methyl, ethyl, propyl, isopropyl, phenyl or cyclopropyl group,
R$^3$ denotes a 2-buten-1-yl or 3-methyl-2-buten-1-yl group,
a 2-butyn-1-yl group or
a 1-cyclopenten-1-ylmethyl group and
R$^4$ denotes a (3-amino-piperidin-1-yl) group,
the tautomers, enantiomers, diastereomers, the mixtures thereof and the salts thereof.

Most particularly preferred compounds of the above general formula I are those wherein
R$^1$ denotes a 3-methoxycarbonyl-3-methyl-3,4-dihydro-isoquinolin-1-ylmethyl group,
a 1-methyl-2,2-dioxo-1H-benzo[c][1,2]thiazin-4-ylmethyl group,
a 2,3-dihydro-benzo[f][1,4]oxazepin-5-ylmethyl group,
a 2-oxo-2,3-dihydro-1H-benzo[e][1,4]diazepin-5-ylmethyl group,
a phenanthridin-6-ylmethyl or 1,2,3,4-tetrahydro-phenanthridin-6-ylmethyl group,
an 11H-dibenzo[b,e]azepin-6-ylmethyl group,
a dibenzo[b,f][1,4]oxazepin-11-ylmethyl group,
a 3-oxo-2,3-dihydro-isoindol-1-ylidenemethyl group,
a 3-trifluoromethyl-3,4-dihydro-isoquinolin-1-ylmethyl group,
a 3,4-dihydro-quinazolin-2-ylmethyl group,
a 5-methyl-5H-dibenzo[b,e][1,4]diazepin-11-ylmethyl group,
an 8-methyl-dibenzo[b,f][1,4]oxazepin-11-ylmethyl group,
a benzo[1,2,5]oxadiazol-5-ylmethyl group,
an 8-methyl-phenanthridin-6-ylmethyl group,
a 1-methyl-phenanthridin-6-ylmethyl group,
a 4-methyl-phenanthridin-6-ylmethyl group,
a benzo[h][1,6]naphthyridin-5-ylmethyl group,
a pyrazolo[1,5-c]quinazolin-5-yl group,
a benzo[c][1,8]naphthyridin-6-ylmethyl group,
a benzo[c][1,5]naphthyridin-6-ylmethyl group,
a 1H-perimidin-2-ylmethyl group,
a benzo[f]quinoxalin-6-ylmethyl group or
an imidazo[2,1-a]isoquinolin-2-ylmethyl or imidazo[1,2-a]isoquinolin-2-ylmethyl group,
R$^2$ denotes a methyl or cyclopropyl group,
R$^3$ denotes a 2-buten-1-yl, 3-methyl-2-buten-1-yl or 2-butyn-1-yl group and
R$^4$ denotes a (3-amino-piperidin-1-yl) group,
the tautomers, enantiomers, diastereomers, the mixtures thereof and the salts thereof.

The following compounds of general formula I are particularly preferred:
(1) 1-[(1-methyl-2,2-dioxo-1H-benzo[c][1,2]thiazin-4-yl)methyl]-3-methyl-7-(3-methyl-2-buten-1-yl)-8-(3-amino-piperidin-1-yl)-xanthine,
(2) 1-[(3-methoxycarbonyl-3-methyl-3,4-dihydro-isoquinolin-1-yl]methyl]-3-methyl-7-(2-butyn-1-yl)-8-(3-amino-piperidin-1-yl)-xanthine,
(3) 1-[(2-oxo-2,3-dihydro-1H-benzo[e][1,4]diazepin-5-yl)methyl]-3-methyl-7-((E)-2-buten-1-yl)-8-((R)-3-amino-piperidin-1-yl)-xanthine,
(4) 1-[(phenanthridin-6-yl)methyl]-3-methyl-7-(2-butyn-1-yl)-8-(3-aminopiperidin-1-yl)-xanthine,
(5) 1-[(1,2,3,4-tetrahydro-phenanthridin-6-yl)methyl]-3-methyl-7-(2-butyn-1-yl)-8-(3-amino-piperidin-1-yl)-xanthine,
(6) 1-[(11H-dibenzo[b,e]azepin-6-yl)methyl]-3-methyl-7-(2-butyn-1-yl)-8-(3-amino-piperidin-1-yl)-xanthine,
(7) 1-[(dibenzo[b,f][1,4]oxazepin-11-yl)methyl]-3-methyl-7-(2-butyn-1-yl)-8-(3-amino-piperidin-1-yl)-xanthine,
(8) 1-[(3-trifluoromethyl-3,4-dihydro-isoquinolin-1-yl)methyl]-3-methyl-7-(2-butyn-1-yl)-8-(3-amino-piperidin-1-yl)-xanthine,
(9) 1-[(dibenzo[b,f][1,4]oxazepin-11-yl)methyl]-3-methyl-7-(2-butyn-1-yl)-8-((R)-3-amino-piperidin-1-yl)-xanthine,
(10) 1-[(3,4-dihydro-quinazolin-2-yl)methyl]-3-methyl-7-(2-butyn-1-yl)-8-(3-amino-piperidin-1-yl)-xanthine,
(11) 1-[(5-methyl-5H-dibenzo[b,e][1,4]diazepin-11-yl)methyl]-3-methyl-7-(2-butyn-1-yl)-8-(3-amino-piperidin-1-yl)-xanthine,
(12) 1-[(8-methyl-dibenzo[b,f][1,4]oxazepin-11-yl)methyl]-3-methyl-7-(2-butyn-1-yl)-8-(3-amino-piperidin-1-yl)-xanthine,
(13) 1-[(benzo[1,2,5]oxadiazol-5-yl)methyl]-3-methyl-7-(2-butyn-1-yl)-8-(3-amino-piperidin-1-yl)-xanthine,
(14) 1-[(phenanthridin-6-yl)methyl]-3-cyclopropyl-7-(2-butyn-1-yl)-8-(3-aminopiperidin-1-yl)-xanthine,
(15) 1-[(8-methyl-phenanthridin-6-yl)methyl]-3-methyl-7-(2-butyn-1-yl)-8-(3-amino-piperidin-1-yl)-xanthine,
(16) 1-[(phenanthridin-6-yl)methyl]-3-methyl-7-(2-butyn-1-yl)-8-((S)-3-aminopiperidin-1-yl)-xanthine,
(17) 1-[(phenanthridin-6-yl)methyl]-3-cyclopropyl-7-(2-butyn-1-yl)-8-((R)-3-amino-piperidin-1-yl)-xanthine,
(18) 1-[(1-methyl-phenanthridin-6-yl)methyl]-3-methyl-7-(2-butyn-1-yl)-8-((R)-3-amino-piperidin-1-yl)-xanthine,
(19) 1-[(4-methyl-phenanthridin-6-yl)methyl]-3-methyl-7-(2-butyn-1-yl)-8-((R)-3-amino-piperidin-1-yl)-xanthine,
(20) 1-[(benzo[h][1,6]naphthyridin-5-yl)methyl]-3-methyl-7-(2-butyn-1-yl)-8-(3-amino-piperidin-1-yl)-xanthine,
(21) 1-[(pyrazolo[1,5-c]quinazolin-5-yl)methyl]-3-methyl-7-(2-butyn-1-yl)-8-(3-amino-piperidin-1-yl)-xanthine,
(22) 1-[(benzo[c][1,8]naphthyridin-6-yl)methyl]-3-methyl-7-(2-butyn-1-yl)-8-(3-amino-piperidin-1-yl)-xanthine,
(23) 1-[(benzo[c][1,5]naphthyridin-6-yl)methyl]-3-methyl-7-(2-butyn-1-yl)-8-((R)-3-amino-piperidin-1-yl)-xanthine,
(24) 1-[(1H-perimidin-2-yl)methyl]-3-methyl-7-(2-butyn-1-yl)-8-((R)-3-aminopiperidin-1-yl)-xanthine,
(25) 1-[(benzo[f]quinoxalin-6-yl)methyl]-3-methyl-7-(2-butyn-1-yl)-8-((R)-3-amino-piperidin-1-yl)-xanthine,
(26) 1-[(imidazo[2,1-a]isoquinolin-2-yl)methyl]-3-methyl-7-(2-butyn-1-yl)-8-(3-amino-piperidin-1-yl)-xanthine,
(27) 1-[(imidazo[1,2-a]isoquinolin-2-yl)methyl]-3-methyl-7-(2-butyn-1-yl)-8-(3-amino-piperidin-1-yl)-xanthine,
(28) 1-[(phenanthridin-6-yl)methyl]-3-methyl-7-(2-butyn-1-yl)-8-((R)-3-amino-piperidin-1-yl)-xanthine,
(29) 1-[(2,3-dihydro-benzo[f][1,4]oxazepin-5-yl)methyl]-3-methyl-7-(2-butyn-1-yl)-8-(3-amino-piperidin-1-yl)-xanthine and
(30) 1-[(3-oxo-2,3-dihydro-isoindol-1-ylidene)methyl]-3-methyl-7-(3-methyl-2-buten-1-yl)-8-(3-amino-piperidin-1-yl)-xanthine
and the salts thereof.

According to the invention the compounds of general formula I are obtained by methods known per se, for example by the following methods:

a) Deprotecting a Compound of General Formula

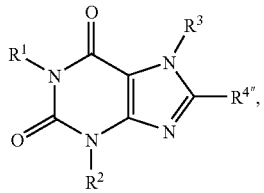

(II)

wherein $R^1$, $R^2$ and $R^3$ are as hereinbefore defined and $R^{4'}$ denotes one of the groups mentioned for $R^4$ hereinbefore which contain an imino, amino or alkylamino group, wherein the imino, amino or alkylamino group is substituted by a protective group.

The liberating of an amino group from a protected precursor is a standard reaction in synthetic organic chemistry. There are many examples of suitable protective groups. A summary of the chemistry of protective groups can be found in Theodora W. Greene and Peter G. M. Wuts, Protective Groups in Organic Synthesis, Second Edition, 1991, published by John Wiley and Sons, and in Philip J. Kocienski, Protecting Groups, published by Georg Thieme, 1994.

The following are examples of protective groups:
the tert.-butyloxycarbonyl group which can be cleaved by treating with an acid such as for example trifluoroacetic acid or hydrochloric acid or by treating with bromotrimethylsilane or iodotrimethylsilane, optionally using a solvent such as methylene chloride, ethyl acetate, dioxane, methanol, isopropanol or diethylether at temperatures between 0° C. and 80° C.,
the 2,2,2-trichloroethoxycarbonyl group which can be cleaved by treating with metals such as for example zinc or cadmium in a solvent such as acetic acid or a mixture of tetrahydrofuran and a weak aqueous acid at temperatures between 0° C. and the boiling temperature of the solvent used and
the carbobenzyloxycarbonyl group which can be cleaved for example by hydrogenolysis in the presence of a noble metal catalyst such as for example palladium-charcoal and a solvent such as for example alcohols, ethyl acetate, dioxane, tetrahydrofuran or mixtures of these solvents at temperatures between 0° C. and the boiling point of the solvent, by treating with boron tribromide in methylene chloride at temperatures between −20° C. and ambient temperature, or by treating with aluminium chloride/anisol at temperatures between 0° C. and ambient temperature.

b) Deprotecting and Cyclising a Compound of General Formula (III)

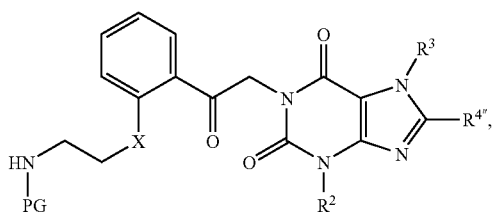

wherein $R^2$ and $R^3$ are as hereinbefore defined, $R^{4'}$ denotes one of the groups mentioned for $R^4$ hereinbefore which contain an imino, amino or alkylamino group, wherein the imino, amino or alkylamino group is substituted by one of the above-mentioned protective groups, X denotes an oxygen or sulphur atom, a sulphinyl, sulphonyl or an imino group substituted by $R_x$, and the —$CH_2$—$CH_2$—X-phenyl unit is substituted by $R^{10}$ to $R^{14}$ and may additionally be substituted by a $C_{1-3}$-alkyl group, wherein Rx and $R^{10}$ to $R^{14}$ are as hereinbefore defined, and PG also denotes one of the above-mentioned protective groups, wherein the two protective groups may be cleaved simultaneously or one after the other (cf. Example 2).

c) In order to prepare a compound of general formula I wherein $R^1$ denotes a 3-oxo-2,3-dihydro-isoindol-1-ylidenemethyl group optionally substituted by a group as defined in claims 1 to 4:

Deprotecting and dehydrating a compound of general formula

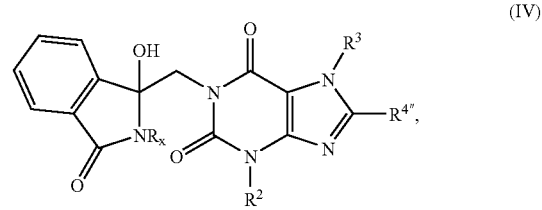

(IV)

wherein the benzo[group is substituted by $R^{10}$ to $R^{14}$, and $R^{10}$ to $R^{14}$ as well as $R_x$, $R^2$ and $R^3$ are as hereinbefore defined, and $R^{4'}$ denotes one of the groups mentioned for $R^4$ hereinbefore which contain an imino, amino or alkylamino group, wherein the imino, amino or alkylamino group is substituted by one of the above-mentioned protective groups and the dehydration is carried out under the same reaction conditions as the cleaving of the protective group (cf. Example 3).

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms racemic salts or derivatives such as e.g. esters or amides of an optically active substance, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-O-p-toluoyltartaric acid, malic acid, mandelic acid, camphorsulphonic acid, glutamic acid, aspartic acid or quinic acid. An optically active alcohol may be for example (+)- or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The compounds of general formulae II, III and IV used as starting materials are either known from the literature in some cases or may be obtained by methods known from the literature (cf. Examples I to XV).

As already mentioned hereinbefore, the compounds of general formula I according to the invention and the physiologically acceptable salts thereof have valuable pharmacological properties, particularly an inhibiting effect on the enzyme DPP-IV.

The biological properties of the new compounds were investigated as follows:

The ability of the substances and their corresponding salts to inhibit the DPP-IV activity can be demonstrated in a test set-up in which an extract of human colon carcinoma cell line Caco-2 is used as the DPP IV source. The differentiation of the cells in order to induce the DPP-IV expression was carried out as described by Reiher et al. in an article entitled "Increased expression of intestinal cell line Caco-2", which appeared in Proc. Natl. Acad. Sci. Vol. 90, pages 5757-5761 (1993). The cell extract was obtained from cells solubilised in a buffer (10 mM Tris HCl, 0.15 M NaCl, 0.04 t.i.u. aprotinin, 0.5% Nonidet-P40, pH 8.0) by centrifuging at 35,000 g for 30 minutes at 4° C. (to remove cell debris).

The DPP-IV assay was carried out as follows:

50 μl substrate solution (AFC; AFC is amido-4-trifluoromethylcoumarin), final concentration 100 μM, were placed in black microtitre plates. 20 μl of assay buffer (final concentrations 50 mM Tris HCl pH 7.8, 50 mM NaCl, 1% DMSO) was pipetted in. The reaction was started by adding 30 μl of solubilised Caco-2 protein (final concentration 0.14 μg of protein per well). The test substances to be investigated were typically added prediluted in 20 μl, and the volume of assay buffer was then reduced accordingly. The reaction was carried out at ambient temperature, incubating for 60 minutes. Then the fluorescence was measured in a Victor 1420 Multilabel Counter, the excitation wavelength being 405 nm and the emission wavelength being 535 nm. Blank readings (corresponding to 0% activity) were obtained in mixtures without any Caco-2 protein (volume replaced by assay buffer), control values (corresponding to 100% activity) were obtained in mixtures with no substance added. The potency of the test substances in question, expressed as $IC_{50}$ values, was calculated from dosage/activity curves consisting of 11 measuring points in each case. The following results were obtained:

| Compound (Example Nr.) | DPP IV inhibition $IC_{50}$ [nM] |
|---|---|
| 1 | 13 |
| 1(1) | 32 |
| 1(2) | 6 |
| 1(3) | 5 |
| 1(4) | 5 |
| 1(7) | 11 |
| 1(8) | 4 |
| 1(10) | 8 |
| 1(12) | 14 |
| 1(15) | 11 |
| 1(20) | 10 |
| 1(25) | 7 |
| 1(26) | 7 |
| 1(27) | 2 |
| 1(28) | 2 |
| 1(29) | 3 |
| 1(30) | 3 |
| 1(32) | 4 |
| 1(33) | 4 |
| 2 | 6 |
| 3 | 20 |

The compounds prepared according to the invention are well tolerated, as for example when 10 mg/kg of the compound of Example 1(2) were administered to rats by oral route no changes in the animals' behaviour could be detected.

In view of their ability to inhibit DPP-IV activity, the compounds of general formula I according to the invention and the corresponding pharmaceutically acceptable salts thereof are suitable for treating all those conditions or illnesses which can be influenced by the inhibition of the DPP-IV activity. It is therefore to be expected that the compounds according to the invention will be suitable for the prevention or treatment of diseases or conditions such as type I and type II diabetes mellitus, diabetic complications, metabolic acidosis or ketosis, insulin resistance, dyslipidaemias of various origins, arthritis, atherosclerosis and related diseases, obesity, allograft transplantation and calcitonin-induced osteoporosis. In addition these substances are capable of preventing B-cell degeneration such as e.g. apoptosis or necrosis of pancreatic B-cells. The substances are also suitable for improving or restoring the function of pancreatic cells and also increasing the number and size of pancreatic B-cells. Additionally, and on the basis of the role of the Glucagon-Like Peptides, such as e.g. GLP-1 and GLP-2 and their link with DPP-IV inhibition, it is likely that the compounds according to the invention are suitable for achieving, inter alia, a sedative or anxiety-relieving effect and also of favourably affecting catabolic states after operations or hormonal stress responses or of reducing mortality or morbidity after myocardial infarct. They are also suitable for treating all conditions which are connected with the above mentioned effects and which are mediated by GLP-1 or GLP-2. The compounds according to the invention may also be used as diuretics or antihypertensives and are suitable for preventing and treating acute renal failure. They are also suitable for the prevention and treatment of chronic inflammatory intestinal diseases. It is also expected that DPP-IV inhibitors and hence also the compounds according to the invention may be used to treat infertility or to improve fertility in humans or mammals, particularly when the infertility is connected with insulin resistance or polycystic ovary syndrome. The substances are also suitable for treating deficiencies of growth hormone which are associated with reduced stature.

The compounds according to the invention may also be used in conjunction with other active substances. Therapeutic agents which are suitable for such combinations include, for example, antidiabetics, such as metformin, sulphonylureas (e.g. glibenclamid, tolbutamide, glimepiride), nateglinide, repaglinide, thiazolidinedione (e.g. rosiglitazone, pioglitazone), PPAR-gamma agonists (e.g. GI 262570), alpha-glucosidase inhibitors (e.g. acarbose, voglibose), alpha2 antagonists, insulin and insulin analogues, GLP-1 and GLP-1 analogues (e.g. exendin-4) or amylin. Also, inhibitors of protein tyrosine phosphatase 1, substances which influence deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents, such as HMG-CoA-reductase inhibitors (e.g. simvastatin, atorvastatin), fibrates (e.g. bezafibrate, fenofibrate), nicotinic acid and its derivatives, cholesterol absorption inhibitors such as for example ezetimibe, bile acid-binding substances such as for example cholestyramine, HDL-raising compounds such as for example inhibitors of CETP or regulators of ABC1 or active substances for the treatment of obesity, such as e.g. sibutramine or tetrahydrolipostatin, or $\beta_3$-agonists such as SB-418790 or AD-9677.

It is also possible to combine the compounds with drugs for treating high blood pressure such as e.g. AII antagonists or ACE inhibitors, diuretics, β-blockers, etc., or combinations thereof.

The dosage required to achieve such an effect is expediently, by intravenous route, 1 to 100 mg, preferably 1 to 30 mg, and by oral route 1 to 1000 mg, preferably 1 to 100 mg, in each case 1 to 4 a day. For this purpose, the compounds of formula I prepared according to the invention, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The Examples that follow are intended to illustrate the invention:

Preparation of the Starting Compounds:

EXAMPLE I

1-[(1-methyl-2,2-dioxo-1H-benzo[c][1,2]thiazin-4-yl)methyl]-3-methyl-7-(3-methyl-2-buten-1-yl)-8-[3-(tert.-butyloxycarbonylamino)-piperidin-1-yl]-xanthine A mixture of 260 mg of 3-methyl-7-(3-methyl-2-buten-1-yl)-8-[3-(tert.-butyloxy-carbonylamino)-piperidin-1-yl]-xanthine, 185 mg of 4-bromo-methyl-1-methyl-1H-benzo[c][1,2]thiazine-2,2-dioxide and 550 mg of potassium carbonate in 4 ml N,N-dimethylformamide is stirred for about 40 h at ambient temperature. As no reaction of any note can be detected by thin layer chromatography, the mixture is heated to 60° C. for 2 h and then stirred for another 15 h at 50° C. until the reaction is virtually complete. Then 30 ml of water are added, the precipitate formed is suction filtered and dried. The crude product is purified by chromatography over a silica gel column with petroleum ether/ethyl acetate (1:1) as eluant.

Yield: 225 mg of (59% of theory)

$R_f$ value: 0.19 (silica gel, petroleum ether/ethyl acetate=1:1)

Mass spectrum (ESI$^+$): m/z=640 [M+H]$^+$

The following compounds are obtained analogously to Example 1:

(1) 1-[(3-methoxycarbonyl-3-methyl-3,4-dihydro-isoquinolin-1-yl]methyl]-3-methyl-7-(2-butyn-1-yl)-8-[3-(tert.-butyloxycarbonylamino)-piperidin-1-yl]-xanthine $R_f$ value: 0.42 (silica gel, methylene chloride/methanol/conc. aqueous ammonia=95:5)

Mass spectrum (ESI$^+$): m/z=632 [M+H]$^+$ (2) 1-[2-(2-methoxy-phenyl)-2-oxo-ethyl]-3-methyl-7-(2-butyn-1-yl)-8-bromo-xanthine Mass spectrum (ESI$^+$): m/z=445, 447 [M+H]$^+$ (3) 1-[2-(2-ethoxycarbonyl-phenyl)-2-oxo-ethyl]-3-methyl-7-(3-methyl-2-buten-1-yl)-8-[3-(tert.-butyloxycarbonylamino)-piperidin-1-yl]-xanthine (carried out in N-methylpyrrolidin-2-one at 60° C.)

$R_f$ value: 0.35 (silica gel, methylene chloride/methanol=20:1)

Mass spectrum (ESI$^+$): m/z=623 [M+H]$^+$ (4) 1-[2-(2-nitro-phenyl)-2-oxo-ethyl]-3-methyl-7-((E)-2-buten-1-yl)-8-bromo-xanthine Mass spectrum (ESI$^+$): m/z=462, 464 [M+H]$^+$ (5) 1-[(phenanthridin-6-yl)methyl]-3-methyl-7-(2-butyn-1-yl)-8-[3-(tert.-butyloxycarbonylamino)-piperidin-1-yl]-xanthine $R_f$ value: 0.80 (silica gel, ethyl acetate)

Mass spectrum (ESI$^+$): m/z=608 [M+H]$^+$ (6) 1-[(1,2,3,4-tetrahydro-phenanthridin-6-yl)methyl]-3-methyl-7-(2-butyn-1-yl)-8-[3-(tert.-butyloxycarbonylamino)-piperidin-1-yl]-xanthine $R_f$ value: 0.55 (silica gel, ethyl acetate/petroleum ether=2:1)

Mass spectrum (ESI$^+$): m/z=612 [M+H]$^+$ (7) 1-[(11H-dibenzo[b,e]azepin-6-yl)methyl]-3-methyl-7-(2-butyn-1-yl)-8-[3-(tert.-butyloxycarbonylamino)-piperidin-1-yl]-xanthine $R_f$ value: 0.40 (silica gel, cyclohexane/ethyl acetate=1:1)

Mass spectrum (ESI$^+$): m/z=622 [M+H]$^+$ (8) 1-[(dibenzo[b,f][1,4]oxazepin-11-yl)methyl]-3-methyl-7-(2-butyn-1-yl)-8-[3-(tert.-butyloxycarbonylamino)-piperidin-1-yl]-xanthine $R_f$ value: 0.70 (silica gel, ethyl acetate/cyclohexane=3:1)

Mass spectrum (ESI$^+$): m/z=624 [M+H]$^+$ (9) 1-[(3-trifluoromethyl-3,4-dihydro-isoquinolin-1-yl)methyl]-3-methyl-7-(2-butyn-1-yl)-8-[3-(tert.-butyloxycarbonylamino)-piperidin-1-yl]-xanthine $R_f$ value: 0.60 (aluminium oxide, petroleum ether/ethyl acetate=1:1)

Mass spectrum (ESI$^+$): m/z=628 [M+H]$^+$

(10) 1-[(dibenzo[b,f][1,4]oxazepin-11-yl)methyl]-3-methyl-7-(2-butyn-1-yl)-8-[(R)-3-(tert.-butyloxycarbonylamino)-piperidin-1-yl]-xanthine $R_f$ value: 0.75 (silica gel, ethyl acetate)

Mass spectrum (ESI$^+$): m/z=624 [M+H]$^+$

(11) 1-[(3,3-dimethyl-3,4-dihydro-isoquinolin-1-yl)methyl]-3-methyl-7-(2-butyn-1-yl)-8-[3-(tert.-butyloxycarbonylamino)-piperidin-1-yl]-xanthine
$R_f$ value: 0.50 (silica gel, ethyl acetate)
Mass spectrum (ESI$^+$): m/z=588 [M+H]$^+$

(12) 1-[(methoxycarbonyl)methyl]-3-methyl-7-(2-butyn-1-yl)-8-[3-(tert.-butyloxycarbonyl-amino)-piperidin-1-yl]-xanthine
Mass spectrum (ESI$^+$): m/z=489 [M+H]$^+$

(13) 1-cyanomethyl-3-methyl-7-(2-butyn-1-yl)-8-[3-(tert.-butyloxycarbonyl-amino)-piperidin-1-yl]-xanthine
Mass spectrum (ESI$^+$): m/z=456 [M+H]$^+$

(14) 1-[(5-methyl-5H-dibenzo[b,e][1,4]diazepin-11-yl)methyl]-3-methyl-7-(2-butyn-1-yl)-8-[3-(tert.-butyloxycarbonyl-amino)-piperidin-1-yl]-xanthine
$R_f$ value: 0.60 (silica gel, methylene chloride/ethyl acetate=1:1)
Mass spectrum (ESI$^+$): m/z=637 [M+H]$^+$

(15) 1-[(8-methyl-dibenzo[b,f][1,4]oxazepin-11-yl)methyl]-3-methyl-7-(2-butyn-1-yl)-8-[3-(tertbutyloxycarbonyl-amino)-piperidin-1-yl]-xanthine
$R_f$ value: 0.65 (silica gel, methylene chloride/ethyl acetate=1:1)
Mass spectrum (ESI$^+$): m/z=638 [M+H]$^+$

(16) 1-[(2-methyl-dibenzo[b,f][1,4]oxazepin-11-yl)methyl]-3-methyl-7-(2-butyn-1-yl)-8-[3-(tert.-butyloxycarbonyl-amino)-piperidin-1-yl]-xanthine
$R_f$ value: 0.70 (silica gel, methylene chloride/ethyl acetate=1:1)
Mass spectrum (ESI$^+$): m/z=638 [M+H]$^+$

(17) 1-[(benzo[1,2,5]oxadiazol-5-yl)methyl]-3-methyl-7-(2-butyn-1-yl)-8-[3-(tert.-butyloxycarbonyl-amino)-piperidin-1-yl]-xanthine
$R_f$ value: 0.73 (silica gel, methylene chloride/ethyl acetate=1:1)
Mass spectrum (ESI$^+$): m/z=549 [M+H]$^+$

(18) 1-[(2-chloro-dibenzo[b,f][1,4]oxazepin-11-yl)methyl]-3-methyl-7-(2-butyn-1-yl)-8-[3-(tert.-butyloxycarbonyl-amino)-piperidin-1-yl]-xanthine
$R_f$ value: 0.75 (silica gel, methylene chloride/ethyl acetate=1:1)
Mass spectrum (ESI$^+$): m/z=658, 660 [M+H]$^+$

(19) 1-[(phenanthridin-6-yl)methyl]-3-cyclopropyl-7-(2-butyn-1-yl)-8-[3-(tert.-butyloxycarbonyl-amino)-piperidin-1-yl]-xanthine
$R_f$ value: 0.55 (silica gel, methylene chloride/ethyl acetate=1:1)
Mass spectrum (ESI$^+$): m/z=634 [M+H]$^+$

(20) 1-[(8-methyl-phenanthridin-6-yl)methyl]-3-methyl-7-(2-butyn-1-yl)-8-[3-(tert.-butyloxycarbonyl-amino)-piperidin-1-yl]-xanthine
$R_f$ value: 0.67 (silica gel, methylene chloride/ethyl acetate=1:1)
Mass spectrum (ESI$^+$): m/z=622 [M+H]$^+$

(21) 1-[(phenanthridin-6-yl)methyl]-3-methyl-7-(2-butyn-1-yl)-8-[(S)-3-(tert.-butyloxycarbonyl-amino)-piperidin-1-yl]-xanthine
$R_f$ value: 0.75 (silica gel, methylene chloride/ethyl acetate=1:1)
Mass spectrum (ESI$^+$): m/z=608 [M+H]$^+$

(22) 1-[(phenanthridin-6-yl)methyl]-3-cyclopropyl-7-(2-butyn-1-yl)-8-[(R)-3-(tert.-butyloxycarbonyl-amino)-piperidin-1-yl]-xanthine
$R_f$ value: 0.60 (silica gel, methylene chloride/ethyl acetate=1:1)
Mass spectrum (ESI$^+$): m/z=634 [M+H]$^+$

(23) 1-[(dibenzofuran-2-yl)methyl]-3-methyl-7-(2-butyn-1-yl)-8-[(R)-3-(tert.-butyloxycarbonyl-amino)-piperidin-1-yl]-xanthine
$R_f$ value: 0.85 (silica gel, methylene chloride/ethyl acetate=1:1)
Mass spectrum (ESI$^+$): m/z=597 [M+H]$^+$

(24) 1-[(1-methyl-phenanthridin-6-yl)methyl]-3-methyl-7-(2-butyn-1-yl)-8-[(R)-3-(tert.-butyloxycarbonyl-amino)-piperidin-1-yl]-xanthine
$R_f$ value: 0.80 (silica gel, methylene chloride/ethyl acetate=1:1)
Mass spectrum (ESI$^+$): m/z=622 [M+H]$^+$

(25) 1-[(4-methyl-phenanthridin-6-yl)methyl]-3-methyl-7-(2-butyn-1-yl)-8-[(R)-3-(tert.-butyloxycarbonyl-amino)-piperidin-1-yl]-xanthine
$R_f$ value: 0.85 (silica gel, methylene chloride/ethyl acetate=1:1)
Mass spectrum (ESI$^+$): m/z=622 [M+H]$^+$

(26) 1-[(benzo[h][1,6]naphthyridin-5-yl)methyl]-3-methyl-7-(2-butyn-1-yl)-8-[3-(tert.-butyloxycarbonyl-amino)-piperidin-1-yl]-xanthine
$R_f$ value: 0.54 (silica gel, methylene chloride/methanol=94:6)
Mass spectrum (ESI$^+$): m/z=609 [M+H]$^+$

(27) 1-[(pyrazolo[1,5-c]quinazolin-5-yl)methyl]-3-methyl-7-(2-butyn-1-yl)-8-[3-(tert.-butyloxycarbonyl-amino)-piperidin-1-yl]-xanthine
$R_f$ value: 0.67 (silica gel, ethyl acetate)
Mass spectrum (ESI$^+$): m/z=598 [M+H]$^+$

(28) 1-[(benzo[c][1,8]naphthyridin-6-yl)methyl]-3-methyl-7-(2-butyn-1-yl)-8-[3-(tert.-butyloxycarbonyl-amino)-piperidin-1-yl]-xanthine
$R_f$ value: 0.40 (silica gel, methylene chloride/methanol=95:5)
Mass spectrum (ESI$^+$): m/z=609 [M+H]$^+$

(29) 1-[(benzo[c][1,5]naphthyridin-6-yl)methyl]-3-methyl-7-(2-butyn-1-yl)-8-[(R)-3-(tert.-butyloxycarbonyl-amino)-piperidin-1-yl]-xanthine
$R_f$ value: 0.55 (silica gel, methylene chloride/methanol=95:5)
Mass spectrum (ESI$^+$): m/z=609 [M+H]$^+$

(30) 1-cyanomethyl-3-methyl-7-(2-butyn-1-yl)-8-[(R)-3-(tert.-butyloxycarbonyl-amino)-piperidin-1-yl]-xanthine
$R_f$ value: 0.80 (silica gel, ethyl acetate)
Mass spectrum (ESI$^+$): m/z=456 [M+H]$^+$

(31) 1-[(benzo[f]quinoxalin-6-yl)methyl]-3-methyl-7-(2-butyn-1-yl)-8-[(R)-3-(tert.-butyloxycarbonyl-amino)-piperidin-1-yl]-xanthine
$R_f$ value: 0.48 (silica gel, methylene chloride/methanol=95:5)
Mass spectrum (ESI$^+$): m/z=609 [M+H]$^+$

(32) 1-[(imidazo[2,1-a]isoquinolin-2-yl)methyl]-3-methyl-7-(2-butyn-1-yl)-8-[3-(tert.-butyloxycarbonyl-amino)-piperidin-1-yl]-xanthine
$R_f$ value: 0.47 (silica gel, methylene chloride/methanol=95:5)
Mass spectrum (ESI$^+$): m/z=597 [M+H]$^+$

(33) 1-[(imidazo[1,2-a]isoquinolin-2-yl)methyl]-3-methyl-7-(2-butyn-1-yl)-8-[3-(tert.-butyloxycarbonyl-amino)-piperidin-1-yl]-xanthine
$R_f$ value: 0.14 (silica gel, ethyl acetate)
Mass spectrum (ESI$^+$): m/z=597 [M+H]$^+$

(34) 1-[(phenanthridin-6-yl)methyl]-3-methyl-7-(2-butyn-1-yl)-8-[(R)-3-(tert.-butyloxycarbonyl-amino)-piperidin-1-yl]-xanthine
$R_f$ value: 0.20 (silica gel, cyclohexane/ethyl acetate=1:1)
Mass spectrum (ESI$^+$): m/z=608 [M+H]$^+$

EXAMPLE II

4-Bromo-methyl-1-methyl-1H-benzo[c][1,2]thiazin-2,2-dioxide 390 mg of 1,4-dimethyl-1H-benzo[c][1,2]thiazin-2,2-dioxide in 20 ml 1,2-dichloroethane are combined with 332 mg of N-bromosuccinimide and 50 mg of 2,2'-azodiisobutyronitrile. The yellow solution is refluxed for a total of 10 h and then left to stand for another two days at ambient temperature. The reaction mixture is distributed between water and methylene chloride, the organic phase is washed with water, dried over magnesium sulphate and evaporated down. A yellowish resin is left which is purified through a silica gel column with petroleum ether/ethyl acetate (5:1 to 4:1) as eluant. A mixture of 4-bromo-methyl-1-methyl-1H-benzo[c][1,2]thiazin-2,2-dioxide and 3-bromo-1,4-dimethyl-1H-benzo[c][1,2]thiazin-2,2-dioxide is obtained, which is further reacted as it is.
Yield: 190 mg (35% of theory)
Mass spectrum (ESI$^+$): m/z=288, 290 [M+H]$^+$ The following compounds are obtained analogously to Example II:

(1) 5-bromomethyl-benzo[h][1,6]naphthyridine
$R_f$ value: 0.76 (silica gel, ethyl acetate/petroleum ether=1:1)
Mass spectrum (ESI$^+$): m/z=273, 275 [M+H]$^+$ (2) 6-chloromethyl-benzo[c][1,8]naphthyridine (carried out with N-chlorosuccinimide in the presence of benzoyl peroxide in carbon tetrachloride)
$R_f$ value: 0.47 (silica gel, ethyl acetate/methanol=98:2)

(3) 6-bromomethyl-benzo[c][1,5]naphthyridine (carried out in the presence of benzoyl peroxide in carbon tetrachloride)
$R_f$ value: 0.64 (silica gel, ethyl acetate/petroleum ether=1:2)
Mass spectrum (ESI$^+$): m/z=273, 275 [M+H]$^+$ (4) 6-bromomethyl-benzo[f]quinoxaline (carried out in the presence of benzoyl peroxide in carbon tetrachloride)
$R_f$ value: 0.33 (silica gel, ethyl acetate/petroleum ether=1:5)
Mass spectrum (ESI$^+$): m/z=273, 275 [M+H]$^+$

EXAMPLE III 3-methyl-7-(3-methyl-2-buten-1-yl)-8-[3-(tert.-butyloxycarbonylamino)-piperidin-1-yl]-xanthine A mixture of 20.50 g of 3-methyl-7-(3-methyl-2-buten-1-yl)-8-bromo-xanthine, 13.64 g of 3-tert.-butyloxycarbonylamino-piperidine and 20.27 g of potassium carbonate in 100 ml dimethylsulphoxide is stirred for 4 h at 115° C. Then a further 2.50 g of 3-tert.-butyloxycarbonylamino-piperidine are added and the reaction mixture is stirred for a further 2 h at 115° C. The cooled reaction solution is poured onto 1 l of ice water, the precipitate formed is suction filtered, washed with water and dried.
$R_f$ value: 0.60 (silica gel, ethyl acetate)
Mass spectrum (ESI$^+$): m/z=433 [M+H]$^+$ The following compounds are obtained analogously to Example III:

(1) 3-methyl-7-(2-butyn-1-yl)-8-[3-(tert.-butyloxycarbonylamino)-piperidin-1-yl]-xanthine
melting point: 235-237° C.
Mass spectrum (ESI$^+$): m/z=417 [M+H]$^+$ (2) 1-[2-(2-hydroxy-phenyl)-2-oxo-ethyl]-3-methyl-7-(2-butyn-1-yl)-8-[3-(tert.-butyloxycarbonyl-amino)-piperidin-1-yl]-xanthine
Mass spectrum (ESI$^+$): m/z=551 [M+H]$^+$ (3) 1-[2-(2-nitro-phenyl)-2-oxo-ethyl]-3-methyl-7-((E)-2-buten-1-yl)-8-[(R)-3-(tert.-butyloxycarbonylamino)-piperidin-1-yl]-xanthine
$R_f$ value: 0.50 (silica gel, cyclohexane/ethyl acetate=1:2)
Mass spectrum (ESI$^+$): m/z=582 [M+H]$^+$ (4) 3-methyl-7-(2-butyn-1-yl)-8-[(R)-3-(tert.-butyloxycarbonylamino)-piperidin-1-yl]-xanthine
Mass spectrum (ESI$^+$): m/z=417 [M+H]$^+$ (5) 3-cyclopropyl-7-(2-butyn-1-yl)-8-[3-(tert.-butyloxycarbonyl-amino)-piperidin-1-yl]-xanthine
$R_f$ value: 0.70 (silica gel, ethyl acetate)
Mass spectrum (ESI$^+$): m/z=443 [M+H]$^+$ (6) 3-methyl-7-(2-butyn-1-yl)-8-[(S)-3-(tert.-butyloxycarbonyl-amino)-piperidin-1-yl]-xanthine
$R_f$ value: 0.73 (silica gel, ethyl acetate)
Mass spectrum (ESI$^+$): m/z=417 [M+H]$^+$ (7) 3-cyclopropyl-7-(2-butyn-1-yl)-8-[(R)-3-(tert.-butyloxycarbonyl-amino)-piperidin-1-yl]-xanthine
$R_f$ value: 0.35 (Reversed phase ready-made TLC plate (E. Merck), acetonitrile/water/trifluoroacetic acid=50:50:1)
Mass spectrum (ESI$^+$): m/z=443 [M+H]$^+$ (8) 1-[(indolizin-2-yl)methyl]-3-methyl-7-(2-butyn-1-yl)-8-[3-(tert.-butyloxycarbonyl-amino)-piperidin-1-yl]-xanthine
$R_f$ value: 0.29 (silica gel, petroleum ether/ethyl acetate=1:1)
Mass spectrum (ESI$^+$): m/z=546 [M+H]$^+$

EXAMPLE IV 3-methyl-7-(3-methyl-2-buten-1-yl)-8-bromo-xanthine 15.37 ml of Hünig base and 9.98 ml of 3,3-dimethylallylbromide are added to 20.00 g of 3-methyl-8-bromo-xanthine in 200 ml of N,N-dimethylformamide. The reaction mixture is stirred for about half an hour at ambient temperature and then diluted with 500 ml of water. The precipitate formed is suction filtered, washed with water and dried.
Yield: 20.50 g (80% of theory)
Mass spectrum (ESI$^+$): m/z=313, 315 [M+H]$^+$ The following compounds are obtained analogously to Example IV:

(1) 3-methyl-7-(2-butyn-1-yl)-8-bromo-xanthine
$R_f$ value: 0.72 (silica gel, ethyl acetate)
Mass spectrum (ESI$^+$): m/z=297, 299 [M+H]$^+$ (2) 3-methyl-7-((E)-2-buten-1-yl)-8-bromo-xanthine
Mass spectrum (ESI$^+$): m/z=299, 301 [M+H]$^+$ (3) 3-cyclopropyl-7-(2-butyn-1-yl)-8-bromo-xanthine
$R_f$ value: 0.45 (Reversed phase ready-made TLC plate (E. Merck), acetonitrile/water/trifluoroacetic acid=50:50:1)
Mass spectrum (ESI$^+$): m/z=323, 325 [M+H]$^+$

EXAMPLE V

Methyl 1-chloromethyl-3-methyl-3,4-dihydro-isoquinolin-3-yl-carboxylate

Prepared from methyl 2-(2-chloro-acetylamino)-2-methyl-3-phenyl-propionate analogously to Das et al., *Indian J. Chem.* 1985, 24B, 1302.

$R_f$ value: 0.52 (silica gel, petroleum ether/ethyl acetate=2:1)

Mass spectrum (ESI$^+$): m/z=252, 254 [M+H]$^+$

EXAMPLE VI 1-(2-{2-[2-(tert.-butyloxycarbonylamino)-ethoxy]-phenyl}-2-oxo-ethyl)-3-methyl-7-(2-butyn-1-yl)-8-[3-(tert.-butyloxycarbonyl-amino)-piperidin-1-yl]-xanthine 187 mg of tert.-butyl 2-bromo-ethyl-carbaminate are added to 400 mg of 1-[2-(2-hydroxy-phenyl)-2-oxo-ethyl]-3-methyl-7-(2-butyn-1-yl)-8-[3-(tert.-butyloxycarbonyl-amino)-piperidin-1-yl]-xanthine and 150 mg of potassium carbonate in 6 ml N,N-dimethylformamide and the reaction mixture is stirred overnight at 55° C. Then a further 90 mg of tert.-butyl 2-bromo-ethyl-carbaminate are added. After another eight hours at 55° C. the reaction is complete. The cooled reaction mixture is combined with water, the precipitate formed is suction filtered, washed with water and dried.

Yield: 368 mg (73% of theory)

Mass spectrum (ESI$^+$): m/z=694 [M+H]$^+$

EXAMPLE VII

1-[2-(2-hydroxy-phenyl)-2-oxo-ethyl]-3-methyl-7-(2-butyn-1-yl)-8-bromo-xanthine

Prepared by treating 1-[2-(2-methoxy-phenyl)-2-oxo-ethyl]-3-methyl-7-(2-butyn-1-yl)-8-bromo-xanthine with boron tribromide in the presence of 4 Å molecular sieve in methylene chloride at 4° C.

Mass spectrum (ESI$^+$): m/z=431, 433 [M+H]$^+$

EXAMPLE VIII

1-[(1-hydroxy-3-oxo-2,3-dihydro-1H-isoindol-1-yl)methyl]-3-methyl-7-(3-methyl-2-buten-1-yl)-8-[3-(tert.-butyloxycarbonyl-amino)-piperidin-1-yl]-xanthine A mixture of 250 mg of 1-[2-(2-carboxy-phenyl)-2-oxo-ethyl]-3-methyl-7-(3-methyl-2-buten-1-yl)-8-[3-(tert.-butyloxycarbonyl-amino)-piperidin-1-yl]-xanthine, 404 mg of ammonium carbonate, 135 mg of O-(benzotriazol-1-yl)-N,N,N',N'-tetramethyluronium-tetrafluoroborate, 57 mg of hydroxybenzotriazole and 59 µl of triethylamine in 3 ml of tetrahydrofuran is stirred for eight hours at ambient temperature. For working up the reaction mixture is diluted with 30 ml of ethyl acetate and washed with 10% citric acid solution, 10% potassium carbonate solution and saturated sodium chloride solution. The organic phase is evaporated down and chromatographed through a silica gel column with methylene chloride/methanol (98:2 to 80:20).

The cyclised compound is obtained as the main product.

Yield: 160 mg (64% of theory)

$R_f$ value: 0.40 (silica gel, methylene chloride/methanol=9:1)

Mass spectrum (ESI$^+$): m/z=594 [M+H]$^+$

EXAMPLE IX

1-[2-(2-carboxy-phenyl)-2-oxo-ethyl]-3-methyl-7-(3-methyl-2-buten-1-yl)-8-[3-(tert.-butyloxycarbonylamino)-piperidin-1-yl]-xanthine A mixture of 2.60 g of 1-[2-(2-ethoxycarbonyl-phenyl)-2-oxo-ethyl]-3-methyl-7-(3-methyl-2-buten-1-yl)-8-[3-(tert.-butyloxycarbonylamino)-piperidin-1-yl]-xanthine and 8 ml of 3 N sodium hydroxide solution in 25 ml of methanol is stirred for two hours at ambient temperature. For working up the reaction mixture is neutralised with 24 ml of 1 N hydrochloric acid, acidified slightly by the addition of 20 ml of 10% citric acid solution and extracted with ethyl acetate. The combined extracts are washed with saturated sodium chloride solution, dried over magnesium sulphate and evaporated down.

Yield: 2.00 g (80% of theory)

$R_f$ value: 0.49 (silica gel, methylene chloride/methanol=9:1)

Mass spectrum (ESI$^+$): m/z=593 [M−H]$^-$

The following compound is obtained analogously to Example IX:

(1) 1-carboxymethyl-3-methyl-7-(2-butyn-1-yl)-8-[3-(tert.-butyloxycarbonyl-amino)-piperidin-1-yl]-xanthine (The ester cleaving is carried out with 4 M potassium hydroxide solution in a mixture of methanol and tetrahydrofuran.)

Mass spectrum (ESI$^-$): m/z=473 [M−H]$^-$

EXAMPLE X

1-[(2-oxo-2,3-dihydro-1H-benzo[e][1,4]diazepin-5-yl)methyl]-3-methyl-7-((E)-2-buten-1-yl)-8-[(R)-3-(tert.-butyloxycarbonylamino)-piperidin-1-yl]-xanthine A mixture of 200 mg of 1-{2-[2-(2-chloro-acetylamino)-phenyl]-2-oxo-ethyl}-3-methyl-7-((E)-2-buten-1-yl)-8-[(R)-3-(tert.-butyloxycarbonylamino)-piperidin-1-yl]-xanthine, 5 ml of conc. ammonia, 2 ml of tetrahydrofuran and 2 ml of methanol is stirred at ambient temperature for about a week. Then the dark reaction mixture is added to a pack of 14 g of Extrelut and after 20 minutes washed out thoroughly with methylene chloride. The filtrate is evaporated down and chromatographed through a silica gel column with ethyl acetate/methanol (10:0 to 8:2) as eluant.

Yield: 95 mg (51% of theory)

$R_f$ value: 0.25 (silica gel, cyclohexane/ethyl acetate=2:8)

EXAMPLE XI

1-{2-[2-(2-chloro-acetylamino)-phenyl]-2-oxo-ethyl}-3-methyl-7-((E)-2-buten-1-yl)-8-[(R)-3-(tert.-butyloxycarbonylamino)-piperidin-1-yl]-xanthine 51 µl of bromoacetyl chloride are added to 319 mg of 1-[2-(2-amino-phenyl)-2-oxo-ethyl]-3-methyl-7-((E)-2-buten-1-yl)-8-[(R)-3-(tert.-butyloxycarbonyl-amino)-piperidin-1-yl]-xanthine and 60 µl pyridine in 1 ml methylene chloride. The reaction mixture is stirred for two hours at 35° C. and after cooling to ambient temperature, combined with 0.5 M citric acid. The organic phase is separated off and the aqueous phase is extracted with methylene chloride. The combined organic phases are evaporated down and chromatographed through a silica gel column with cyclohexane/ethyl acetate (6:4) as eluant.

Yield: 210 mg (58% of theory)

$R_f$ value: 0.50 (silica gel, cyclohexane/ethyl acetate/isopropanol=14:3:3)

Mass spectrum (ESI$^+$): m/z=628, 630 [M+H]$^+$

The following compounds are obtained analogously to Example XI:

(1) N-(1-benzyl-2,2,2-trifluoro-ethyl)-2-chloro-acetamide (The reaction is carried out with chloroacetyl chloride in diethyl ether in the presence of triethylamine).

$R_f$ value: 0.45 (aluminium oxide, petroleum ether/ethyl acetate=5:1)

Mass spectrum (ESI$^+$): m/z=266 [M+H]$^+$ (2) 2-chloro-N-(4-methyl-biphenyl-2-yl)-acetamide (The reaction is carried out with chloroacetyl chloride in the presence of diisopropylethylamine.)

$R_f$ value: 0.82 (silica gel, cyclohexane/ethyl acetate=1:1)

Mass spectrum (ESI$^+$): m/z=260, 262 [M+H]$^+$ (3) 2-chloro-N-(6-methyl-biphenyl-2-yl)-acetamide (The reaction is carried out with chloroacetyl chloride in the presence of diisopropylethylamine.)

$R_f$ value: 0.60 (silica gel, cyclohexane/ethyl acetate=3:1)

Mass spectrum (ESI$^+$): m/z=260, 262 [M+H]$^+$ (4) 2-chloro-N-(3-methyl-biphenyl-2-yl)-acetamide (The reaction is carried out with chloroacetyl chloride in the presence of diisopropylethylamine.)

$R_f$ value: 0.45 (silica gel, cyclohexane/ethyl acetate=3:1)

EXAMPLE XII

1-[2-(2-amino-phenyl)-2-oxo-ethyl]-3-methyl-7-((E)-2-buten-1-yl)-8-[(R)-3-(tert.-butyloxycarbonylamino)-piperidin-1-yl]-xanthine Prepared by reduction of 6.34 g 1-[2-(2-nitro-phenyl)-2-oxo-ethyl]-3-methyl-7-((E)-2-buten-1-yl)-8-[(R)-3-(tert.-butyloxycarbonylamino)-piperidin-1-yl]-xanthine with 5.15 g iron powder in a mixture of 260 ml of ethanol, 85 ml of water and 33 ml glacial acetic acid at reflux temperature.

Yield: 5.38 g (90% of theory)

Mass spectrum (ESI$^+$): m/z=552 [M+H]$^+$

EXAMPLE XIII 6-chloromethyl-1,2,3,4-tetrahydro-phenanthridine-hydrochloride

Prepared by treating 110 mg of 6-hydroxymethyl-1,2,3,4-tetrahydro-phenanthridine with 60 µl of thionyl chloride in 2.5 ml methylene chloride at 0° C. to ambient temperature.

Yield: 140 mg (100% of theory)

$R_f$ value: 0.50 (silica gel, petroleum ether/ethyl acetate=5:1)

Mass spectrum (ESI$^+$): m/z=232, 234 [M+H]$^+$

EXAMPLE XIV 6-hydroxymethyl-1,2,3,4-tetrahydro-phenanthridine

A solution of 350 mg of ethyl 1,2,3,4-tetrahydro-phenanthridin-6-yl-carboxylate in 10 ml of tetrahydrofuran is added dropwise within five minutes to a suspension of 37 mg of lithium borohydride in 15 ml of tetrahydrofuran, wherein cooling with an ice bath. Then the ice bath is removed and the reaction mixture is stirred for a further 2.5 hours at ambient temperature. For working up, 2 ml of 1 M citric acid are added to the brown reaction solution wherein cooling with an ice bath. The mixture is stirred with 100 ml of ethyl acetate and 50 ml of water and adjusted to pH 10 with 4 N sodium hydroxide solution. The organic phase is separated off, washed with water, dried over magnesium sulphate and evaporated down. The flask residue is chromatographed through a silica gel column with ethyl acetate/petroleum ether (1:4 to 1:1) as eluant.

Yield: 120 mg (41% of theory)

$R_f$ value: 0.40 (silica gel, petroleum ether/ethyl acetate=2:1)

Mass spectrum (ESI$^+$): m/z=214 [M+H]$^+$

Example XV

Ethyl 1.2.3.4-tetrahydro-phenanthridin-6-yl-carboxylate

Analogously to the method described by Gonsalves et al. (*Tetrahedron* 1992, 48, 6821) a solution of 3.90 g of ethyl 5,6,7,8-tetrahydro-benzo[1,2,4]triazine-3-carboxylate (Sagi et al., *Heterocycles* 1989, 29, 2253) is refluxed in 20 ml of dioxane. Then 8.22 g anthranilic acid and 7.02 g isoamyl nitrite, in each case dissolved in 20 ml dioxane, are simultaneously added dropwise within 25 minutes using two dropping funnels. The reaction mixture is refluxed for a further 30 minutes. For working up the cooled dark brown reaction solution is diluted with 150 ml diethyl ether, washed with 100 ml of 2 N sodium hydroxide solution and with water, dried over magnesium sulphate and evaporated down. The brown, oily flask residue is chromatographed through a silica gel column with ethyl acetate/petroleum ether (20:80 to 50:50) as eluant. The product obtained is still somewhat contaminated but is further reacted without any further purification.

Yield: 380 mg (8% of theory)

$R_f$ value: 0.55 (silica gel, petroleum ether/ethyl acetate=2:1)

Mass spectrum (ESI$^+$): m/z=256 [M+H]$^+$

EXAMPLE XVI 1-chloromethyl-3-trifluoromethyl-3.4-dihydro-isoquinoline 0.74 ml of phosphorus oxychloride and 530 mg of N-(1-benzyl-2,2,2-trifluoro-ethyl)-2-chloro-acetamide are added to 4.00 g of warm polyphosphoric acid and the viscous reaction mixture is stirred for 1.5 h at 130° C. After cooling to ambient temperature the reaction mixture is stirred with ice water and suction filtered. The filter cake is dissolved in ethyl acetate, the solution is dried over magnesium sulphate and evaporated down. A white solid is left.

Yield: 415 mg (84% of theory)

$R_f$ value: 0.55 (aluminium oxide, petroleum ether/ethyl acetate=10:1)

Mass spectrum (ESI$^+$): m/z=248, 250 [M+H]$^+$

EXAMPLE XVII

1-[(3,4-dihydro-quinazolin-2-yl)methyl]-3-methyl-7-(2-butyn-1-yl)-8-[3-(tert.-butyloxycarbonyl-amino)-piperidin-1-yl]-xanthine A mixture of 280 mg of 1-[2-(2-amino-benzylamino)-2-oxo-ethyl]-3-methyl-7-(2-butyn-1-yl)-8-[3-(tert.-butyloxycarbonyl-amino)-piperidin-1-yl]-xanthine and 4 ml glacial acetic acid is heated to boiling for two hours. Then the reaction mixture is evaporated down and the flask residue is purified through a column of aluminium oxide (activity stage III) with methylene chloride/ethyl acetate/methanol (5:5:0 to 5:4:1) as eluant. In addition to the desired 1-[(3,4-dihydroquinazolin-2-yl)methyl]-3-methyl-7-(2-butyn-1-yl)-8-[3-(tert.-butyloxycarbonyl-amino)-piperidin-1-yl]-xanthine, deprotected 1-[(3,4-dihydro-quinazolin-2-yl)methyl]-3-methyl-7-(2-butyn-1-yl)-8-(3-amino-piperidin-1-yl)-xanthine is also obtained.

Yield: 120 mg (44% of theory)
Mass spectrum (ESI$^+$): m/z=561 [M+H]$^+$

EXAMPLE XVIII

1-[2-(2-amino-benzylamino)-2-oxo-ethyl]-3-methyl-7-(2-butyn-1-yl)-8-[3-(tert.-butyloxycarbonyl-amino)-pipieridin-1-yl]-xanthine A mixture of 397 mg of 1-carboxymethyl-3-methyl-7-(2-butyn-1-yl)-8-[3-(tert.-butyloxycarbonyl-amino)-piperidin-1-yl]-xanthine, 110 mg of 2-amino-benzylamine and 460 µl of diisopropylethylamine in 3 ml of N,N-dimethylformamide is combined with 272 mg of (benzotriazol-1-yl)-N-tetramethyl-uronium-tetrafluoroborate and stirred for two hours at ambient temperature. Then the reaction mixture is evaporated down, the residue is triturated with 15 ml 1M sodium hydroxide solution and suction filtered. The filter cake is washed with a little ethanol and diethyl ether and dried.

Yield: 400 mg (83% of theory)
$R_f$ value: 0.68 (silica gel, methylene chloride/methanol=9:1)
Mass spectrum (ESI$^+$): m/z=579 [M+H]$^+$

EXAMPLE XIX

1-[(3-methyl-3,4-dihydro-quinazolin-2-yl)methyl]-3-methyl-7-(2-butyn-1-yl)-8-[3-(tert.-butyloxycarbonyl-amino)-piperidin-1-yl]-xanthine 0.5 ml of 1 M sodium methoxide solution are added to 400 mg of 1-cyanomethyl-3-methyl-7-(2-butyn-1-yl)-8-[3-(tert.-butyloxycarbonyl-amino)-piperidin-1-yl]-xanthine in 5 ml of methanol. The reaction mixture is stirred for two hours at ambient temperature, then a further 150 µl of 1 M sodium methoxide solution are added. After another two hours the reaction to form the iminoester is complete and the reaction mixture is neutralised with 1 M acetic acid in methanol. Then a solution of 130 mg of 2-methylaminomethyl-phenylamine in 3 ml of methanol is added and the reaction mixture is refluxed for three hours. Then the methanol is distilled off and the residue is stirred with water, suction filtered and dried.

Yield: 250 mg (50% of theory)
Mass spectrum (ESI$^+$): m/z=575 [M+H]$^+$
The following compound is obtained analogously to Example XIX:

(1) 1-[(1H-perimidin-2-yl)methyl]-3-methyl-7-(2-butyn-1-yl)-8-[(R)-3-(tert.-butyloxycarbonyl-amino)-piperidin-1-yl]-xanthine Mass spectrum (ESI$^+$): m/z=597 [M+H]$^+$

EXAMPLE XX

3-Cyclopropyl-8-bromo-xanthine 1.08 ml bromine are slowly added dropwise to a mixture of 3.67 g of 3-cyclopropyl-xanthine and 3.40 g potassium carbonate in 60 ml acetonitrile at an oil bath temperature of 60° C. The reaction mixture is stirred for six hours at this temperature, then a further 100 µl bromine are added. After another three hours the acetonitrile is distilled off in vacuo and the residue is dissolved in 100 ml of water. Then 10 ml of saturated sodium thiosulphate solution are added and the mixture is extracted with ethyl acetate. The aqueous phase is acidified with 1 M hydrochloric acid, whereupon a fine precipitate is formed. The precipitate is suction filtered, washed with water and diethyl ether and dried at 80*C in the circulating air dryer.

Yield: 3.36 g (65% of theory)
$R^f$ value: 0.65 (Reversed phase ready-made TLC plate (E. Merck), acetonitrile/water/trifluoroacetic acid=50:50:1)
Mass spectrum (ESI$^+$): m/z=271, 273 [M+H]$^+$

EXAMPLE XXI

6-Chloromethyl-8-methyl-phenanthridine 600 g of 2-chloro-N-(4'-methyl-biphenyl-2-yl)-acetamide are heated in 3 ml phosphorus oxychloride to 100° C. for about 6 hours. Then the phosphorus oxychloride is distilled off. The residue is suspended in water and ethyl acetate and neutralised with 3 M sodium hydroxide solution wherein cooling with an ice bath. The aqueous phase is extracted with ethyl acetate and the combined organic phases are washed with saturated sodium chloride solution, dried over magnesium sulphate and evaporated down. The residue is triturated with diisopropylether, suction filtered and dried.

Yield: 160 mg (29% of theory)
$R_f$ value: 0.45 (silica gel, cyclohexane/ethyl acetate=1:1)
Mass spectrum (ESI$^+$): m/z=242, 244 [M+H]$^+$
The following compounds are obtained analogously to Example XXI:

(1) 6-chloromethyl-1-methyl-phenanthridine
Mass spectrum (ESI$^+$): m/z=242, 244 [M+H]$^+$ (2) 6-chloromethyl-4-methyl-phenanthridine
Mass spectrum (ESI$^+$): m/z=242, 244 [M+H]$^+$

EXAMPLE XXII

1-[(indolizin-2-yl)methyl-3-methyl-7-(2-butyn-1-yl)-8-bromo-xanthine 0.61 ml of diisopropyl azodicarboxylate are added to a mixture of 594 mg of 3-methyl-7-(2-butyn-1-yl)-8-bromo-xanthine, 353 mg of (indolizin-2-yl)-methanol and 826 mg of triphenylphosphine in 30 ml of tetrahydrofuran. The reaction mixture is stirred for two hours at ambient temperature. For working up it is diluted with methylene chloride, added to 6 g silica gel and chromatographed through a silica gel column with petroleum ether/ethyl acetate (7:3 to 1:5) as eluant.

Yield: 405 mg (48% of theory)
$R_f$ value: 0.62 (silica gel, petroleum ether/ethyl acetate=1:1)
Mass spectrum (ESI$^+$): m/z=426, 428 [M+H]$^+$

EXAMPLE XXIII

6-Methyl-benzo[c][1,8]naphthyridine 8.7 ml glycerol and 4.38 g 3-amino-1-methyl-isoquinoline are added to a mixture of 960 mg of iron(II)sulphate-heptahydrate, 12.00 g of 3-nitro-benzosulphonic acid sodium salt, 15 ml of conc. sulphuric acid and 1.70 g of boric acid wherein cooling in the ice bath. The viscous, sticky mass is heated to approx. 55° C., combined with 15 ml of water and then stirred for three hours at 140° C. The cooled reaction mixture is diluted with some ice, made alkaline with 15 N sodium hydroxide solution wherein cooling with an ice bath and extracted with methylene chloride. The combined organic phases are washed with saturated sodium chloride solution, dried over magnesium sulphate and evaporated down. The flask residue is chromatographed through a silica gel column with ethyl acetate/methanol (99:1 to 94:6) as eluant. The crude product thus obtained is stirred with tert.-butylmethylether and some ethyl acetate, suction filtered and dried.

Yield: 2.05 g (38% of theory)
$R_f$ value: 0.15 (silica gel, ethyl acetate)
Mass spectrum (ESI$^+$): m/z=195 [M+H]$^+$ The following compound is obtained analogously to Example XXIII:

(1) 6-methyl-benzo[c][1,5]naphthyridine
$R_f$ value: 0.52 (silica gel, methylene chloride/methanol=95:5)
Mass spectrum (ESI$^+$): m/z=195 [M+H]$^+$

EXAMPLE XXIV 6-methyl-benzo[f]quinoxaline
170 mg of 4-methyl-naphthalene-1,2-diamine and 114 µl of glyoxal are stirred in a mixture of 2 ml of water and 2 ml of ethanol for half an hour at 75° C. For working up the cooled reaction mixture is diluted with methylene chloride and water. The organic phase is washed with saturated sodium chloride solution, dried over magnesium sulphate and evaporated down. The crude product is purified by chromatography over a silica gel column with methylene chloride/methanol (100:0 to 99:1) as eluant.

Yield: 140 mg (73% of theory)
$R_f$ value: 0.84 (silica gel, ethyl acetate)
Mass spectrum (ESI$^+$): m/z=195 [M+H]$^+$

EXAMPLE XXV 2-chloromethyl-imidazo[2,1-a]isoquinoline
1.47 g of 1-amino-isoquinoline and 635 mg of 1,3-dichloroacetone are refluxed for one hour in 10 ml acetonitrile. For working up the reaction mixture is combined with methanol, added to approx. 5 g silica gel and chromatographed through a silica gel column with methylene chloride/methanol (98:2 to 96:4) as eluant.

Yield: 420 mg (39% of theory)
$R_f$ value: 0.65 (silica gel, methylene chloride/methanol=95:5)
Mass spectrum (ESI$^+$): m/z=217, 219 [M+H]$^+$ The following compound is obtained analogously to Example XXV:

(1) 2-chloromethyl-imidazo[1,2-a]isoquinoline
$R_f$ value: 0.64 (silica gel, methylene chloride/methanol=95:5)
Mass spectrum (ESI$^+$): m/z=217, 219 [M+H]$^+$ Preparation of the final compounds:

EXAMPLE 1

1-[(1-methyl-2,2-dioxo-1H-benzo[c][1,2]thiazin-4-yl)methyl]-3-methyl-7-(3-methyl-2-buten-1-yl)-8-(3-amino-piperidin-1-yl)-xanthine 3.5 ml isopropanolic hydrochloric acid (5-6 M) are added to 340 mg of 1-[(1-methyl-2,2-dioxo-1H-benzo[c][1,2]thiazin-4-yl)methyl]-3-methyl-7-(3-methyl-2-buten-1-yl)-8-[3-(tert.-butyloxycarbonylamino)-piperidin-1-yl]-xanthine in 15 ml methylene chloride and the reaction mixture is stirred for three hours at ambient temperature. For working up it is diluted with water and methylene chloride and combined with 18 ml 1N sodium hydroxide solution. The aqueous phase is extracted with methylene chloride and the combined organic phases are washed with water, dried over magnesium sulphate and evaporated down. The yellowish, foamy flask residue is stirred with tert.-butyl-methylether and a little diethyl ether, the light-coloured precipitate formed is suction filtered and dried at 60° C. in the drying gun.

Yield: 220 mg (77% of theory)
melting point: 205-208° C. (decomposition)
Mass spectrum (ESI$^+$): m/z=540 [M+H]$^+$ The following compounds are obtained analogously to Example 1:

(1) 1-[(3-methoxycarbonyl-3-methyl-3,4-dihydro-isoquinolin-1-yl]methyl]-3-methyl-7-(2-butyn-1-yl)-8-(3-amino-piperidin-1-yl)-xanthine

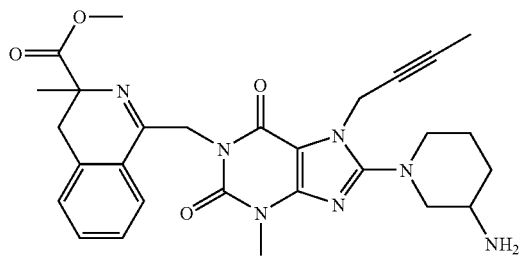

$R_f$ value: 0.42 (silica gel, methylene chloride/methanol/conc. aqueous ammonia=90:10:1)
Mass spectrum (ESI$^+$): m/z=532 [M+H]$^+$ (2) 1-[(2-oxo-2,3-dihydro-1H-benzo[e][1,4]diazepin-5-yl)methyl]-3-methyl-7-((E)-2-buten-1-yl)-8-((R)-3-amino-piperidin-1-yl)-xanthine

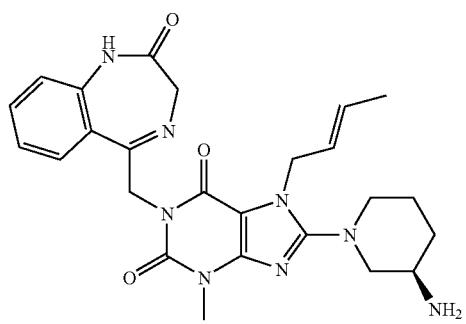

(carried out with trifluoroacetic acid in methylene chloride)
$R_f$ value: 0.50 (Reversed phase ready-made TLC plate (E. Merck), acetonitrile/water/trifluoroacetic acid=50:50:0.1)
Mass spectrum (ESI$^+$): m/z=491 [M+H]$^+$

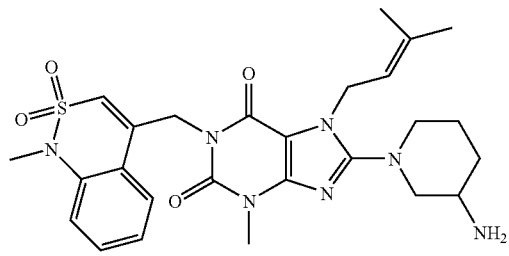

(3) 1-[(phenanthridin-6-yl)methyl]-3-methyl-7-(2-butyn-1-yl)-8-(3-amino-piperidin-1-yl)-xanthine-dihydrochloride

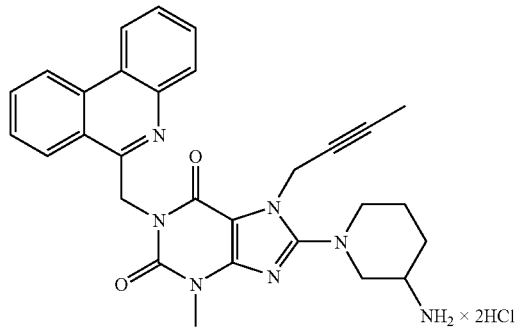

$R_f$ value: 0.55 (Reversed phase ready-made TLC plate (E. Merck), acetonitrile/water/trifluoroacetic acid=50:50:1)

Mass spectrum (ESI$^+$): m/z=508 [M+H]$^+$ (4) 1-[(1,2,3,4-tetrahydro-phenanthridin-6-yl)methyl]-3-methyl-7-(2-butyn-1-yl)-8-(3-amino-piperidin-1-yl)-xanthine x trifluoroacetic acid

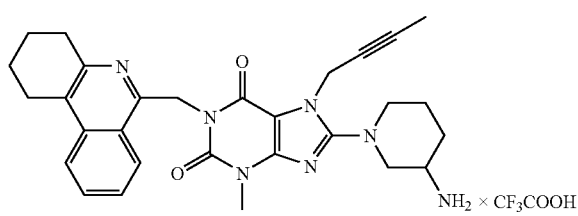

(carried out with trifluoroacetic acid in methylene chloride)

$R_f$ value: 0.75 (aluminium oxide, methylene chloride/methanol=10:1)

Mass spectrum (ESI$^+$): m/z=512 [M+H]$^+$ (5) 1-[(1H-dibenzo[b,e]azepin-6-yl)methyl]-3-methyl-7-(2-butyn-1-yl)-8-(3-amino-piperidin-1-yl)-xanthine

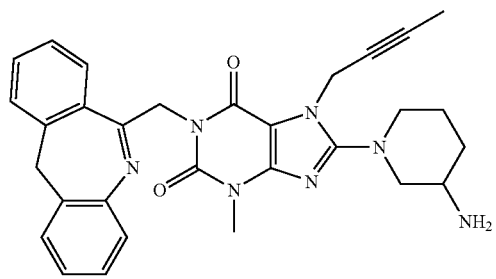

$R_f$ value: 0.45 (Reversed phase ready-made TLC plate (E. Merck), acetonitrile/water/trifluoroacetic acid=50:50:1)

Mass spectrum (ESI$^+$): m/z=522 [M+H]$^+$ (6) 1-[(dibenzo[b,f][1,4]oxazepin-11-yl)methyl]-3-methyl-7-(2-butyn-1-yl)-8-(3-amino-piperidin-1-yl)-xanthine

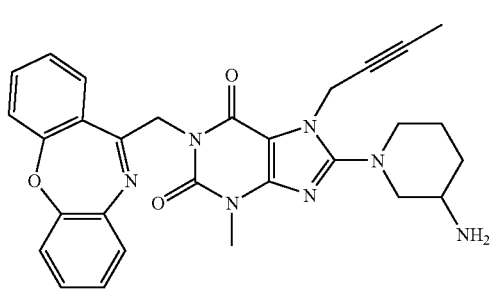

Mass spectrum (ESI$^+$): m/z=524 [M+H]$^+$ (7) 1-[(3-trifluoromethyl-3,4-dihydro-isoquinolin-1-yl)methyl]-3-methyl-7-(2-butyn-1-yl)-8-(3-amino-piperidin-1-yl)-xanthine x trifluoroacetic acid

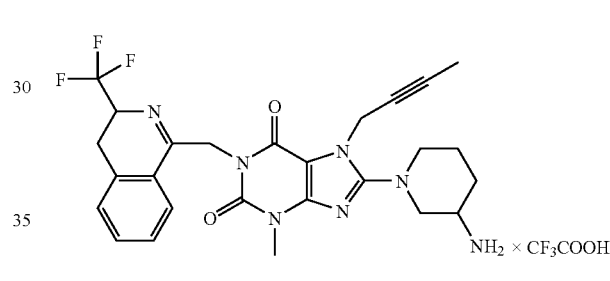

(carried out with trifluoroacetic acid in methylene chloride)

$R_f$ value: 0.30 (silica gel, methylene chloride/methanol=10:1)

Mass spectrum (ESI$^+$): m/z=528 [M+H]$^+$ (8) 1-[(dibenzo[b,f][1,4]oxazepin-11-yl)methyl]-3-methyl-7-(2-butyn-1-yl)-8-((R)-3-amino-piperidin-1-yl)-xanthine

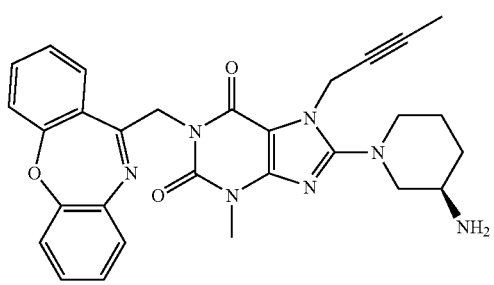

Mass spectrum (ESI$^+$): m/z=524 [M+H]$^+$
melting point: 128° C.

(9) 1-[(3,3-dimethyl-3,4-dihydro-isoquinolin-1-yl)methyl]-3-methyl-7-(2-butyn-1-yl)-8-(3-amino-piperidin-1-yl)-xanthine

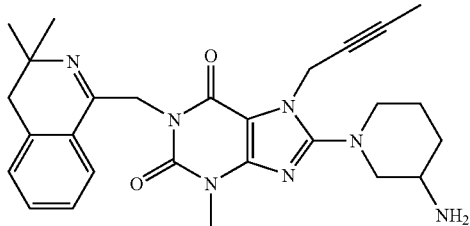

R$_f$ value: 0.55 (Reversed phase ready-made TLC plate (E. Merck), acetonitrile/water/trifluoroacetic acid=50:50:1)

Mass spectrum (ESI$^+$): m/z=488 [M+H]$^+$

(10) 1-[(3,4-dihydro-quinazolin-2-yl)methyl]-3-methyl-7-(2-butyn-1-yl)-8-(3-amino-piperidin-1-yl)-xanthine

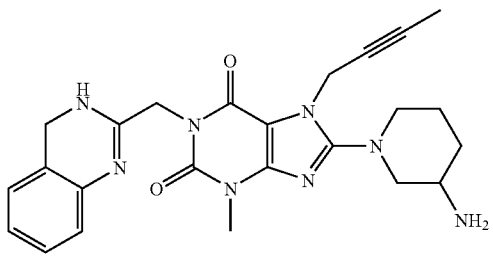

(carried out with trifluoroacetic acid in methylene chloride)

Mass spectrum (ESI$^+$): m/z=461 [M+H]$^+$

(11) 1-[(3-methyl-3,4-dihydro-quinazolin-2-yl)methyl]-3-methyl-7-(2-butyn-1-yl)-8-(3-amino-piperidin-1-yl)-xanthine x trifluoroacetic acid

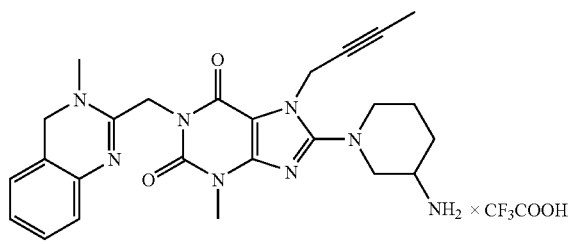

(carried out with trifluoroacetic acid in methylene chloride)

Mass spectrum (ESI$^+$): m/z=475 [M+H]$^+$

(12) 1-[(5-methyl-5H-dibenzo[b,e][1,4]diazepin-11-yl)methyl]-3-methyl-7-(2-butyn-1-yl)-8-(3-amino-piperidin-1-yl)-xanthine

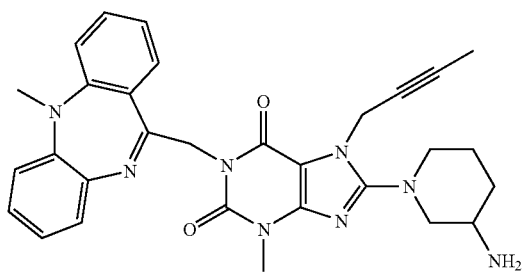

R$_f$ value: 0.45 (Reversed phase ready-made TLC plate (E. Merck), acetonitrile/water/trifluoroacetic acid=50:50:1)

Mass spectrum (ESI$^+$): m/z=537 [M+H]$^+$

(13) 1-[(8-methyl-dibenzo[b,f][1,4]oxazepin-11-yl)methyl]-3-methyl-7-(2-butyn-1-yl)-8-(3-amino-piperidin-1-yl)-xanthine

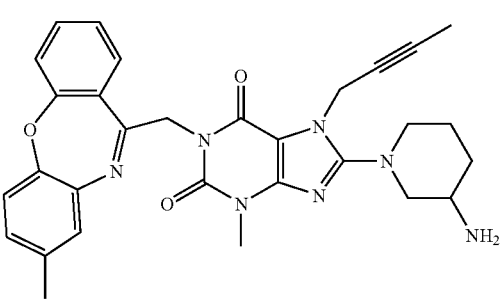

R$_f$ value: 0.60 (Reversed phase ready-made TLC plate (E. Merck), acetonitrile/water/trifluoroacetic acid=50:50:1)

Mass spectrum (ESI$^+$): m/z=538 [M+H]$^+$

(14) 1-[(2-methyl-dibenzo[b,f][1,4]oxazepin-11-yl)methyl]-3-methyl-7-(2-butyn-1-yl)-8-(3-amino-piperidin-1-yl)-xanthine

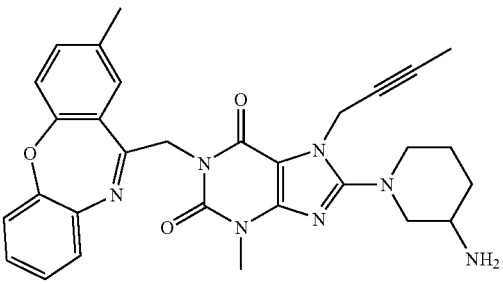

R$_f$ value: 0.55 (Reversed phase ready-made TLC plate (E. Merck), acetonitrile/water/trifluoroacetic acid=50:50:1)

Mass spectrum (ESI$^+$): m/z=538 [M+H]$^+$

(15) 1-[(benzo[1,2,5]oxadiazol-5-yl)methyl]-3-methyl-7-(2-butyn-1-yl)-8-(3-amino-piperidin-1-yl)-xanthine

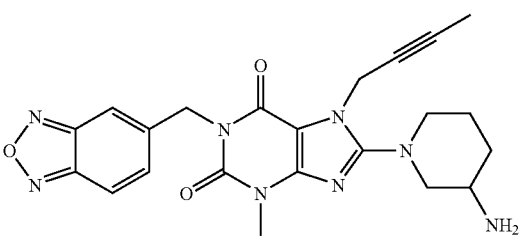

R$_f$ value: 0.38 (silica gel, methylene chloride/methanol=9:1)

Mass spectrum (ESI$^+$): m/z=449 [M+H]$^+$

(16) 1-[(2-chloro-dibenzo[b,f][1,4]oxazepin-11-yl)methyl]-3-methyl-7-(2-butyn-1-yl)-8-(3-amino-piperidin-1-yl)-xanthine

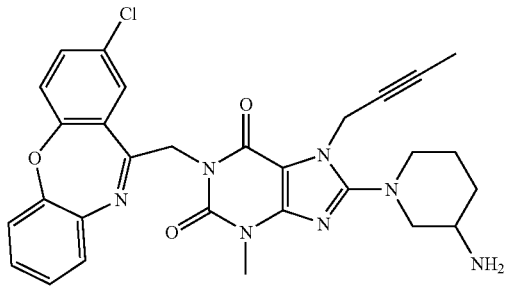

R$_f$ value: 0.50 (Reversed phase ready-made TLC plate (E. Merck), acetonitrile/water/trifluoroacetic acid=50:50:1)

Mass spectrum (ESI$^+$): m/z=558, 560 [M+H]$^+$

(17) 1-[(phenanthridin-6-yl)methyl]-3-cyclopropyl-7-(2-butyn-1-yl)-8-(3-amino-piperidin-1-yl)-xanthine

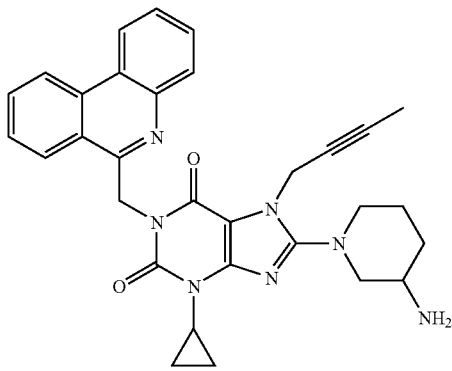

R$_f$ value: 0.50 (Reversed phase ready-made TLC plate (E. Merck), acetonitrile/water/trifluoroacetic acid=50:50:1)

Mass spectrum (ESI$^+$): m/z=534 [M+H]$^+$

(18) 1-[(8-methyl-phenanthridin-6-yl)methyl]-3-methyl-7-(2-butyn-1-yl)-8-(3-amino-piperidin-1-yl)-xanthine

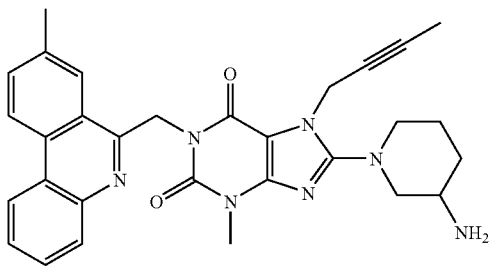

melting point: 200-205° C.

Mass spectrum (ESI$^+$): m/z=522 [M+H]$^+$

(19) 1-[(phenanthridin-6-yl)methyl]-3-methyl-7-(2-butyn-1-yl)-8-((S)-3-amino-piperidin-1-yl)-xanthine

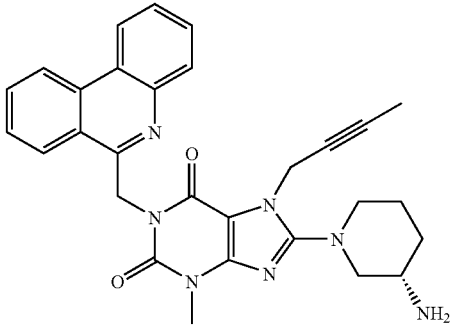

R$_f$ value: 0.55 (Reversed phase ready-made TLC plate (E. Merck), acetonitrile/water/trifluoroacetic acid=50:50:1)

Mass spectrum (ESI$^+$): m/z=508 [M+H]$^+$

(20) 1-[(phenanthridin-6-yl)methyl]-3-cyclopropyl-7-(2-butyn-1-yl)-8-((R)-3-amino-piperidin-1-yl)-xanthine

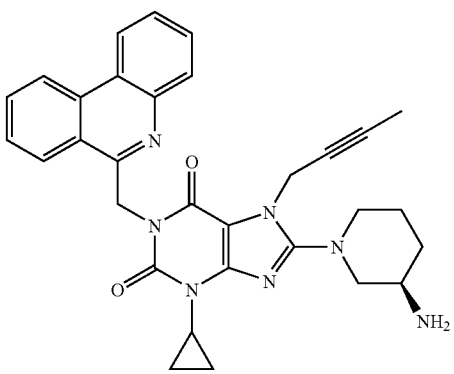

R$_f$ value: 0.50 (Reversed phase ready-made TLC plate (E. Merck), acetonitrile/water/trifluoroacetic acid=50:50:1)

Mass spectrum (ESI$^+$): m/z=534 [M+H]$^+$

(21) 1-[(dibenzofuran-2-yl)methyl]-3-methyl-7-(2-butyn-1-yl)-8-((R)-3-amino-piperidin-1-yl)-xanthine

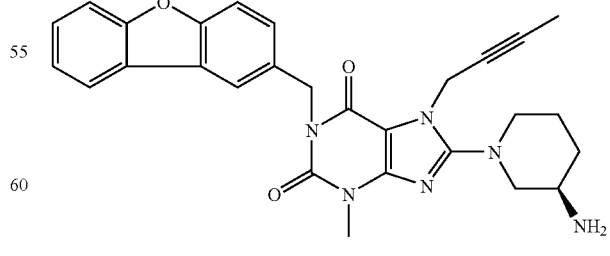

R$_f$ value: 0.40 (Reversed phase ready-made TLC plate (E. Merck), acetonitrile/water/trifluoroacetic acid=50:50:1)

Mass spectrum (ESI$^+$): m/z=497 [M+H]$^+$

(22) 1-[(1-methyl-phenanthridin-6-yl)methyl]-3-methyl-7-(2-butyn-1-yl)-8-((R)-3-amino-piperidin-1-yl)-xanthine

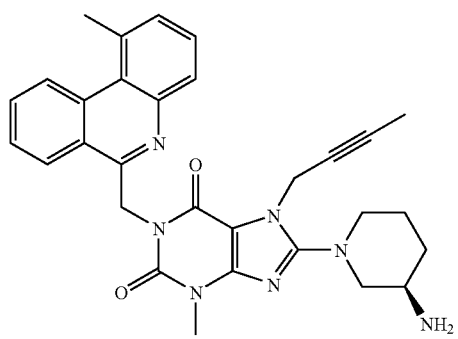

R$_f$ value: 0.50 (Reversed phase ready-made TLC plate (E. Merck), acetonitrile/water/trifluoroacetic acid=50:50:1)

Mass spectrum (ESI$^+$): m/z=522 [M+H]$^+$

(23) 1-[(4-methyl-phenanthridin-6-yl)methyl]-3-methyl-7-(2-butyn-1-yl)-8-((R)-3-amino-piperidin-1-yl)-xanthine

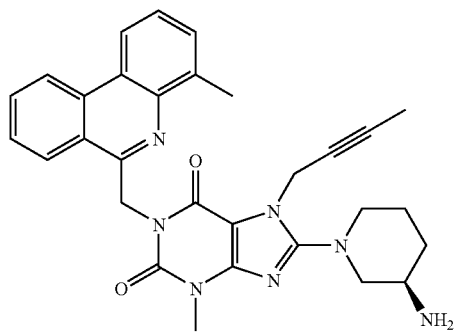

R$_f$ value: 0.40 (Reversed phase ready-made TLC plate (E. Merck), acetonitrile/water/trifluoroacetic acid=50:50:1)

Mass spectrum (ESI$^+$): m/z=522 [M+H]$^+$

(24) 1-[(indolizin-2-yl)methyl]-3-methyl-7-(2-butyn-1-yl)-8-(3-amino-piperidin-1-yl)-xanthine

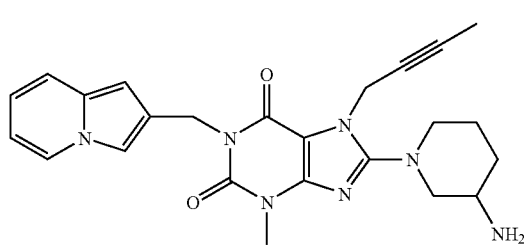

R$_f$ value: 0.47 (silica gel, methylene chloride/methanol/conc. aqueous ammonia=90:10:1)

Mass spectrum (ESI$^+$): m/z=446 [M+H]$^+$

(25) 1-[(benzo[h][1,6]naphthyridin-5-yl)methyl]-3-methyl-7-(2-butyn-1-yl)-8-(3-amino-piperidin-1-yl)-xanthine

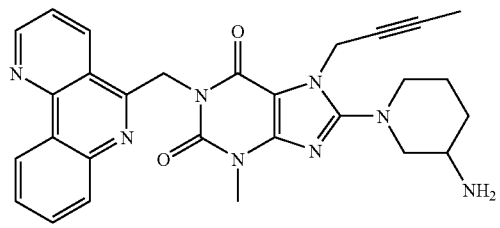

R$_f$ value: 0.49 (silica gel, methylene chloride/methanol/conc. aqueous ammonia=90:10:1)

Mass spectrum (ESI$^+$): m/z=509 [M+H]$^+$

(26) 1-[(pyrazolo[1,5-c]quinazolin-5-yl)methyl]-3-methyl-7-(2-butyn-1-yl)-8-(3-amino-piperidin-1-yl)-xanthine

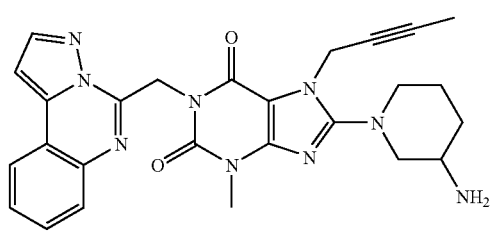

R$_f$ value: 0.46 (silica gel, methylene chloride/methanol/conc. aqueous ammonia=90:10:1)

Mass spectrum (ESI$^+$): m/z=498 [M+H]$^+$

(27) 1-[(benzo[c][1,8]naphthyridin-6-yl)methyl]-3-methyl-7-(2-butyn-1-yl)-8-(3-amino-piperidin-1-yl)-xanthine

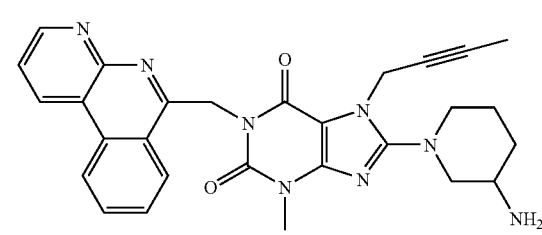

R$_f$ value: 0.48 (silica gel, methylene chloride/methanol/conc. aqueous ammonia=90:10:1)

Mass spectrum (ESI$^+$): m/z=509 [M+H]$^+$

(28) 1-[(benzo[c][1,5]naphthyridin-6-yl)methyl]-3-methyl-7-(2-butyn-1-yl)-8-((R)-3-amino-piperidin-1-yl)-xanthine

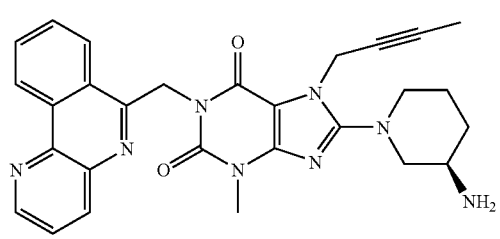

R$_f$ value: 0.51 (silica gel, methylene chloride/methanol/conc. aqueous ammonia=90:10:1)

Mass spectrum (ESI$^+$): m/z=509 [M+H]$^+$

(29) 1-[(1H-perimidin-2-yl)methyl]-3-methyl-7-(2-butyn-1-yl)-8-((R)-3-amino-piperidin-1-yl)-xanthine

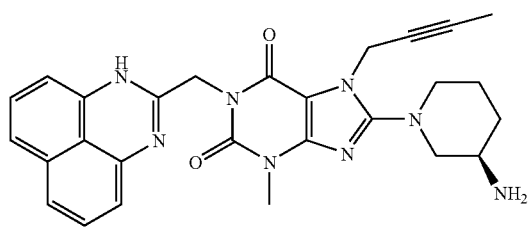

R$_f$ value: 0.47 (silica gel, methylene chloride/methanol/conc. aqueous ammonia=90:10:1)

Mass spectrum (ESI$^+$): m/z=497 [M+H]$^+$

(30) 1-[(benzo[f]quinoxalin-6-yl)methyl]-3-methyl-7-(2-butyn-1-yl)-8-((R)-3-amino-piperidin-1-yl)-xanthine

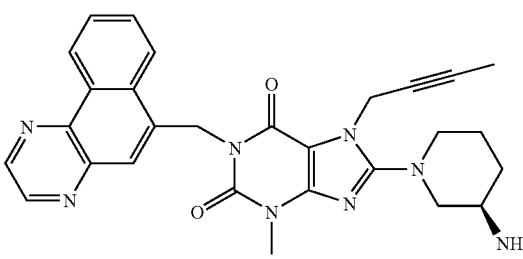

R$_f$ value: 0.50 (silica gel, methylene chloride/methanol/conc. aqueous ammonia=90:10:1)

Mass spectrum (ESI$^+$): m/z=509 [M+H]$^+$

(31) 1-[(imidazo[2,1-a]isoquinolin-2-yl)methyl]-3-methyl-7-(2-butyn-1-yl)-8-(3-amino-piperidin-1-yl)-xanthine

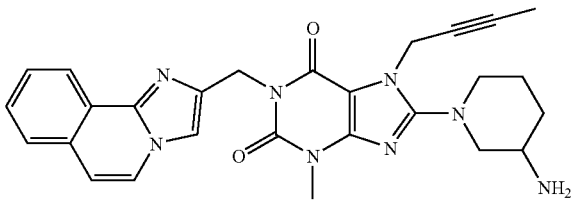

R$_f$ value: 0.54 (silica gel, methylene chloride/methanol/conc. aqueous ammonia=90:10:1)

Mass spectrum (ESI$^+$): m/z=497 [M+H]$^+$

(32) 1-[(imidazo[1,2-a]isoquinolin-2-yl)methyl]-3-methyl-7-(2-butyn-1-yl)-8-(3-amino-piperidin-1-yl)-xanthine

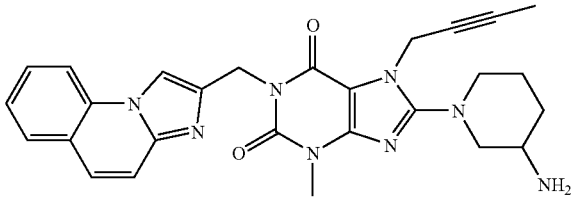

melting point: 194-198.5° C.

Mass spectrum (ESI$^+$): m/z=497 [M+H]$^+$

(33) 1-[(phenanthridin-6-yl)methyl]-3-methyl-7-(2-butyn-1-yl)-8-((R)-3-amino-piperidin-1-yl)-xanthine

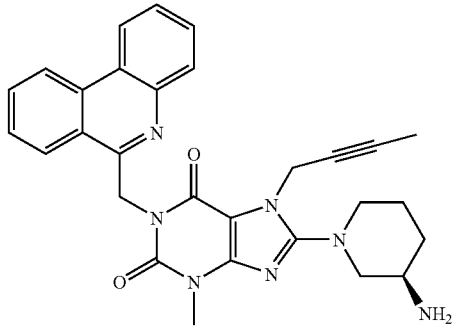

R$_f$ value: 0.55 (Reversed phase ready-made TLC plate (E. Merck), acetonitrile/water/trifluoroacetic acid=50:50:1)

Mass spectrum (ESI$^+$): m/z=508 [M+H]$^+$

EXAMPLE 2

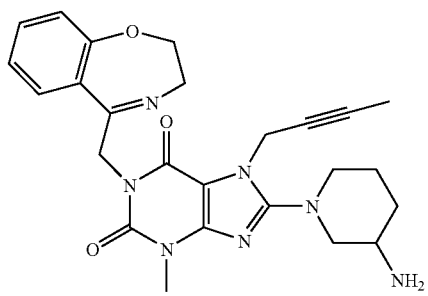

1-[(2,3-dihydro-benzo[f][1,4]oxazepin-5-yl)methyl]-3-methyl-7-(2-butyn-1-yl)-8-(3-amino-piperidin-1-yl)-xanthine 1.15 ml trifluoroacetic acid are added to 368 mg of 1-(2-{2-[2-(tert.-butyloxycarbonylamino)-ethoxy]-phenyl}-2-oxo-ethyl)-3-methyl-7-(2-butyn-1-yl)-8-[3-(tert.-butyloxycarbonyl-amino)-piperidin-1-yl]-xanthine in 7 ml methylene chloride wherein cooling with an ice bath. The reaction mixture is stirred for about three hours at ambient temperature and then added to cooled potassium carbonate solution. The organic phase is washed with saturated sodium chloride solution, dried over magnesium sulphate and evaporated down. The crude product is purified through a silica gel column with methylene chloride/methanol (10:0 to 7:3) as eluant.

Yield: 75 mg (30% of theory)

R$_f$ value: 0.20 (silica gel, methylene chloride/methanol=9:1)

Mass spectrum (ESI$^+$): m/z=476 [M+H]$^+$

EXAMPLE 3

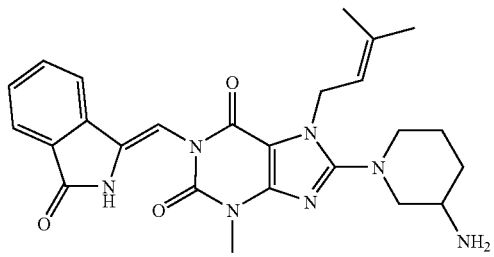

1-[(3-oxo-2,3-dihydro-isoindol-1-ylidene)methyl]-3-methyl-7-(3-methyl-2-buten-1-yl)-8-(3-amino-piperidin-1-yl)-xanthine 150 mg of 1-[(1-hydroxy-3-oxo-2,3-dihydro-1H-isoindol-1-yl)methyl]-3-methyl-7-(3-methyl-2-buten-1-yl)-8-[3-(tert.-butyloxycarbonyl-amino)-piperidin-1-yl]-xanthine are stirred for four hours in a mixture of 0.4 ml trifluoroacetic acid and 1.2 ml methylene chloride. For working up the reaction mixture is diluted with 30 ml methylene chloride, combined with 10 ml 10% potassium carbonate solution and stirred vigorously. The organic phase is separated off, dried over magnesium sulphate and evaporated down.

Yield: 50 mg (42% of theory)

$R_f$ value: 0.56 (Reversed phase ready-made TLC plate (E. Merck), acetonitrile/water/trifluoroacetic acid=50:50:1)

Mass spectrum (ESI$^+$): m/z=476 [M+H]$^+$

The following compounds may also be obtained analogously to the foregoing Examples and other methods known from the literature:

| No. | Name | Structural formula |
|---|---|---|
| (1) | 1-[(1-methyl-1,4-dihydro-quinazolin-2-yl)methyl]-3-methyl-7-(2-butyn-1-yl)-8-(3-amino-piperidin-1-yl)-xanthine | |
| (2) | 1-[(3,4-dihydro-quinazolin-2-yl)methyl]-3-methyl-7-(2-butyn-1-yl)-8-(3-amino-piperidin-1-yl)-xanthine | |
| (3) | 1-[(3-methyl-3,4-dihydro-quinazolin-2-yl)methyl]-3-methyl-7-(2-butyn-1-yl)-8-(3-amino-piperidin-1-yl)-xanthine | |
| (4) | 1-[(3,4-dihydro-isoquinolin-1-yl)methyl]-3-methyl-7-(2-butyn-1-yl)-8-(3-amino-piperidin-1-yl)-xanthine | |
| (5) | 1-[(3,3-dimethyl-3,4-dihydro-isoquinolin-1-yl)methyl]-3-methyl-7-(2-butyn-1-yl)-8-(3-amino-piperidin-1-yl)-xanthine | |
| (6) | 1-[(4,4-dimethyl-3,4-dihydro-isoquinolin-1-yl)methyl]-3-methyl-7-(2-butyn-1-yl)-8-(3-amino-piperidin-1-yl)-xanthine | |

-continued

| No. | Name | Structural formula |
|---|---|---|
| (7) | 1-[(1H-benzo[d][1,2]oxazin-4-yl)methyl]-3-methyl-7-(2-butyn-1-yl)-8-(3-amino-piperidin-1-yl)-xanthine | |
| (8) | 1-[(1-oxo-1H-benzo[d][1,2]oxazin-4-yl)methyl]-3-methyl-7-(2-butyn-1-yl)-8-(3-amino-piperidin-1-yl)-xanthine | |
| (9) | 1-[(4H-benzo[e][1,3]oxazin-2-yl)methyl]-3-methyl-7-(2-butyn-1-yl)-8-(3-amino-piperidin-1-yl)-xanthine | |
| (10) | 1-[(4,4-dimethyl-4H-benzo[e][1,3]oxazin-2-yl)methyl]-3-methyl-7-(2-butyn-1-yl)-8-(3-amino-piperidin-1-yl)-xanthine | |
| (11) | 1-[(4-oxo-4H-benzo[e][1,3]oxazin-2-yl)methyl]-3-methyl-7-(2-butyn-1-yl)-8-(3-amino-piperidin-1-yl)-xanthine | |
| (12) | 1-[(4H-benzo[d][1,3]oxazin-2-yl)methyl]-3-methyl-7-(2-butyn-1-yl)-8-(3-amino-piperidin-1-yl)-xanthine | |
| (13) | 1-[(4,4-dimethyl-4H-benzo[d][1,3]oxazin-2-yl)methyl]-3-methyl-7-(2-butyn-1-yl)-8-(3-amino-piperidin-1-yl)-xanthine | |

| No. | Name | Structural formula |
|---|---|---|
| (14) | 1-[(4-oxo-4H-benzo[d][1,3]oxazin-2-yl)methyl]-3-methyl-7-(2-butyn-1-yl)-8-(3-amino-piperidin-1-yl)-xanthine | |
| (15) | 1-[(2H-benzo[1,4]oxazin-3-yl)methyl]-3-methyl-7-(2-butyn-1-yl)-8-(3-amino-piperidin-1-yl)-xanthine | |
| (16) | 1-[(2-oxo-2H-benzo[1,4]oxazin-3-yl)methyl]-3-methyl-7-(2-butyn-1-yl)-8-(3-amino-piperidin-1-yl)-xanthine | |
| (17) | 1-[(2,2-dimethyl-2H-benzo[1,4]oxazin-3-yl)methyl]-3-methyl-7-(2-butyn-1-yl)-8-(3-amino-piperidin-1-yl)-xanthine | |
| (18) | 1-[4H-benzo[e][1,3]thiazin-2-yl)methyl]-3-methyl-7-(2-butyn-1-yl)-8-(3-amino-piperidin-1-yl)-xanthine | |
| (19) | 1-[4,4-dimethyl-4H-benzo[e][1,3]thiazin-2-yl)methyl]-3-methyl-7-(2-butyn-1-yl)-8-(3-amino-piperidin-1-yl)-xanthine | |
| (20) | 1-[4-oxo-4H-benzo[e][1,3]thiazin-2-yl)methyl]-3-methyl-7-(2-butyn-1-yl)-8-(3-amino-piperidin-1-yl)-xanthine | |

| No. | Name | Structural formula |
|---|---|---|
| (21) | 1-[(4H-benzo[d][1,3]thiazin-2-yl)methyl]-3-methyl-7-(2-butyn-1-yl)-8-(3-amino-piperidin-1-yl)-xanthine | 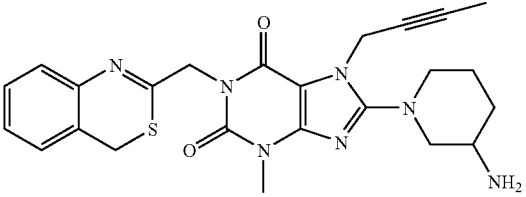 |
| (22) | 1-[(2H-benzo[1,4]thiazin-3-yl)methyl]-3-methyl-7-(2-butyn-1-yl)-8-(3-amino-piperidin-1-yl)-xanthine | 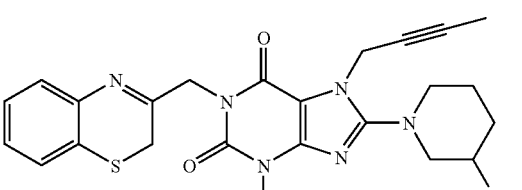 |
| (23) | 1-[(2-oxo-2H-benzo[e][1,3]oxazin-4-yl)methyl]-3-methyl-7-(2-butyn-1-yl)-8-(3-amino-piperidin-1-yl)-xanthine | 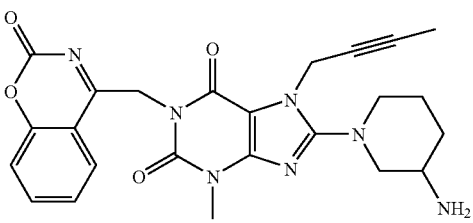 |
| (24) | 1-[(2,3-dihydro-1H-benzo[e][1,4]diazepin-5-yl)methyl]-3-methyl-7-(2-butyn-1-yl)-8-(3-amino-piperidin-1-yl)-xanthine | 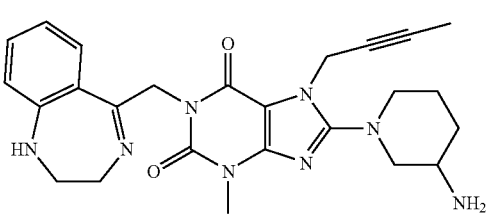 |
| (25) | 1-[(1-methyl-2,3-dihydro-1H-benzo[e][1,4]diazepin-5-yl)methyl]-3-methyl-7-(2-butyn-1-yl)-8-(3-amino-piperidin-1-yl)-xanthine | 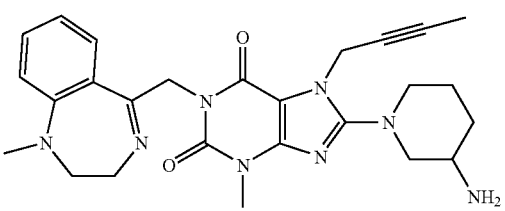 |
| (26) | 1-[(1-methyl-2-oxo-2,3-dihydro-1H-benzo[e][1,4]diazepin-5-yl)methyl]-3-methyl-7-(2-butyn-1-yl)-8-(3-amino-piperidin-1-yl)-xanthine | 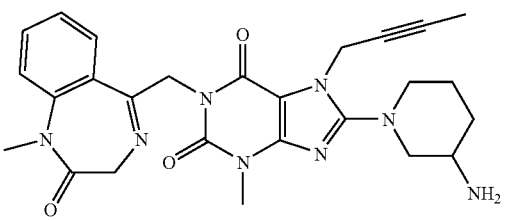 |
| (27) | 1-[(4-oxo-4,5-dihydro-3H-benzo[b][1,4]diazepin-2-yl)methyl]-3-methyl-7-(2-butyn-1-yl)-8-(3-amino-piperidin-1-yl)-xanthine | 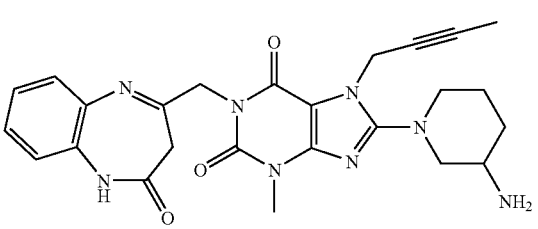 |

-continued

| No. | Name | Structural formula |
|---|---|---|
| (28) | 1-[(5-methyl-4-oxo-4,5-dihydro-3H-benzo[b][1,4]diazepin-2-yl)methyl]-3-methyl-7-(2-butyn-1-yl)-8-(3-amino-piperidin-1-yl)-xanthine | |
| (29) | 1-[5-oxo-4,5-dihydro-3H-benzo[e][1,4]diazepin-2-yl)methyl]-3-methyl-7-(2-butyn-1-yl)-8-(3-amino-piperidin-1-yl)-xanthine | |
| (30) | 1-[4-methyl-5-oxo-4,5-dihydro-3H-benzo[e][1,4]diazepin-2-yl)methyl]-3-methyl-7-(2-butyn-1-yl)-8-(3-amino-piperidin-1-yl)-xanthine | |
| (31) | 1-[(3,3-dimethyl-2,3-dihydro-benzo[f][1,4]oxazepin-5-yl)methyl]-3-methyl-7-(2-butyn-1-yl)-8-(3-amino-piperidin-1-yl)-xanthine | |
| (32) | 1-[(2,2-dimethyl-2,3-dihydro-benzo[f][1,4]oxazepin-5-yl)methyl]-3-methyl-7-(2-butyn-1-yl)-8-(3-amino-piperidin-1-yl)-xanthine | |
| (33) | 1-[(2,3-dihydro-benzo[b][1,4]oxazepin-4-yl)methyl]-3-methyl-7-(2-butyn-1-yl)-8-(3-amino-piperidin-1-yl)-xanthine | |
| (34) | 1-[(6,6-dimethyl-2,3-dihydro-benzo[b][1,4]oxazepin-4-yl)methyl]-3-methyl-7-(2-butyn-1-yl)-8-(3-amino-piperidin-1-yl)-xanthine | |

| No. | Name | Structural formula |
|---|---|---|
| (35) | 1-[(2,3-dihydro-benzo[b][1,4]thiazepin-4-yl)methyl]-3-methyl-7-(2-butyn-1-yl)-8-(3-amino-piperidin-1-yl)-xanthine | 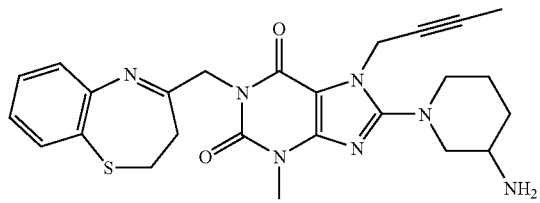 |
| (36) | 1-[(2,2-dimethyl-2,3-dihydro-benzo[b][1,4]thiazepin-4-yl)methyl]-3-methyl-7-(2-butyn-1-yl)-8-(3-amino-piperidin-1-yl)-xanthine | 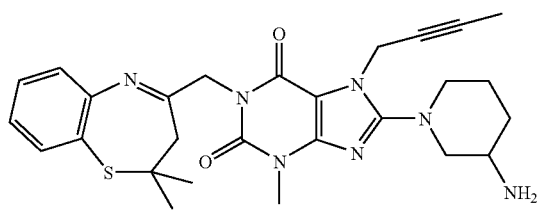 |
| (37) | 1-[(2,3-dihydro-benzo[f][1,4]thiazepin-5-yl)methyl]-3-methyl-7-(2-butyn-1-yl)-8-(3-amino-piperidin-1-yl)-xanthine | 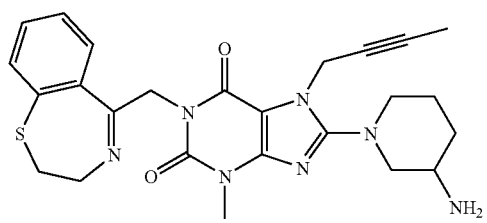 |
| (38) | 1-[(5-oxo-4,5-dihydro-benzo[f][1,3,4]oxadiazepin-2-yl)methyl]-3-methyl-7-(2-butyn-1-yl)-8-(3-amino-piperidin-1-yl)-xanthine | 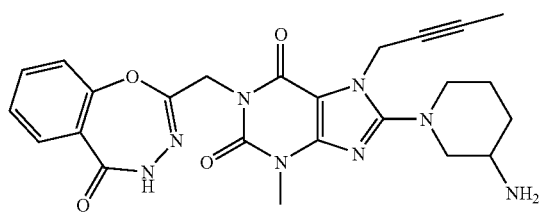 |
| (39) | 1-[(11H-dibenzo[b,e]azepin-6-yl)methyl]-3-ethyl-7-(2-butyn-1-yl)-8-(3-amino-piperidin-1-yl)-xanthine | 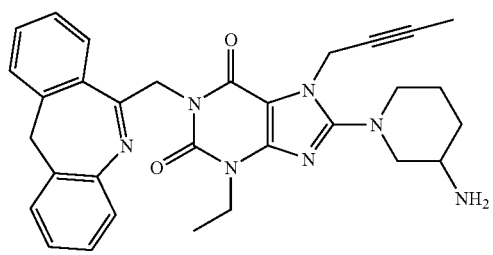 |
| (40) | 1-[(11H-dibenzo[b,e]azepin-6-yl)methyl]-3-isopropyl-7-(2-butyn-1-yl)-8-(3-amino-piperidin-1-yl)-xanthine | 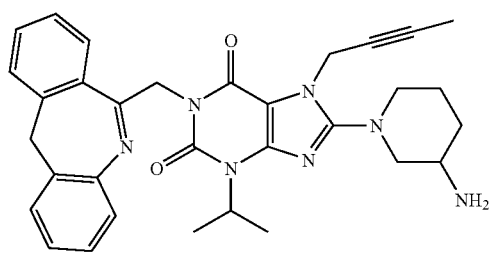 |

| No. | Name | Structural formula |
|---|---|---|
| (41) | 1-[(11-oxo-11H-dibenzo[b,e]azepin-6-yl)methyl]-3-methyl-7-(2-butyn-1-yl)-8-(3-amino-piperidin-1-yl)-xanthine | 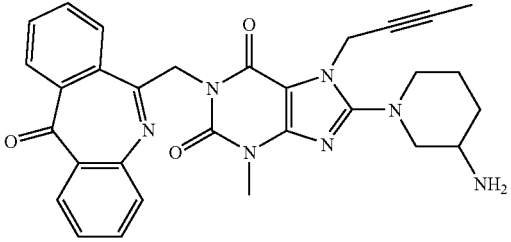 |
| (42) | 1-[(11H-benzo[e]pyrido[3,2-b]azepin-6-yl)methyl]-3-methyl-7-(2-butyn-1-yl)-8-(3-amino-piperidin-1-yl)-xanthine | 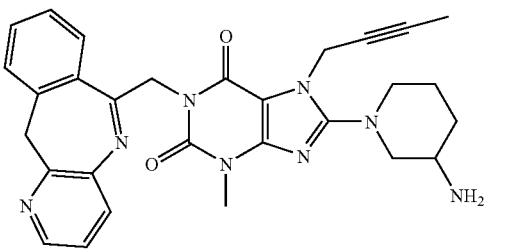 |
| (43) | 1-[(5-methyl-5H-dibenzo[b,e][1,4]diazepin-11-yl)methyl]-3-methyl-7-(2-butyn-1-yl)-8-(3-amino-piperidin-1-yl)-xanthine | 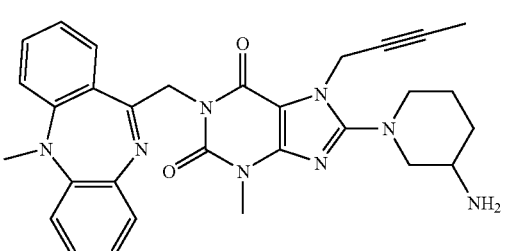 |
| (44) | 1-[(dibenzo[b,f][1,4]thiazepin-11-yl)methyl]-3-methyl-7-(2-butyn-1-yl)-8-(3-amino-piperidin-1-yl)-xanthine | 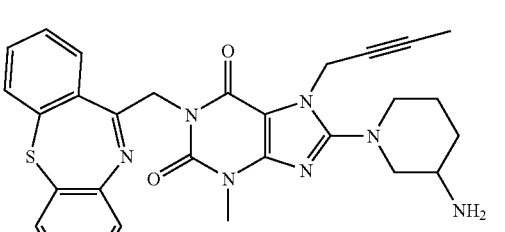 |
| (45) | 1-[(5-oxo-dibenzo[b,f][1,4]thiazepin-11-yl)methyl]-3-methyl-7-(2-butyn-1-yl)-8-(3-amino-piperidin-1-yl)-xanthine | 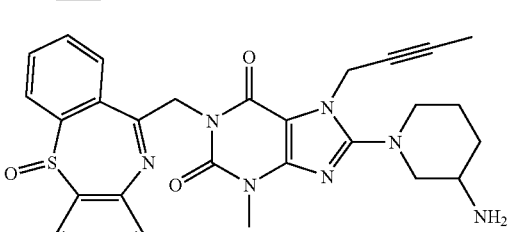 |
| (46) | 1-[(5,5-dioxo-dibenzo[b,f][1,4]thiazepin-11-yl)methyl]-3-methyl-7-(2-butyn-1-yl)-8-(3-amino-piperidin-1-yl)-xanthine | 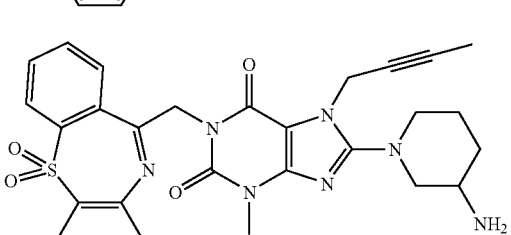 |

-continued

| No. | Name | Structural formula |
|---|---|---|
| (47) | 1-[(5H-dibenzo[a,d]cyclohepten-10-yl)methyl]-3-methyl-7-(2-butyn-1-yl)-8-(3-amino-piperidin-1-yl)-xanthine | 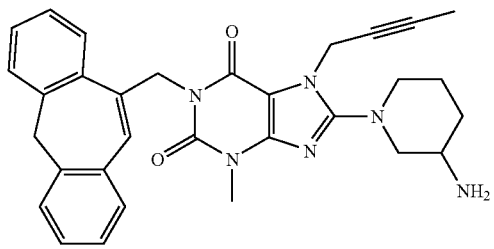 |
| (48) | 1-[(5-methyl-5H-dibenzo[b,f]azepin-10-yl)methyl]-3-methyl-7-(2-butyn-1-yl)-8-(3-amino-piperidin-1-yl)-xanthine | 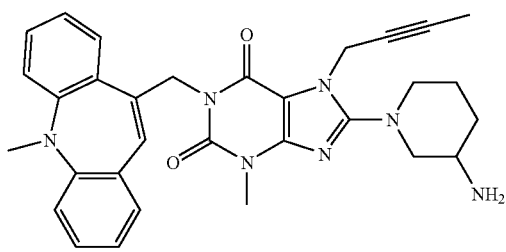 |
| (49) | 1-[(phenanthridin-6-yl)methyl]-3-methyl-7-(3-methyl-2-buten-1-yl)-8-(3-amino-piperidin-1-yl)-xanthine | 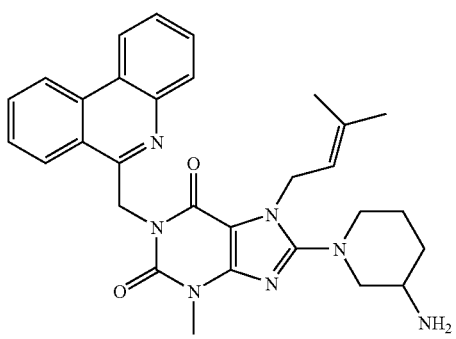 |
| (50) | 1-[(phenanthridin-6-yl)methyl]-3-methyl-7-((E)-2-buten-1-yl)-8-(3-amino-piperidin-1-yl)-xanthine | 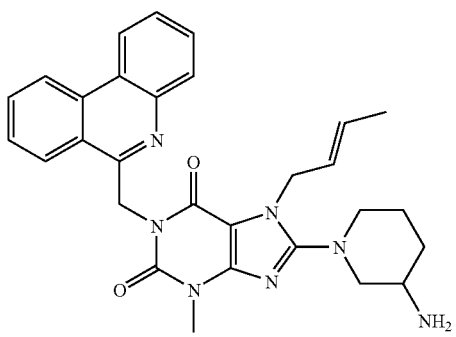 |
| (51) | 1-[(phenanthridin-6-yl)methyl]-3-methyl-7-((Z)-2-buten-1-yl)-8-(3-amino-piperidin-1-yl)-xanthine | 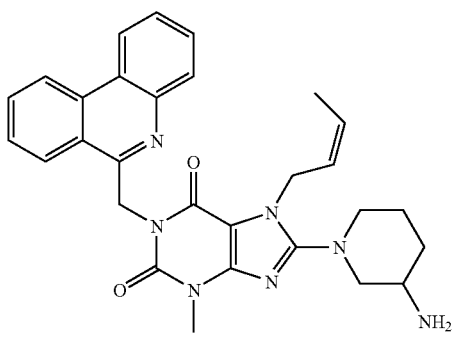 |

| No. | Name | Structural formula |
|---|---|---|
| (52) | 1-[(phenanthridin-6-yl)methyl]-3-methyl-7-[(1-cyclopenten-1-yl)methyl]-8-(3-amino-piperidin-1-yl)-xanthine | 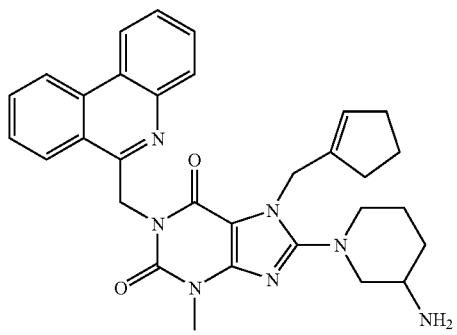 |
| (53) | 1-[(benzo[c][1,5]naphthyridin-6-yl)methyl]-3-methyl-7-(2-butyn-1-yl)-8-(3-amino-piperidin-1-yl)-xanthine | 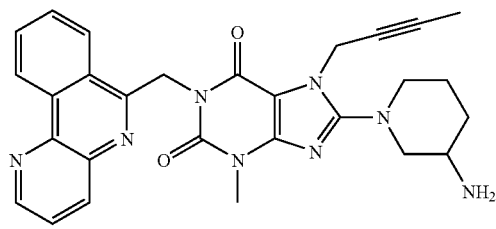 |
| (54) | 1-[(5H-dibenzo[d,f][1,3]diazepin-6-yl)methyl]-3-methyl-7-(2-butyn-1-yl)-8-(3-amino-piperidin-1-yl)-xanthine | 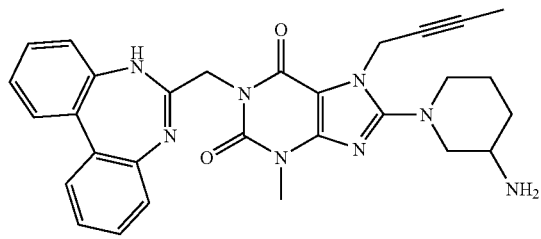 |
| (55) | 1-[(5H-benzo[e]pyrrolo[1,2-a][1,4]diazepin-11-yl)methyl]-3-methyl-7-(2-butyn-1-yl)-8-(3-amino-piperidin-1-yl)-xanthine | 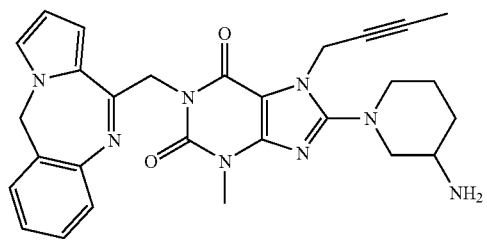 |
| (56) | 1-[(thieno[3,2-b][1,4]benzoxazepin-9-yl)methyl]-3-methyl-7-(2-butyn-1-yl)-8-(3-amino-piperidin-1-yl)-xanthine | 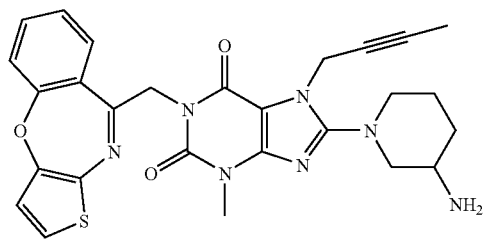 |

| No. | Name | Structural formula |
|---|---|---|
| (57) | 1-[(3,4-dihydro-quinazolin-2-yl)methyl]-3-phenyl-7-(2-butyn-1-yl)-8-(3-amino-piperidin-1-yl)-xanthine | 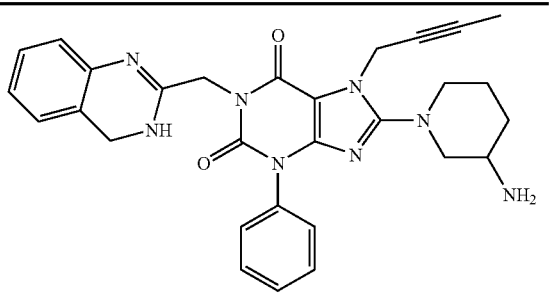 |
| (58) | 1-[(3,4-dihydro-isoquinolin-1-yl)methyl]-3-phenyl-7-(2-butyn-1-yl)-8-(3-amino-piperidin-1-yl)-xanthine | 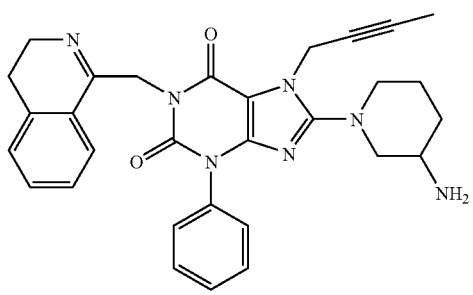 |
| (59) | 1-[(2,3-dihydro-benzo[f][1,4]oxazepin-5-yl)methyl]-3-phenyl-7-(2-butyn-1-yl)-8-(3-amino-piperidin-1-yl)-xanthine | 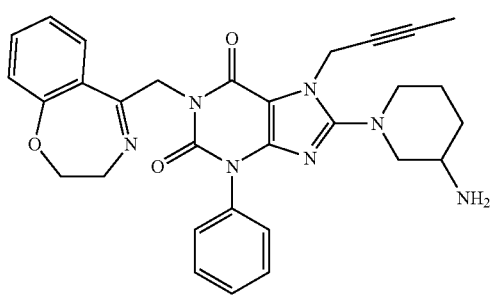 |
| (60) | 1-[(2-oxo-2,3-dihydro-1H-benzo[e][1,4]diazepin-5-yl)methyl]-3-phenyl-7-(2-butyn-1-yl)-8-(3-amino-piperidin-1-yl)-xanthine | 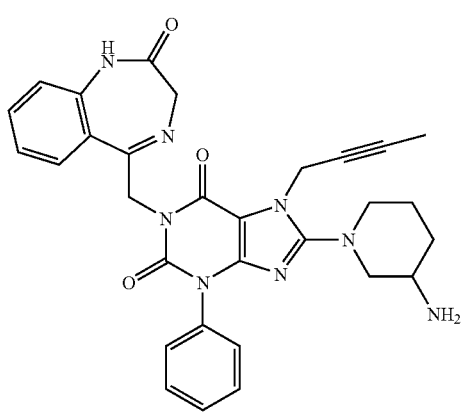 |

EXAMPLE 4

Coated tablets containing 75 mg of active substance

| 1 tablet core contains: | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg
die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE 5

Tablets Containing 100 mg of Active Substance

| Composition: | |
|---|---|
| 1 tablet contains: | |
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg
Diameter: 10 mm, biplanar, facetted on both sides and notched on one side.

EXAMPLE 6

Tablets Containing 150 ma of Active Substance

| Composition: | |
|---|---|
| 1 tablet contains: | |
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg
die: 10 mm, flat

EXAMPLE 7

Hard Gelatine Capsules Containing 150 ma of Active Substance

| 1 capsule contains: | | |
|---|---|---|
| active substance | | 150.0 mg |
| corn starch (dried) | approx. | 80.0 mg |
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg
Capsule shell: size 1 hard gelatine capsule.

EXAMPLE 8

Suppositories Containing 150 mg of Active Substance

| 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE 9

Suspension Containing 50 mg of Active Substance

| 100 ml of suspension contain: | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water ad | 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air. 5 ml of suspension contain 50 mg of active substance.

EXAMPLE 10

Ampoules Containing 10 mg Active Substance

| Composition: | |
|---|---|
| active substance | 10.0 mg |
| 0.01 N hydrochloric acid q.s. | |
| double-distilled water ad | 2.0 ml |

Preparation:

The active substance is dissolved in the necessary amount of 0.01 N HCl, made isotonic with common salt, filtered sterile and transferred into 2 ml ampoules.

EXAMPLE 11

Ampoules Containing 50 mg of Active Substance

| Composition: | |
|---|---|
| active substance | 50.0 mg |
| 0.01 N hydrochloric acid q.s. | |
| double-distilled water ad | 10.0 ml |

Preparation:

The active substance is dissolved in the necessary amount of 0.01 N HCl, made isotonic with common salt, filtered sterile and transferred into 10 ml ampoules.

What is claimed is:

1. A Compound of formula (I):

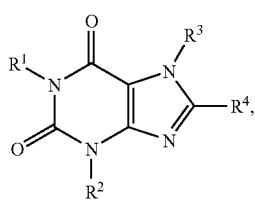

(I)

wherein

R$^1$ denotes a C$_{1-3}$-alkyl group substituted by a group R$_a$, wherein

R$_a$ denotes a 1,4-dihydro-quinazolinyl or 3,4-dihydro-quinazolinyl group wherein in each case in the benzo moiety one to three methyne groups may be replaced by nitrogen atoms, a 3,4-dihydro-isoquinolinyl, 1H-benzo[d][1,2]oxazinyl, 4H-benzo[e][1,3]oxazinyl, 4H-benzo[d][1,3]oxazinyl or 2H-benzo[1,4]oxazinyl group, wherein in each case
in the benzo moiety one to three methyne groups may be replaced by nitrogen atoms and in the heterocyclyl moiety a methylene group may be replaced by a carbonyl group, a 4H-benzo[e][1,3]thiazinyl, 4H-benzo[d][1,3]thiazinyl or 2H-benzo[1,4]thiazinyl group, wherein in each case
in the benzo moiety one to three methyne groups may be replaced by nitrogen atoms and in the heterocyclyl moiety a methylene group may be replaced by a carbonyl group and a sulphur atom may be replaced by a sulphinyl or sulphonyl group, a 2-oxo-2H-benzo[e][1,3]oxazinyl or 2,2-dioxo-1H-benzo[c][1,2]thiazinyl group, wherein in each case in the benzo moiety
one to three methyne groups may be replaced by nitrogen atoms, a 2,3-dihydro-1H-benzo[e][1,4]diazepinyl, 4,5-dihydro-3H-benzo[b]-[1,4]diazepinyl or 5-oxo-4,5-dihydro-3H-benzo[e][1,4]diazepinyl group, wherein in each case
in the benzo moiety one to three methyne groups may be replaced by nitrogen atoms and in the heterocyclyl moiety a methylene group may be replaced by a carbonyl group, a 2,3-dihydro-benzo[f][1,4]oxazepinyl or 2,3-dihydro-benzo[b][1,4]oxazepinyl group wherein in each case
in the benzo moiety one to three methyne groups may be replaced by nitrogen atoms and in the heterocyclyl moiety a methylene group may be replaced by a carbonyl group, a 2,3-dihydro-benzo[f][1,4]thiazepinyl or 2,3-dihydro-benzo[b][1,4]thiazepinyl group, wherein in each case
in the benzo moiety one to three methyne groups may be replaced by nitrogen atoms and in the heterocyclyl moiety a methylene group may be replaced by a carbonyl group and a sulphur atom may be replaced by a sulphinyl or sulphonyl group, a 5-oxo-4,5-dihydro-benzo[f][1,3,4]oxadiazepinyl group wherein in the benzo moiety
one to three methyne groups may be replaced by nitrogen atoms, an 11H-dibenzo[b,e]azepinyl or 5H-dibenzo[a,d]cycloheptenyl group, wherein in each case
in the benzo moiety one to three methyne groups may be replaced by nitrogen atoms and the methylene group in the heterocyclyl moiety may be replaced by an oxygen or sulphur atom, a carbonyl, sulphinyl, sulphonyl or an imino group substituted by R$_x$, where R$_x$ denotes a hydrogen atom or a C$_{1-4}$-alkyl, C$_{2-4}$-alkenyl, C$_{2-4}$-alkynyl, C$_{3-6}$-cycloalkyl, C$_{3-6}$-cycloalkyl-C$_{1-3}$-alkyl, aryl, aryl-C$_{1-3}$-alkyl, hydroxy-C$_{2-4}$-alkyl, C$_{1-3}$-alkyloxy-C$_{2-4}$-alkyl, C$_{3-6}$-cycloalkyloxy-C$_{2-4}$-alkyl, amino-C$_{2-4}$-alkyl, C$_{1-3}$-alkylamino-C$_{2-4}$-alkyl, di-(C$_{1-3}$-alkyl)-amino-C$_{2-4}$-alkyl, C$_{1-3}$-alkyl-carbonyl, C$_{1-3}$-alkyloxy-carbonyl, C$_{1-3}$-alkyloxy-carbonyl-C$_{1-3}$-alkyl, aryl-carbonyl, C$_{1-3}$-alkyl-sulphonyl or aryl-sulphonyl group, a 1,2,3,4-tetrahydro-phenanthridinyl, benzo[f]quinoxalinyl, 5H-dibenzo[d,f][1,3]diazepinyl, 5H-benzo[e]pyrrolo[1,2-a][1,4]diazepinyl, thieno[3,2-b][1,4]

benzoxazepinyl or a 3-oxo-2,3-dihydro-isoindol-1-ylidene group, wherein in each case
in the benzo moiety one to three methyne groups may be replaced by nitrogen atoms,
a benzo[1,2,5]oxadiazolyl, dibenzofuranyl, Indolizinyl, 1H-perimidinyl, group,
a pyrazolo[1,5-c]quinazolinyl group or an imidazo[2,1-a]isoquinolinyl or imidazo[1,2-a]isoquinolinyl group wherein the above-mentioned groups $R_a$ may be substituted by the groups $R^{10}$ to $R^{13}$ and may additionally be substituted by a $C_{1-3}$-alkyl group and
$R^{10}$ denotes a hydrogen atom,
a fluorine, chlorine, bromine or iodine atom,
a $C_{1-4}$-alkyl, hydroxy, or $C_{1-4}$-alkyloxy group,
a nitro, amino, $C_{1-3}$-alkylamino, di-($C_{1-3}$-alkyl)amino, cyano-$C_{1-3}$-alkylamino, [N-(cyano-$C_{1-3}$-alkyl)-N-$C_{1-3}$-alkyl-amino], $C_{1-3}$-alkyloxy-carbonyl-$C_{1-3}$-alkylamino, pyrrolidin-1-yl, piperidin-1-yl, morpholin-4-yl, piperazin-1-yl, or 4-($C_{1-3}$-alkyl)-piperazin-1-yl group,
a $C_{1-3}$-alkyl-carbonylamino, arylcarbonylamino, aryl-$C_{1-3}$-alkyl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino or 4-($C_{1-3}$-alkyl)-piperazin-1-yl-carbonylamino, $C_{1-3}$-alkyl-sulphonylamino, bis-($C_{1-3}$-alkylsulphonyl)-amino, aminosulphonylamino, $C_{1-3}$-alkylamino-sulphonylamino, di-($C_{1-3}$-alkyl)amino-sulphonylamino, pyrrolidin-1-yl-sulphonylamino, piperidin-1-yl-sulphonylamino, morpholin-4-yl-sulphonylamino, piperazin-1-yl-sulphonylamino or 4-($C_{1-3}$-alkyl)-piperazin-1-yl-sulphonylamino, ($C_{1-3}$-alkylamino)thiocarbonylamino, ($C_{1-3}$-alkyloxy-carbonylamino)-carbonylamino, arylsulphonylamino or aryl-$C_{1-3}$-alkyl-sulphonylamino group,
an N-($C_{1-3}$-alkyl)-$C_{1-3}$-alkyl-carbonylamino, N-($C_{1-3}$-alkyl)-arylcarbonylamino, N-($C_{1-3}$-alkyl)-aryl-$C_{1-3}$-alkyl-carbonylamino, N-($C_{1-3}$-alkyl)-$C_{1-3}$-alkyloxy-carbonylamino, N-(aminocarbonyl)-$C_{1-3}$-alkylamino, N-($C_{1-3}$-alkyl-aminocarbonyl)-$C_{1-3}$-alkylamino, N-[di-($C_{1-3}$-alkyl)aminocarbonyl]-$C_{1-3}$-alkylamino, N-($C_{1-3}$-alkyl)-$C_{1-3}$-alkyl-sulphonylamino, N-($C_{1-3}$-alkyl)-arylsulphonylamino or N-($C_{1-3}$-alkyl)-aryl-$C_{1-3}$-alkyl-sulphonylamino group,
a 2-oxo-imidazolidin-1-yl, 2,4-dioxo-imidazolidin-1-yl, 2,5-dioxo-imidazolidin-1-yl or 2-oxo-hexahydropyrimidin-1-yl group wherein the nitrogen atom in the 3 position may be substituted in each case by a methyl or ethyl group,
a cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl or 4-($C_{1-3}$-alkyl)-piperazin-1-yl-carbonyl group,
a $C_{1-3}$-alkyl-carbonyl or an arylcarbonyl group,
a carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, piperazin-1-yl-carbonyl-$C_{1-3}$-alkyl or 4-($C_{1-3}$-alkyl)-piperazin-1-yl-carbonyl-$C_{1-3}$-alkyl group,
a carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyloxy, piperidin-1-yl-carbonyl-$C_{1-3}$-alkyloxy, morpholin-4-yl-carbonyl-$C_{1-3}$-alkyl-oxy, piperazin-1-yl-carbonyl-$C_{1-3}$-alkyloxy or 4-($C_{1-3}$-alkyl)-piperazin-1-yl-carbonyl-$C_{1-3}$-alkyloxy group,
a hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, piperidin-1-yl-$C_{1-3}$-alkyl, morpholin-4-yl-$C_{1-3}$-alkyl, piperazin-1-yl-$C_{1-3}$-alkyl, 4-($C_{1-3}$-alkyl)-piperazin-1-yl-$C_{1-3}$-alkyl group,
a hydroxy-$C_{1-3}$-alkyloxy, $C_{1-3}$-alkyloxy-$C_{1-3}$-alkyloxy, $C_{1-3}$-alkylsulphanyl-$C_{1-3}$-alkyloxy, $C_{1-3}$-alkylsulphinyl-$C_{1-3}$-alkyloxy, $C_{1-3}$-alkylsulphonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, piperidin-1-yl-$C_{1-3}$-alkyloxy, morpholin-4-yl-$C_{1-3}$-alkyloxy, piperazin-1-yl-$C_{1-3}$-alkyloxy, 4-($C_{1-3}$-alkyl)-piperazin-1-yl-$C_{1-3}$-alkyloxy group,
a mercapto, $C_{1-3}$-alkylsulphanyl, $C_{1-3}$-alkylsulphinyl, $C_{1-3}$-alkylsulphonyl, $C_{1-3}$-alkylsulphonyloxy, arylsulphonyloxy, trifluoromethylsulphanyl, trifluoromethylsulphinyl or trifluoromethylsulphonyl group,
a sulpho, aminosulphonyl, $C_{1-3}$-alkyl-aminosulphonyl, di-($C_{1-3}$-alkyl)-aminosulphonyl, pyrrolidin-1-yl-sulphonyl, piperidin-1-yl-sulphonyl, morpholin-4-yl-sulphonyl, piperazin-1-yl-sulphonyl or 4-($C_{1-3}$-alkyl)-piperazin-1-yl-sulphonyl group,
a methyl or methoxy group substituted by 1 to 3 fluorine atoms,
an ethyl or ethoxy group substituted by 1 to 5 fluorine atoms,
a $C_{2-4}$-alkenyl or $C_{2-4}$-alkynyl group,
a $C_{3-4}$-alkenyloxy or $C_{3-4}$-alkynyloxy group,
a $C_{3-6}$-cycloalkyl or $C_{3-6}$-cycloalkyloxy group,
a $C_{3-6}$-cycloalkyl-$C_{1-3}$-alkyl or $C_{3-6}$-cycloalkyl-$C_{1-3}$-alkyloxy group or
an aryl, aryloxy, aryl-$C_{1-3}$-alkyl or aryl-$C_{1-3}$-alkyloxy group,
$R^{11}$ and $R^{12}$, which may be identical or different, in each case denote a hydrogen atom, a fluorine, chlorine, bromine or iodine atom, a $C_{1-3}$-alkyl, trifluoromethyl, hydroxy or $C_{1-3}$-alkyloxy group or a cyano group, or
$R^{11}$ together with $R^2$, if they are bound to adjacent carbon atoms, also denote a methylenedioxy, difluoromethylenedioxy, ethylenedioxy or a straight-chain $C_{3-5}$-alkylene group and
$R^{13}$ denotes a hydrogen atom, a fluorine, chlorine or bromine atom, a trifluoromethyl, $C_{1-3}$-alkyl or $C_{1-3}$-alkyloxy group, $R^2$ denotes a hydrogen atom,
a $C_{1-6}$alkyl group,
a $C_{2-4}$-alkenyl group,
a $C_{3-4}$-alkynyl group,
a $C_{3-6}$-cycloalkyl group,
a $C_{3-6}$-cycloalkyl-$C_{1-3}$-alkyl group,
a tetrahydrofuran-3-yl, tetrahydropyran-3-yl, tetrahydropyran-4-yl, tetrahydrofuranylmethyl or tetrahydropyranylmethyl group,
an aryl group,
an aryl-$C_{1-4}$-alkyl group,
an aryl-$C_{2-3}$-alkenyl group,
an arylcarbonyl-$C_{1-2}$-alkyl group,
a heteroaryl-$C_{1-3}$-alkyl group,
a furanylcarbonylmethyl, thienylcarbonylmethyl, thiazolylcarbonylmethyl or pyridylcarbonylmethyl group,
a $C_{1-4}$-alkyl-carbonyl-$C_{1-2}$-alkyl group,
a $C_{3-6}$-cycloalkyl-carbonyl-$C_{1-2}$-alkyl group,
an aryl-A-$C_{1-3}$-alkyl group, wherein A denotes an oxygen or sulphur atom, —NH—, N($C_{1-3}$-alkyl), sulphinyl or sulphonyl group,
a $C_{1-4}$-alkyl group substituted by a group $R_b$, wherein
  $R_b$ denotes a cyano, carboxy, $C_{1-3}$-alkyloxy-carbonyl, aminocarbonyl, $C_{1-3}$-alkylamino-carbonyl, di-($C_{1-3}$-alkyl)-amino-carbonyl, pyrrolidin-1-ylcarbonyl, piperidin-1-ylcarbonyl, morpholin-4-ylcarbonyl, piperazin-1-ylcarbonyl, 4-methylpiperazin-1-ylcarbonyl or 4-ethylpiperazin-1-ylcarbonyl group,
or a $C_{2-4}$-alkyl group substituted by a group $R_c$, wherein
  $R_c$ denotes a hydroxy, $C_{1-3}$-alkyloxy, amino, $C_{1-3}$-alkylamino, di-($C_{1-3}$-alkyl)-amino, pyrrolidin-1-yl, piperidin-1-yl, morpholin-4-yl, piperazin-1-yl, 4-methyl-piperazin-1-yl or 4-ethyl-piperazin-1-yl group and is isolated from the cyclic nitrogen atom in the 3 position of the xanthine structure by at least two carbon atoms,
$R^3$ denotes a $C_{3-8}$-alkyl group,
a $C_{1-3}$-alkyl group substituted by a group $R_d$, wherein
  $R_d$ denotes a $C_{3-7}$-cycloalkyl group optionally substituted by one or two $C_{1-3}$-alkyl groups,
  a $C_{5-7}$-cycloalkenyl group optionally substituted by one or two $C_{1-3}$-alkyl groups,
  an aryl group or
  a furanyl, thienyl, oxazolyl, isoxazolyl, thiazolyl, isothiazolyl-, pyridyl, pyridazinyl, pyrimidyl or pyrazinyl group, wherein the above-mentioned heterocyclic groups may be substituted in each case by one or two $C_{1-3}$-alkyl groups or by a fluorine, chlorine, bromine or iodine atom or by a trifluoromethyl, cyano or $C_{1-3}$-alkyloxy group,
a $C_{3-8}$-alkenyl group,
a $C_{3-6}$-alkenyl group substituted by a fluorine, chlorine or bromine atom or a trifluoromethyl group,
a $C_{3-8}$-alkynyl group,
an aryl group or
an aryl-$C_{2-4}$-alkenyl group, and
$R^4$ denotes an azetidin-1-yl or pyrrolidin-1-yl group which is substituted in the 3 position by an amino, $C_{1-3}$-alkylamino or a di-($C_{1-3}$-alkyl)amino group and may additionally be substituted by one or two $C_{1-3}$-alkyl groups,
a piperidin-1-yl or hexahydroazepin-1-yl group which is substituted in the 3 position or in the 4 position by an amino, $C_{1-3}$-alkylamino or a di-($C_{1-3}$-alkyl)amino group and may additionally be substituted by one or two $C_{1-3}$-alkyl groups,
a 3-amino-piperidin-1-yl group wherein the piperidin-1-yl-moiety is additionally substituted by an aminocarbonyl, $C_{1-2}$-alkyl-aminocarbonyl, di-($C_{1-2}$-alkyl)aminocarbonyl, pyrrolidin-1-yl-carbonyl, (2-cyano-pyrrolidin-1-yl)-carbonyl, thiazolidin-3-yl-carbonyl, (4-cyano-thiazolidin-3-yl)carbonyl, piperidin-1-ylcarbonyl or morpholin-4-ylcarbonyl group,
a 3-amino-piperidin-1-yl group wherein the piperidin-1-yl-moiety is additionally substituted in the 4 position or in the 5 position by a hydroxy or methoxy group,
a 3-amino-piperidin-1-yl group wherein the methylene group in 2 position or in 6 position is replaced by a carbonyl group,
a piperidin-1-yl or hexahydroazepin-1-yl group substituted in the 3 position by an amino, $C_{1-3}$-alkylamino or di-($C_{1-3}$-alkyl)-amino group, wherein in each case two hydrogen atoms on the carbon skeleton of the piperidin-1-yl or hexahydroazepin-1-yl group are replaced by a straight-chain alkylene bridge, wherein this bridge contains 2 to 5 carbon atoms, if the two hydrogen atoms are located on the same carbon atom, or contains 1 to 4 carbon atoms if the hydrogen atoms are located on adjacent carbon atoms, or contains 1 to 4 carbon atoms, if the hydrogen atoms are located on carbon atoms which by are separated by one atom, or contains 1 to 3 carbon atoms if the two hydrogen atoms are located on carbon atoms which are separated by two atoms,
an azetidin-1-yl, pyrrolidin-1-yl, piperidin-1-yl or hexahydroazepin-1-yl group which is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group,
a piperazin-1-yl or [1,4]diazepan-1-yl group optionally substituted on the carbon skeleton by one or two $C_{1-3}$-alkyl groups,
a 3-imino-piperazin-1-yl, 3-imino-[1,4]diazepan-1-yl or 5-imino-[1,4]diazepan-1-yl group optionally substituted on the carbon skeleton by one or two $C_{1-3}$-alkyl groups,
a [1,4]diazepan-1-yl group optionally substituted by one or two $C_{1-3}$-alkyl groups, which is substituted by an amino group in the 6 position,
a $C_{3-7}$-cycloalkyl group which is substituted by an amino, $C_{1-3}$-alkylamino or di-($C_{1-3}$-alkyl)-amino group,
a $C_{3-7}$-cycloalkyl group which is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group,
a $C_{3-7}$-cycloalkyl-$C_{1-2}$-alkyl group wherein the cycloalkyl moiety is substituted by an amino, $C_{1-3}$-alkylamino or di-($C_{1-3}$-alkyl)-amino group,
a $C_{3-7}$-cycloalkyl-$C_{1-2}$-alkyl group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group,
a $C_{3-7}$-cycloalkylamino group wherein the cycloalkyl moiety is substituted by an amino, $C_{1-3}$-alkylamino or di-($C_{1-3}$-alkyl)-amino group, wherein the two nitrogen atoms on the cycloalkyl moiety are separated from one another by at least two carbon atoms,
an N-($C_{3-7}$-cycloalkyl)-N-($C_{1-3}$-alkyl)-amino group wherein the cycloalkyl moiety is substituted by an amino, $C_{1-3}$-alkylamino or di-($C_{1-3}$-alkyl)-amino group, wherein the two nitrogen atoms on the cycloalkyl moiety are separated from one another by at least two carbon atoms,
a $C_{3-7}$-cycloalkylamino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, an N-($C_{3-7}$-cycloalkyl)-N-($C_{1-3}$-alkyl)-amino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, a $C_{3-7}$-cycloalkyl-$C_{1-2}$-alkyl-amino group wherein the cycloalkyl moiety is substituted by an amino, $C_{1-3}$-alkylamino or di-($C_{1-3}$-alkyl)-amino group, an N-($C_{3-7}$-cycloalkyl-$C_{1-2}$-alkyl)-N-($C_{1-2}$-alkyl)-amino group wherein the cycloalkyl moiety is substituted by an amino, $C_{1-3}$-alkylamino or di-($C_{1-3}$-alkyl)-amino group, a $C_{3-7}$-cycloalkyl-$C_{1-2}$-alkyl-amino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, an N-($C_{3-7}$-cycloalkyl-$C_{1-2}$-alkyl)-N-($C_{1-2}$-alkyl)-amino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, an $R^{19}$—$C_{2-4}$-alkylamino group wherein $R^{19}$ is separated from the nitrogen atom of the $C_{2-4}$-alkylamino moiety by at least two carbon atoms and $R^{19}$ denotes an amino, $C_{1-3}$-alkylamino or di-($C_{1-3}$-alkyl)-amino group, an $R^{19}$—$C_{2-4}$-alkylamino group wherein the nitrogen atom of the $C_{2-4}$-alkylamino moiety is substituted by a $C_{1-3}$-alkyl group and $R^{19}$ is separated from the nitrogen atom of the $C_{2-4}$-alkylamino moiety by at least two carbon atoms, wherein $R^{19}$ is as hereinbefore defined, an amino group substituted by the group $R^{20}$ wherein $R^{20}$ denotes an azetidin-3-yl, azetidin-2-ylmethyl, azetidin-3-ylmethyl, pyrrolidin-3-yl, pyrrolidin-2-ylmethyl, pyrrolidin-3-ylmethyl, piperidin-3-yl, piperidin-4-yl, piperidin-2-ylmethyl, piperidin-3-ylmethyl or piperidin-4-ylmethyl group, wherein the groups mentioned for $R^{20}$ may each be substituted by one or two $C_{1-3}$-alkyl groups, an amino group substituted by the group $R^{20}$ and a $C_{1-3}$-alkyl group wherein $R^{20}$ is as hereinbefore defined, wherein the groups mentioned for $R^{20}$ may each be substituted by one or two $C_{1-3}$-alkyl groups, a $R^{19}$—$C_{3-4}$-alkyl group wherein the $C_{3-4}$-alkyl moiety is straight-chain and may additionally be substituted by one or two $C_{1-3}$-alkyl groups, wherein $R^{19}$ is as hereinbefore defined, a 3-amino-2-oxo-piperidin-5-yl or 3-amino-2-oxo-1-methyl-piperidin-5-yl group, a pyrrolidin-3-yl, piperidin-3-yl, piperidin-4-yl, hexahydroazepin-3-yl or hexahydroazepin-4-yl group which is substituted in the 1 position by an amino, $C_{1-3}$-alkylamino or di-($C_{1-3}$-alkyl)amino group, or an azetidin-2-yl-$C_{1-2}$-alkyl, azetidin-3-yl-$C_{1-2}$-alkyl, pyrrolidin-2-yl-$C_{1-2}$-alkyl, pyrrolidin-3-yl, pyrrolidin-3-yl-$C_{1-2}$-alkyl, piperidin-2-yl-$C_{1-2}$-alkyl, piperidin-3-yl, piperidin-3-yl-$C_{1-2}$-alkyl, piperidin-4-yl or piperidin-4-yl-$C_{1-2}$-alkyl group, wherein the above-mentioned groups may each be substituted by one or two $C_{1-3}$-alkyl groups, wherein by the aryl groups mentioned in the definition of the above groups are meant phenyl or naphthyl groups, which may be mono- or disubstituted by $R_h$ independently of one another, where the substituents are identical or different and $R_h$ denotes a fluorine, chlorine, bromine or iodine atom, a trifluoromethyl, cyano, nitro, amino, aminocarbonyl, aminosulphonyl, methylsulphonyl, acetylamino, methylsulphonylamino, $C_{1-3}$-alkyl, cyclopropyl, ethenyl, ethynyl, hydroxy, $C_{1-3}$-alkyloxy, difluoromethoxy or trifluoromethoxy group, by the heteroaryl groups mentioned in the definitions of the above mentioned groups are meant a pyrrolyl, furanyl, thienyl, pyridyl, indolyl, benzofuranyl, benzothiophenyl, quinolinyl or isoquinolinyl group, or a pyrrolyl, furanyl, thienyl or pyridyl group wherein one or two methyne groups are replaced by nitrogen atoms, or an indolyl, benzofuranyl, benzothiophenyl, quinolinyl or isoquinolinyl group wherein one to three methyne groups are replaced by nitrogen atoms, and the above-mentioned heteroaryl groups may be mono- or disubstituted by $R_h$, wherein the substituents may be identical or different and $R_h$ is as hereinbefore defined, and, unless otherwise specified, the above-mentioned alkyl, alkenyl and alkynyl groups may be straight-chain or branched, or the tautomers, enantiomers, diastereomers, the mixtures thereof, the prodrugs thereof and the salts thereof.

2. The Compound according to claim 1, wherein $R^1$ denotes a methyl group substituted by a group $R_a$, where $R_a$ denotes a 1,4-dihydro-quinazolinyl or 3,4-dihydro-quinazolinyl group, a 3,4-dihydro-isoquinolinyl group, a 1H-benzo[d][1,2]oxazinyl or 1-oxo-1H-benzo[d][1,2] oxazinyl group, a 4H-benzo[e][1,3]oxazinyl or 4-oxo-4H-benzo[e][1,3] oxazinyl group, a 4H-benzo[d][1,3]oxazinyl or 4-oxo-4H-benzo[d][1,3] oxazinyl group, 2H-benzo[1,4]oxazinyl or 2-oxo-2H-benzo[1,4]oxazinyl group, a 4H-benzo[e][1,3]thiazinyl or 4-oxo-4H-benzo[e][1,3] thiazinyl group, a 4H-benzo[d][1,3]thiazinyl or 2H-benzo[1,4]thiazinyl group, a 2-oxo-2H-benzo[e][1,3]oxazinyl or 2,2-dioxo-1H-benzo[c][1,2]thiazinyl group, a 2,3-dihydro-1H-benzo[e][1,4]diazepinyl or 2-oxo-2,3-dihydro-1H-benzo[e][1,4]diazepinyl group, a 4,5-dihydro-3H-benzo[b][1,4]diazepinyl or 4-oxo-4,5-dihydro-3H-benzo[b][1,4]diazepinyl group, a 5-oxo-4,5-dihydro-3H-benzo[e][1,4]diazepinyl group, a 2,3-dihydro-benzo[f][1,4]oxazepinyl or 2,3-dihydro-benzo[b][1,4]oxazepinyl group, a 2,3-dihydro-benzo[f][1,4]thiazepinyl-2,3-dihydro-benzo[b][1,4]thiazepinyl group, a 5-oxo-4,5-dihydro-benzo[f][1,3,4]oxadiazepinyl group, an 11H-dibenzo[b,e]azepinyl or 11-oxo-11H-dibenzo[b,e]azepinyl group, an 11H-benzo[e]pyrido[3,2-b]azepinyl group, a 5H-dibenzo[b,e][1,4]diazepinyl or dibenzo[b,f][1,4] oxazepinyl group, a dibenzo[b,f][1,4]thiazepinyl, 5-oxo-dibenzo[b,f][1,4] thiazepinyl or 5,5-dioxo-dibenzo[b,f][1,4]thiazepinyl group, 5H-dibenzo[a,d]cycloheptenyl or 5H-dibenzo[b,f] azepinyl group, benzo[c][1,5]naphthyridinyl, benzo[h][1,6]naphthyridinyl, benzo[c][1,8]naphthyridinyl or 1,2,3,4-tetrahydro-phenanthridinyl group, a benzo[f]quinoxalinyl group, a 5H-dibenzo[d,f][1,3]diazepinyl, 5H-benzo[e]pyrrolo[1,2-a][1,4]diazepinyl or thieno[3,2-b][1,4]benzoxazepinyl group, a 3-oxo-2,3-dihydro-isoindol-1-ylidene group,
a benzo[1,2,5]oxadiazolyl group,
a dibenzofuranyl group,
an indolizinyl group,
a 1H-perimidinyl group,
a pyrazolo[1,5-c]quinazolinyl group or
an imidazo[2,1-a]isoquinolinyl or imidazo[1,2-a]isoquinolinyl group
wherein the benzo groups of the above-mentioned groups $R_a$ are substituted by the groups $R^{10}$ to $R^{12}$ and the alkylene units of the above-mentioned groups $R_a$ may be substituted by one or two $C_{1-3}$-alkyl or $C_{1-3}$-alkyloxy-carbonyl groups, wherein the groups may be identical or different, or by a trifluoromethyl group, and the imino groups of the above-mentioned groups $R_a$ may be substituted by a $C_{1-3}$-alkyl group and
$R^{10}$ denotes a hydrogen atom,
a fluorine, chlorine, bromine or iodine atom,
a $C_{1-3}$-alkyl or cyclopropyl group,
a hydroxy, $C_{1-3}$-alkyloxy or cyclopropyloxy group,
a nitro, amino, $C_{1-3}$-alkylamino or di-($C_{1-3}$-alkyl)amino group,
a $C_{1-3}$-alkyl-carbonylamino or $C_{1-3}$-alkyl-sulphonylamino group,
a cyano, carboxy, $C_{1-3}$-alkyloxy-carbonyl, aminocarbonyl, $C_{1-3}$-alkyl-aminocarbonyl or di-($C_{1-3}$-alkyl)-aminocarbonyl group,
a mercapto, $C_{1-3}$-alkylsulphanyl, $C_{1-3}$-alkylsulphinyl or aminosulphonyl group or
a difluoromethyl, trifluoromethyl, difluoromethoxy or trifluoromethoxy group and
$R^{11}$ and $R^{12}$, which may be identical or different, in each case represent a hydrogen atom, a fluorine, chlorine or bromine atom, a methyl, trifluoromethyl or methoxy group,
$R^2$ denotes a hydrogen atom,
a $C_{1-3}$-alkyl group,
a $C_{3-6}$-cycloalkyl group or
a phenyl group optionally mono- or disubstituted by a fluorine, chlorine, bromine or iodine atom, a trifluoromethyl, cyano, nitro, amino, aminocarbonyl, aminosulphonyl, methylsulphonyl, acetylamino, methylsulphonylamino, $C_{1-3}$-alkyl, cyclopropyl, ethenyl, ethynyl, hydroxy, $C_{1-3}$-alkyloxy, difluoromethoxy or trifluoromethoxy group, wherein the substituents may be identical or different,
$R^3$ denotes a 2-buten-1-yl or 3-methyl-2-buten-1-yl group,
a 2-butyn-1-yl group or
a 1-cyclopenten-1-ylmethyl group and
$R^4$ denotes a (3-amino-piperidin-1-yl) group,
wherein, unless otherwise stated, the above-mentioned alkyl groups may be straight-chain or branched.

3. The Compound according to claim 2, wherein
$R^1$ denotes a methyl group substituted by a group $R_a$, where $R_a$ denotes a 1,4-dihydro-quinazolin-2-yl or 3,4-dihydro-quinazolin-2-yl group,
a 3,4-dihydro-isoquinolin-1-yl group,
a 1H-benzo[d][1,2]oxazin-4-yl or 1-oxo-1H-benzo[d][1,2]oxazin-4-yl group,
a 4H-benzo[e][1,3]oxazin-2-yl or 4-oxo-4H-benzo[e][1,3]oxazin-2-yl group,
a 4H-benzo[d][1,3]oxazin-2-yl or 4-oxo-4H-benzo[d][1,3]oxazin-2-yl group,
2H-benzo[1,4]oxazin-3-yl or 2-oxo-2H-benzo[1,4]oxazin-3-yl group,
a 4H-benzo[e][1,3]thiazin-2-yl or 4-oxo-4H-benzo[e][1,3]thiazin-2-yl group,
a 4H-benzo[d][1,3]thiazin-2-yl or 2H-benzo[1,4]thiazin-3-yl group,
a 2-oxo-2H-benzo[e][1,3]oxazin-4-yl or 2,2-dioxo-1H-benzo[c][1,2]thiazin-4-yl group,
a 2,3-dihydro-1H-benzo[e][1,4]diazepin-5-yl or 2-oxo-2,3-dihydro-1H-benzo[e][1,4]diazepin-5-yl group,
a 4,5-dihydro-3H-benzo[b][1,4]diazepin-2-yl or 4-oxo-4,5-dihydro-3H-benzo[b][1,4]diazepin-2-yl group,
a 5-oxo-4,5-dihydro-3H-benzo[e][1,4]diazepin-2-yl group,
a 2,3-dihydro-benzo[f][1,4]oxazepin-5-yl or 2,3-dihydro-benzo[b]-[1,4]oxazepin-4-yl group,
a 2,3-dihydro-benzo[f][1,4]thiazepin-5-yl or 2,3-dihydro-benzo[b]-[1,4]thiazepin-4-yl group,
a 5-oxo-4,5-dihydro-benzo[f][1,3,4]oxadiazepin-2-yl group,
an 11H-dibenzo[b,e]azepin-6-yl or 11-oxo-11H-dibenzo[b,e]azepin-6-yl group,
an 11H-benzo[e]pyrido[3,2-b]azepin-6-yl group
a 5H-dibenzo[b,e][1,4]diazepin-11-yl or dibenzo[b,f][1,4]oxazepin-11-yl group,
a dibenzo[b,f][1,4]thiazepin-11-yl, 5-oxo-dibenzo[b,f][1,4]thiazepin-11-yl or 5,5-dioxo-dibenzo[b,f][1,4]thiazepin-11-yl group,
a 5H-dibenzo[a,d]cyclohepten-10-yl or 5H-dibenzo[b,f]azepin-10-yl group,
a benzo[c][1,5]naphthyridin-6-yl, benzo[h][1,6]naphthyridin-5-yl, benzo[c][1,8]naphthyridin-6-yl or 1,2,3,4-tetrahydro-phenanthridin-6-yl group,
a benzo[f]quinoxalin-6-yl group,
a 5H-dibenzo[d,f][1,3]diazepin-6-yl, 5H-benzo[e]pyrrolo[1,2-a][1,4]diazepin-11-yl or thieno[3,2-b][1,4]benzoxazepinyl-9-yl group,
a 3-oxo-2,3-dihydro-isoindol-1-ylidene group,
a benzo[1,2,5]oxadiazol-5-yl group,
a dibenzofuran-2-yl group,
an indolizin-2-yl group,
a 1H-perimidin-2-yl group,
a pyrazolo[1,5-c]quinazolin-5-yl group or
an imidazo[2,1-a]isoquinolin-2-yl or imidazo[1,2-a]isoquinolin-2-yl group
wherein the benzo[groups of the above-mentioned groups $R_a$ are substituted by the groups $R^{10}$ to $R^{12}$ and the alkylene units of the above-mentioned groups $R_a$ may be substituted by one or two methyl- or methoxy-carbonyl groups, wherein the groups may be identical or different, or by a trifluoromethyl group and the imino groups of the above-mentioned groups $R_a$ may be substituted by a methyl group and
$R^{10}$ denotes a hydrogen atom,
a fluorine, chlorine, bromine or iodine atom,
a methyl or ethyl group,
a hydroxy, methoxy or ethoxy group or
a difluoromethyl, trifluoromethyl, difluoromethoxy or trifluoromethoxy group and
$R^{11}$ and $R^{12}$, which may be identical or different, each represent a hydrogen atom, a fluorine, chlorine or bromine atom, a methyl, trifluoromethyl or methoxy group,
$R^2$ denotes a hydrogen atom or
a methyl, ethyl, propyl, isopropyl, phenyl or cyclopropyl group,
$R^3$ denotes a 2-buten-1-yl or 3-methyl-2-buten-1-yl group,
a 2-butyn-1-yl group or
a 1-cyclopenten-1-ylmethyl group and
$R^4$ denotes a (3-amino-piperidin-1-yl) group.

4. The Compound according to claim 3, wherein $R^1$ denotes a 3-methoxycarbonyl-3-methyl-3,4-dihydro-isoquinolin-1-ylmethyl group,
a 1-methyl-2,2-dioxo-1H-benzo[c][1,2]thiazin-4-ylmethyl group,
a 2,3-dihydro-benzo[f][1,4]oxazepin-5-ylmethyl group,
a 2-oxo-2,3-dihydro-1H-benzo[e][1,4]diazepin-5-ylmethyl group,
1,2,3,4-tetrahydro-phenanthridin-6-ylmethyl group,
an 11H-dibenzo[b,e]azepin-6-ylmethyl group,
a dibenzo[b,f][1,4]oxazepin-11-ylmethyl group,
a 3-oxo-2,3-dihydro-isoindol-1-ylidenemethyl group,
a 3-trifluoromethyl-3,4-dihydro-isoquinolin-1-ylmethyl group,
a 3,4-dihydro-quinazolin-2-ylmethyl group,
a 5-methyl-5H-dibenzo[b,e][1,4]diazepin-11-ylmethyl group,
an 8-methyl-dibenzo[b,f][1,4]oxazepin-11-ylmethyl group,
a benzo[1,2,5]oxadiazol-5-ylmethyl group,
an 8-methyl-phenanthridin-6-ylmethyl group,
a 1-methyl-phenanthridin-6-ylmethyl group,
a 4-methyl-phenanthridin-6-ylmethyl group,
a benzo[h][1,6]naphthyridin-5-ylmethyl group,
a pyrazolo[1,5-c]quinazolin-5-yl group,
a benzo[c][1,8]naphthyridin-6-ylmethyl group,
a benzo[c][1,5]naphthyridin-6-ylmethyl group,
a 1H-perimidin-2-ylmethyl group,
a benzo[f]quinoxalin-6-ylmethyl group or
an imidazo[2,1-a]isoquinolin-2-ylmethyl or imidazo[1,2-a]isoquinolin-2-ylmethyl group, $R^2$ denotes a methyl or cyclopropyl group, $R^3$ denotes a 2-buten-1-yl, 3-methyl-2-buten-1-yl or 2-butyn-1-yl group and $R^4$ denotes a (3-amino-piperidin-1-yl) group, the tautomers, enantiomers, diastereomers, the mixtures thereof and the salts thereof.

5. A compound chosen from:

(1) 1-[(1-methyl-2,2-dioxo-1H-benzo[c][1,2]thiazin-4-yl)methyl]-3-methyl-7-(3-methyl-2-buten-1-yl)-8-(3-amino-piperidin-1-yl)-xanthine,
(2) 1-[(3-methoxycarbonyl-3-methyl-3,4-dihydro-isoquinolin-1-yl]methyl]-3-methyl-7-(2-butyn-1-yl)-8-(3-amino-piperidin-1-yl)-xanthine,
(3) 1-[(2-oxo-2,3-dihydro-1H-benzo[e][1,4]diazepin-5-yl)methyl]-3-methyl-7-((E)-2-buten-1-yl)-8-((R)-3-amino-piperidin-1-yl)-xanthine,
(5) 1-[(1,2,3,4-tetrahydro-phenanthridin-6-yl)methyl]-3-methyl-7-(2-butyn-1-yl)-8-(3-amino-piperidin-1-yl)-xanthine,
(6) 1-[(11H-dibenzo[b,e]azepin-6-yl)methyl]-3-methyl-7-(2-butyn-1-yl)-8-(3-amino-piperidin-1-yl)-xanthine,
(7) 1-[(dibenzo[b,f][1,4]oxazepin-11-yl)methyl]-3-methyl-7-(2-butyn-1-yl)-8-(3-amino-piperidin-1-yl)-xanthine,
(8) 1-[(3-trifluoromethyl-3,4-dihydro-isoquinolin-1-yl)methyl]-3-methyl-7-(2-butyn-1-yl)-8-(3-amino-piperidin-1-yl)-xanthine,
(9) 1-[(dibenzo[b,f][1,4]oxazepin-11-yl)methyl]-3-methyl-7-(2-butyn-1-yl)-8-((R)-3-amino-piperidin-1-yl)-xanthine,
(10) 1-[(3,4-dihydro-quinazolin-2-yl)methyl]-3-methyl-7-(2-butyn-1-yl)-8-(3-amino-piperidin-1-yl)-xanthine,
(11) 1-[(5-methyl-5H-dibenzo[b,e][1,4]diazepin-11-yl)methyl]-3-methyl-7-(2-butyn-1-yl)-8-(3-amino-piperidin-1-yl)-xanthine,
(12) 1-[(8-methyl-dibenzo[b,f][1,4]oxazepin-11-yl)methyl]-3-methyl-7-(2-butyn-1-yl)-8-(3-amino-piperidin-1-yl)-xanthine,
(13) 1-[(benzo[1,2,5]oxadiazol-5-yl)methyl]-3-methyl-7-(2-butyn-1-yl)-8-(3-amino-piperidin-1-yl)-xanthine,
(15) 1-[(8-methyl-phenanthridin-6-yl)methyl]-3-methyl-7-(2-butyn-1-yl)-8-(3-amino-piperidin-1-yl)-xanthine,
(18) 1-[(1-methyl-phenanthridin-6-yl)methyl]-3-methyl-7-(2-butyn-1-yl)-8-((R)-3-amino-piperidin-1-yl)-xanthine,
(19) 1-[(4-methyl-phenanthridin-6-yl)methyl]-3-methyl-7-(2-butyn-1-yl)-8-((R)-3-amino-piperidin-1-yl)-xanthine,
(20) 1-[(benzo[h][1,6]naphthyridin-5-yl)methyl]-3-methyl-7-(2-butyn-1-yl)-8-(3-amino-piperidin-1-yl)-xanthine,
(21) 1-[(pyrazolo[1,5-c]quinazolin-5-yl)methyl]-3-methyl-7-(2-butyn-1-yl)-8-(3-amino-piperidin-1-yl)-xanthine,
(22) 1-[(benzo[c][1,8]naphthyridin-6-yl)methyl]-3-methyl-7-(2-butyn-1-yl)-8-(3-amino-piperidin-1-yl)-xanthine,
(23) 1-[(benzo[c][1,5]naphthyridin-6-yl)methyl]-3-methyl-7-(2-butyn-1-yl)-8-((R)-3-amino-piperidin-1-yl)-xanthine,
(24) 1-[(1H-perimidin-2-yl)methyl]-3-methyl-7-(2-butyn-1-yl)-8-((R)-3-amino-piperidin-1-yl)-xanthine,
(25) 1-[(benzo[f]quinoxalin-6-yl)methyl]-3-methyl-7-(2-butyn-1-yl)-8-((R)-3-amino-piperidin-1-yl)-xanthine,
(26) 1-[(imidazo[2,1-a]isoquinolin-2-yl)methyl]-3-methyl-7-(2-butyn-1-yl)-8-(3-amino-piperidin-1-yl)-xanthine,
(27) 1-[(imidazo[1,2-a]isoquinolin-2-yl)methyl]-3-methyl-7-(2-butyn-1-yl)-8-(3-amino-piperidin-1-yl)-xanthine,
(29) 1-[(2,3-dihydro-benzo[f][1,4]oxazepin-5-yl)methyl]-3-methyl-7-(2-butyn-1-yl)-8-(3-amino-piperidin-1-yl)-xanthine, and
(30) 1-[(3-oxo-2,3-dihydro-isoindol-1-ylidene)methyl]-3-methyl-7-(3-methyl-2-buten-1-yl)-8-(3-amino-piperidin-1-yl)-xanthine or the salts thereof.

6. A Physiologically acceptable salt of a compound according to claim 1 or 5 with an inorganic or organic acid or base.

7. A Pharmaceutical composition comprising a pharmaceutically effective amount of a compound according to claim 1 together with one or more inert carriers and/or diluents.

8. A method comprising administering to a patient in need thereof a compound according to claim 1 in an amount effective for the prevention or treatment of a disease or a condition selected from the group consisting of type II diabetes mellitus and obesity.

9. A method comprising administering to a patient in need thereof a compound according to claim 1 in an amount effective for the treatment of type II diabetes mellitus.

* * * * *